(12) United States Patent
Cummins et al.

(10) Patent No.: US 12,073,936 B2
(45) Date of Patent: Aug. 27, 2024

(54) METHODS AND SYSTEMS FOR IMPROVED THERAPY DELIVERY AND MONITORING

(71) Applicant: IESO DIGITAL HEALTH LIMITED, Cambridge (GB)

(72) Inventors: Ronan Patrick Cummins, Cambridge (GB); Alan James Martin, Cambridge (GB); Mihai Valentin Tablan, Cambridge (GB); Michael Ewbank, Cambridge (GB)

(73) Assignee: IESO DIGITAL HEALTH LIMITED, Cambridge (GB)

( * ) Notice: Subject to any disclaimer, the term of this patent is extended or adjusted under 35 U.S.C. 154(b) by 848 days.

(21) Appl. No.: 17/055,178

(22) PCT Filed: May 17, 2019

(86) PCT No.: PCT/GB2019/051380
§ 371 (c)(1),
(2) Date: Nov. 13, 2020

(87) PCT Pub. No.: WO2019/220144
PCT Pub. Date: Nov. 21, 2019

(65) Prior Publication Data
US 2021/0202065 A1    Jul. 1, 2021

(30) Foreign Application Priority Data

May 17, 2018 (GB) .................................. 1808051
Nov. 15, 2018 (GB) .................................. 1818640

(51) Int. Cl.
*G16H 20/70* (2018.01)
*G06N 3/08* (2023.01)
*G16H 80/00* (2018.01)

(52) U.S. Cl.
CPC ............... *G16H 20/70* (2018.01); *G06N 3/08* (2013.01); *G16H 80/00* (2018.01)

(58) Field of Classification Search
CPC ........ G16H 20/70; G16H 80/00; G16H 50/50; G06N 3/08; G06N 3/02
See application file for complete search history.

(56) References Cited

U.S. PATENT DOCUMENTS 11,538,583 B2 * 12/2022 Isobe ...................... G16H 10/60
11,791,034 B2 * 10/2023 Granato ................. G16H 50/20
                                                                706/12

(Continued)

FOREIGN PATENT DOCUMENTS

WO    2016071659 A1    5/2016
WO    2019220144 A1    11/2019

OTHER PUBLICATIONS

Brown et al., "Therapist-Client Interactions in Motivational Interviewing: The Effect of Therapists' Utterances on Client Change Talk", Alcohol and Alcoholism, Apr. 12, 2018, 53(4) 408-411 doi: 10.1093/alcalc/agy027 (Year: 2018).*

(Continued)

*Primary Examiner* — Marie P Brady
(74) *Attorney, Agent, or Firm* — ALSTON & BIRD LLP

(57) ABSTRACT

A computer-implemented method is provided for taking one or more action relating to therapy. The method comprising: receiving text data relating to a therapy session between a therapist and a patient; dividing the text data into a plurality of utterances; assigning a semantic representation to each of the plurality of utterances to produce a plurality of assigned utterances; aggregating the plurality of assigned utterances to form a representation of the therapy session; providing an output prediction, based on the representation of the therapy session and optionally one or more further input, of one or more characteristic of at least one of the patient, the therapist (Continued)

and the therapy; taking one or more action relating to the therapy, wherein the one or more action is selected based on the output prediction meeting a predetermined criterion.

19 Claims, 18 Drawing Sheets

(56) References Cited

U.S. PATENT DOCUMENTS

| | | | | |
|---|---|---|---|---|
| 2005/0228236 | A1* | 10/2005 | Diederich | G10L 17/26 128/920 |
| 2013/0316324 | A1* | 11/2013 | Hoffmann | G09B 7/00 434/362 |
| 2014/0280136 | A1* | 9/2014 | Marshall | G06Q 10/0637 707/736 |
| 2015/0305662 | A1* | 10/2015 | Kilmer | A61B 5/164 600/476 |
| 2017/0084295 | A1* | 3/2017 | Tsiartas | G10L 17/08 |
| 2018/0150605 | A1* | 5/2018 | Co | G16H 40/20 |
| 2019/0013092 | A1* | 1/2019 | Van Halteren | G09B 19/00 |

OTHER PUBLICATIONS

ISR—WO from parent application PCT/GB2019/051380 dated Sep. 11, 2019.

* cited by examiner

Fig. 6

GREETING

Hello John, are you there? 

 Hi, yes, I'm here.

OTHER

Great. Welcome to this evening's session. I've had a look at your questionnaires and noticed that your mood scores have improved slightly this week. 

MOOD CHECK

How are you feeling at the moment? 

 I'm feeling OK, I think. My anxiety has subsided a bit, but I guess that is because haven't put myself in any anxious situations.

OBTAIN UPDATE

How has your week been since our last session? 

 It's been OK. At the weekend I went for a coffee with a friend who I haven't seen for a long while.

THERAPEUTIC ALLIANCE

That's good to hear. 

 Then we went for a walk in the park, it was nice to enjoy the good weather.

OTHER

Sounds nice. Yes, it was so warm over the weekend. 

REVIEW HOMEWORK

So, did you manage to complete the thought diary I sent you last week? 

 Yes, I did.

Fig. 14

METHODS AND SYSTEMS FOR IMPROVED THERAPY DELIVERY AND MONITORING

FIELD OF THE INVENTION

This invention relates to an improved system and method for use in the treatment of psychological disorders in patients. It relates to a system, device, apparatus, program and method for analysing the content of a therapy session. Based on the analysis, correlations are identified between the contents of therapy interventions and clinical outcomes for patients, and therefore recommendations to the therapist, automatic quality assurance of therapy sessions and improved patient outcomes are provided.

BACKGROUND OF THE INVENTION

A computer-based system for providing therapy is described in WO 2016/071660 A1 (which is hereby incorporated by reference). Among other things, the system enables patients and therapists to exchange messages, particularly text-based messages during sessions and courses of therapy. This application relates to certain technical improvements to such a system. The improved system may be used for the treatment of psychological disorders in patients, thereby improving patient outcomes.

Common mental health disorders including depression and anxiety are characterized by intense emotional distress, which affects social and occupational functioning. About one in four adults worldwide suffer from a mental health problem in any given year. In the US, mental disorders are associated with estimated direct health system costs of $201 billion per year, growing at a rate of 6% per year, faster than the gross domestic product growth rate of 4% per year. Combined with annual loss of earnings of $193 billion, the estimated total mental health cost is at almost $400 billion per year. In the UK mental health disorders are associated with service costs of £22.5 billion per year and annual loss of earnings of £26.1 billion.

Various treatment options for common mental health disorders are available to the clinician; these may include one or more of: watchful waiting, guided self-help, traditional cognitive behavioral therapy (CBT), computerised or online CBT, internet-enabled CBT (IECBT), exercise, psychological interventions (brief, standard or complex), medication, social support, combined treatments, and/or electroconvulsive therapy (ECT).

Online therapy, including internet-enabled cognitive behavioral therapy (IECBT), offers significant advantages over standard care. Internet-enabled cognitive behavioral therapy (IECBT) is a type of high-intensity online therapy used within an Improving Access to Psychological Therapies (IAPT) program. Within IAPT using IECBT, patients are offered scheduled one-to-one sessions with an accredited therapist, similar to face-to-face programs, whilst also retaining the advantages of text-based online therapy provision including convenience, accessibility, increased disclosure and shorter waiting times. The improvement rate for patients treated with IECBT is significantly higher than for severity-matched patients treated with standard care.

The interaction between a therapist and a patient during a one-to-one therapy session is a very important part of the therapy process. Little is known about variation between individual therapy sessions, both in terms of the delivery style and the content of the therapist interaction with the patient, and also how this impacts the quality of the therapy, i.e. the likelihood of a patient improving or recovering.

Compared to the treatment of physical conditions, the average quality of care of mental health disorders remains poor and the rate of improvement in treatment is slow. Outcomes for many mental disorders have stagnated since the original treatments were developed and in some cases the efficacy of psychotherapy appears to be reducing over time. Improving the effectiveness of treatment for any disorder is dependent upon accurate measurement of treatment delivery and an understanding of how the treatment works. Whilst it is relatively simple to monitor and measure the delivery of most medical treatments (e.g. the dosage of a prescribed drug given), monitoring the delivery of psychotherapy (i.e. determining the 'dose' of psychotherapy delivered) is a significantly greater challenge.

For these reasons, a new approach is required to improve, augment or assist with measuring/evaluating the style and content of therapy sessions, improve the understanding of key features of good (high quality) therapy sessions, and provide feedback to therapists and/or their supervisors, in order to provide improved systems, apparatus, methods and processes for the provision of therapy.

SUMMARY OF THE INVENTION

According to a first aspect of the present invention there is provided:
  a computer-implemented method for taking one or more action relating to therapy, the method comprising:
  receiving text data relating to a therapy session between a therapist and a patient;
  dividing the text data into a plurality of utterances;
  assigning a semantic representation to each of the plurality of utterances to produce a plurality of assigned utterances;
  aggregating the plurality of assigned utterances to form a representation of the therapy session;
  providing an output prediction, based on the representation of the therapy session and optionally one or more further input, of one or more characteristic of at least one of the patient, the therapist and the therapy; and
  taking one or more action relating to the therapy, wherein the one or more action is selected based on the output prediction meeting a predetermined criterion.

In one embodiment of the invention, assigning a semantic representation to each of the plurality of utterances may be performed by at least a first part of a deep learning model, and providing an output prediction of one or more characteristic may be performed by at least a second part of the deep learning model. The first and second parts (portions) of the deep learning model may be considered as providing individual functions within one (composite) model (e.g. the therapy insights model). Alternatively, they may be considered as distinct models operating in tandem to provide complementary functions.

According to another aspect of the present invention there is provided:
  a method for use by a computer-based system for taking one or more actions relating to therapy, the method comprising:
  obtaining, via one or more user interface of the system, text data relating to a therapy session between a therapist and a patient;
  dividing the text data into a plurality of utterances;
  using at least a first part of a deep learning model to assign a semantic representation to each of the plurality of utterances to produce a plurality of assigned utterances;

forming a representation of the therapy session, wherein the representation comprises the plurality of assigned utterances;

using at least a second part of the deep learning model, and an input comprising the representation of the therapy session, to obtain an output predicting a characteristic of the patient, the therapist and/or of the therapy, wherein the deep learning model is trained using a training set comprising, for each of a plurality of other therapy sessions, audio data and/or text data relating to the other therapy sessions and a result of a determination of the characteristic; and causing the system to take one or more actions relating to the therapy, wherein the one or more actions are selected based on the output meeting a predetermined criterion.

In some embodiments of any aspect of the invention each step of the method may be performed in a step-wise manner as set out above, for example first text data is received or obtained, then the text data is divided into utterances, then semantic representations are assigned to the utterances etc. It will be understood by the person skilled in the art that in other embodiments of the invention a number of steps of the method may be performed in any practical order. Alternatively, two or more steps may be conducted contemporaneously.

A plurality of utterances may comprise combined patient and therapist utterances, only patient utterances, or only therapist utterances.

An input may further comprise one or more non-content related session feature and/or patient variable. An optional further input, where present, may comprise non-content related session features and/or patient variables.

The first part of the deep learning model may perform a plurality of instances of assignment to obtain a plurality of outputs from the second part of the deep learning model. The second part of the deep learning model may perform a plurality of instances of obtaining an output predicting a characteristic of the patient, the therapist and/or of the therapy.

In another embodiment of any aspect of the invention, receiving text data relating to a therapy session between a therapist and a patient may comprise receiving text data relating to a plurality of therapy sessions; aggregating the plurality of assigned utterances may comprise forming a plurality of representations each relating to one of the plurality of therapy sessions; and providing an output prediction of one or more characteristic of at least one of the patient, the therapist and the therapy may comprise providing a plurality of output predictions each relating to one of the plurality of therapy sessions.

The assigned utterances may comprise tagged utterances. Tagging is one example of assigning semantic representations to utterances. Other examples of assigning semantic representations to utterances are known to those skilled in the art.

The deep learning model may comprise a bidirectional long short-term memory (BiLSTM) neural network or a hierarchical bidirectional long short-term memory (HiBiLSTM) neural network. In other embodiments, the first part of the deep learning model may comprise a bidirectional long short-term memory (BiLSTM) neural network or a hierarchical bidirectional long short-term memory (HiBiLSTM) neural network.

In some embodiments, the output prediction or output predictions of the method may comprise:
a likelihood of clinical improvement by the patient; and/or
a likelihood of clinical recovery by the patient; and/or
a likelihood of the patient having a particular mental health disorder; and/or
a likelihood of engagement by the patient; and/or
a measure of quality of therapy delivered by the therapist.

In other embodiments, the output or outputs of the model may comprise:
a likelihood of clinical improvement by the patient; and/or
a likelihood of clinical recovery by the patient; and/or
a likelihood of the patient having a particular mental health disorder; and/or
a likelihood of engagement by the patient; and/or
a measure of quality of therapy delivered by the therapist.

In that way, the invention may be used to extract or provide one or more (output) prediction about the therapy, the therapist or the one or more patients, which may be used to improve the provision of the therapy and/or patient outcome. This is expected to increase the quality of the therapy being delivered and improve treatment outcomes for patients. A measure of quality of therapy delivered by a therapist in accordance with the invention may be an automated therapy competency score, for example an automatic therapy competency score (engagement) or an automatic therapy competency score (recovery).

The output or outputs may be generated in real-time whilst the therapy session is ongoing. Alternatively/additionally, the output or outputs may be generated after a particular therapy session or course of therapy sessions has ended. In other embodiments the output prediction or output predictions may be provided in real-time whilst the therapy session is ongoing. In other embodiments the output prediction or output predictions may be provided after a particular therapy session or course of therapy sessions has ended.

A measure of quality of therapy delivered by a therapist may be considered to be a measure of the dose of therapy delivered to a patient. By providing an indication of the particular aspects of therapy that are positively correlated with patient improvement, and additionally or alternatively a measurement of the absolute quantity or proportion of those aspects delivered by a therapist, the invention provides an approach to determine the effective dose of therapy delivered.

The one or more action in accordance with any aspect or embodiment of the invention may comprise, in response to the output or output prediction meeting a predetermined criterion, initiating an automated therapist support process that comprises providing information to the therapist. The information provided to the therapist may comprise a recommendation to either increase or decrease the number or frequency of utterances belonging to one or more categories, in order to improve the quality of the therapy and therefore clinical outcome. Where the therapy is provided partially or wholly by a computer-based system, the information may be provided to the therapist by that system.

Alternatively/additionally, the one or more action in accordance with any aspect or embodiment of the invention may comprise, in response to the output or output prediction meeting a predetermined criterion, initiating an automated quality assurance process that comprises alerting a supervisor. Alerting a supervisor may comprise recommending one or more further action. The one or more further action would suitably be selected to be appropriate to the criterion met by the output or output prediction, and would be designed to improve the patient outcome by improving the provision of therapy, either by increasing the quality of therapy provided by the existing therapist, or by reallocating the patient to a different (more experienced) therapist. Automated QA provides benefits over conventional QA methods (e.g. manual tagging of therapy session utterances by experienced therapists). Automated QA is expected to perform more consistently than human tagging/analysis, where individual taggers may differ in their opinion. Furthermore, the cost of therapy QA provision by experienced therapists (both financial and in terms of allocation of time of experienced therapists) is much greater than the cost of therapy QA provision by the invention. Therefore therapy QA provision by the invention permits more therapy sessions (suitably all therapy sessions) to be analysed in a cost effective manner, reducing the cost of therapy and allowing the attention of experienced therapists (supervisors) to be focused where it is most beneficial.

Alternatively/additionally, the one or more action in accordance with any aspect or embodiment of the invention may comprise, in response to the output or output prediction meeting a predetermined criterion, initiating an automated therapy auditing process that comprises collecting a plurality of outputs or output predictions of the method relating to one or more therapy sessions or one or more therapists.

Alternatively/additionally, the one or more action in accordance with any aspect or embodiment of the invention may comprise, in response to the output or output prediction meeting a predetermined criterion, initiating an automated output or output prediction report to one or more of: the therapist, a supervisor of the therapist, a service to which the therapist belongs and the payer for the therapy.

Alternatively/additionally, the one or more action in accordance with any aspect or embodiment of the invention may comprise, in response to the output or output prediction meeting a predetermined criterion, initiating an automated medical diagnosis process that comprises providing a prediction of the presence of a mental health disorder in the patient.

Alternatively/additionally, the one or more action in accordance with any aspect or embodiment of the invention may comprise, in response to the output or output prediction meeting a predetermined criterion, initiating an automated data collection process that comprises storing the text data, the utterances, the assigned utterances, and/or the representation.

The text data may be provided to one or more of: the patient, the therapist, the supervisor of the therapist, the service to which the therapist belongs and the payer for the therapy.

In accordance with any aspect or embodiment of the invention, the one or more action relating to the therapy may be taken in real-time whilst the therapy session is ongoing. Thereby improvements to the therapy session may be made as soon as they are indicated by the invention.

The therapy may comprise psychotherapy. In some embodiments, the therapy may comprise a talking therapy, or coaching. In some embodiments the therapy may comprise cognitive behavioural therapy (CBT), online CBT or internet-enabled CBT. The patient may have a mental health disorder. Having a mental health disorder (i.e. a psychological condition), or a particular example of such, means a patient who has been labelled accordingly following a traditional (subjective) diagnosis (by a clinician), or who has been predicted to have a mental health disorder or a psychological condition, or a particular example of such, by a suitable computer-implemented method.

In some embodiments in accordance with any aspect of the invention, the mental health disorder may be selected from an adjustment disorder, agoraphobia (with or without panic disorder), unspecified anxiety disorder, chronic fatigue syndrome, chronic intractable pain, depressive episode, dysthymia, an eating disorder, generalised anxiety disorder, hypochondriacal disorder, mental and behavioural disorders due to use of alcohol, obsessive-compulsive disorder, panic disorder (episodic paroxysmal anxiety), post-traumatic stress disorder (PTSD), recurrent depressive disorder, sexual dysfunction, a sleep disorder, social phobias and/or somatoform disorders. In some embodiments in accordance with any aspect of the invention, the mental health disorder may be selected from depression or an anxiety disorder. Other suitable disorders will be known to those skilled in the art.

According to another aspect of the invention there is provided a computer program product comprising instructions which, when the program is executed by a computer, cause the computer to carry out a method according to any aspect of the invention.

According to another aspect of the invention there is provided a non-transitory computer-readable medium comprising instructions which, when executed by a computer, cause the computer to carry out the method according to any aspect of the invention.

According to another aspect of the invention there is provided a data processing apparatus/device/system comprising means for carrying out the method according to any aspect of the invention.

According to another aspect of the invention there is provided a computer program according to the invention, a non-transitory computer-readable medium according to the invention, or a data processing apparatus/device/system according to the invention, for use in the treatment of a mental health disorder.

According to another aspect of the invention there is provided a method of treatment of a mental health disorder in a patient, the method comprising:
  receiving text data relating to a therapy session between a therapist and the patient;
  dividing the text data into a plurality of utterances;
  assigning a semantic representation to each of the plurality of utterances using at least a first part of a deep learning model, to produce a plurality of assigned utterances;
  aggregating the plurality of assigned utterances to form a representation of the therapy session;
  providing an output prediction, based on the representation of the therapy session and optionally one or more further input and using at least a second part of a deep learning model, of one or more characteristic of at least one of the patient, the therapist and the therapy; and
  taking one or more action relating to the therapy, wherein the one or more action is selected based on the output prediction meeting a predetermined criterion.

In some embodiments, one or more steps of the method may be performed by a computer-based system, for example a computer-based system for providing psychotherapy. In some embodiments, the therapy session comprises a psychotherapy session. In some embodiments, the patient may have a mental health disorder; the mental health disorder may comprise for example depression, an anxiety disorder, PTSD, an eating disorder, a sleep disorder or sexual dysfunction.

According to another aspect of the present invention there is provided:

a method of treatment of a mental health disorder in a patient, the method comprising:
obtaining, via one or more user interface of a computer-based system, text data relating to a psychotherapy session between a therapist and the patient;
dividing the text data into a plurality of utterances;
using at least a first part of a deep learning model to assign a semantic representation to each of the plurality of utterances to produce a plurality of assigned utterances;
combining the plurality of assigned utterances to form a representation of the therapy session;
using at least a second part of the deep learning model, and an input formed using the representation of the therapy session, to obtain an output predicting a characteristic of the patient, the therapist and/or of the therapy,
wherein the deep learning model is pre-trained using a training set comprising, for each of a plurality of other therapy sessions, audio data and/or text data relating to the other therapy sessions and a result of a determination of the characteristic; and
causing the system to take one or more actions relating to the therapy, wherein the one or more actions are selected based on the output;
further wherein the method is performed in real-time whilst the psychotherapy session is ongoing.

In some embodiments, the patient may have a mental health disorder; the mental health disorder may comprise for example depression, an anxiety disorder, PTSD, an eating disorder, a sleep disorder or sexual dysfunction.

According to a further aspect of the present invention there is provided a computer program for performing the method(s) of the invention.

According to a further aspect of the present invention there is provided a non-transitory computer-readable medium comprising a computer program for performing the method(s) of the invention.

According to a further aspect of the present invention there is provided a computer-based (computer-implemented) system configured to perform the method(s) of the invention.

Improving quality of care of mental health disorders and improving the efficacy of psychotherapy requires that treatment be delivered as intended, however monitoring and quantifying the delivery of psychotherapy was heretofore a substantial challenge.

The systems and methods of the invention may therefore be used to improve the quality of therapy delivered to patients, and thereby improve patient outcome (likelihood of improvement or recovery). The invention may also be used to improve and refine the therapy delivered to particular patient groups, thereby providing differentiated healthcare (personalised medicine). By improving and refining the therapy delivered, patients may be more likely to improve and/or recover, and may require fewer sessions of therapy. This is beneficial to the patient in terms of time, convenience, cost (both of monetary cost of therapy, and also reduced cost from e.g. time off work), and is also beneficial to the therapist or healthcare service in terms of increasing the numbers of patients treatable in a given time, reducing overheads per patient, and increasing profit in a pay-for-value payment model.

The systems and methods described herein represent a new approach for quality controlled behavioral health care. For example, the approach described herein provides a method of monitoring therapists' performance. 'Therapist drift'—the failure to deliver treatments that a therapist has been trained to deliver—is considered one of the biggest factors contributing to poor delivery of evidence based treatment (G. Waller, Evidence-based treatment and therapist drift. Behav. Res. Ther. 47, 119-127 (2009)). Automated monitoring of therapists' performance could help prevent therapist drift and associated lower improvement rate, phenomena that have been particularly noted in the case of more experienced therapists. The approach described herein could also be applied to monitor and inform the practice of face-to-face psychotherapy; methods to capture and categorise face-to-face session content through the use of automatic speech recognition software are in development.

A major factor thought to underlie therapist drift is the increase in the confidence a therapist develops over time in their own knowledge above that of therapeutic guidelines (G. Waller, H. Turner, Therapist drift redux: Why well-meaning clinicians fail to deliver evidence-based therapy, and how to get back on track. Behav. Res. Ther. (2016), doi:10.1016/j.brat.2015.12.005). The aspects of the invention described herein provide valuable improvements over traditional therapy, therapy monitoring and consequent actions, for example by reducing the incidence of therapist drift.

DETAILED DESCRIPTION OF THE INVENTION

The invention relates to computer-implemented methods, computer program products, computer-readable media, data processing apparatus, devices and systems, that provide insights into the content of therapy sessions, and uses of those aspects in the treatment of mental health disorders. The insights thus gained are turned into actions that include: making recommendations to the therapist, providing automatic quality assurance of therapy sessions, and identifying correlations between patient characteristics, contents of therapy interventions, and (clinical) outcomes for the patients.

FIGURES

Figure 1:
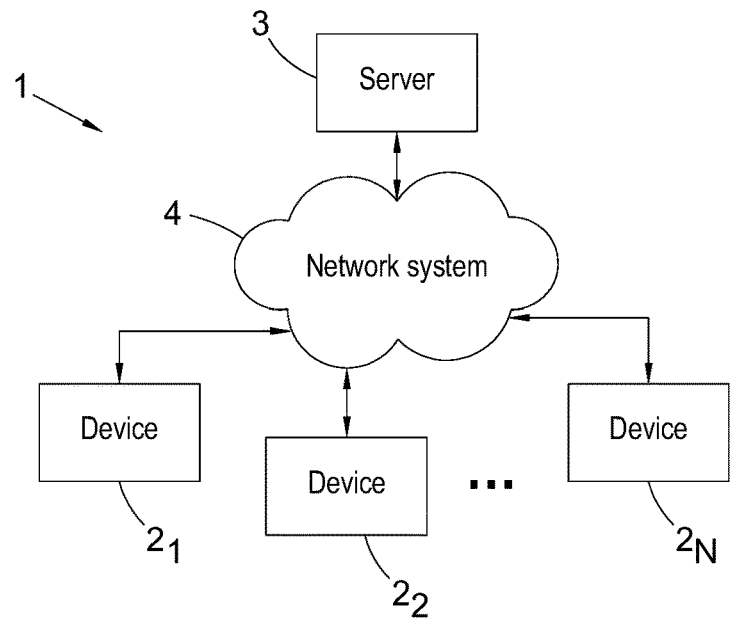
FIG. 1 illustrates an exemplary system for providing therapy.
Figure 3:
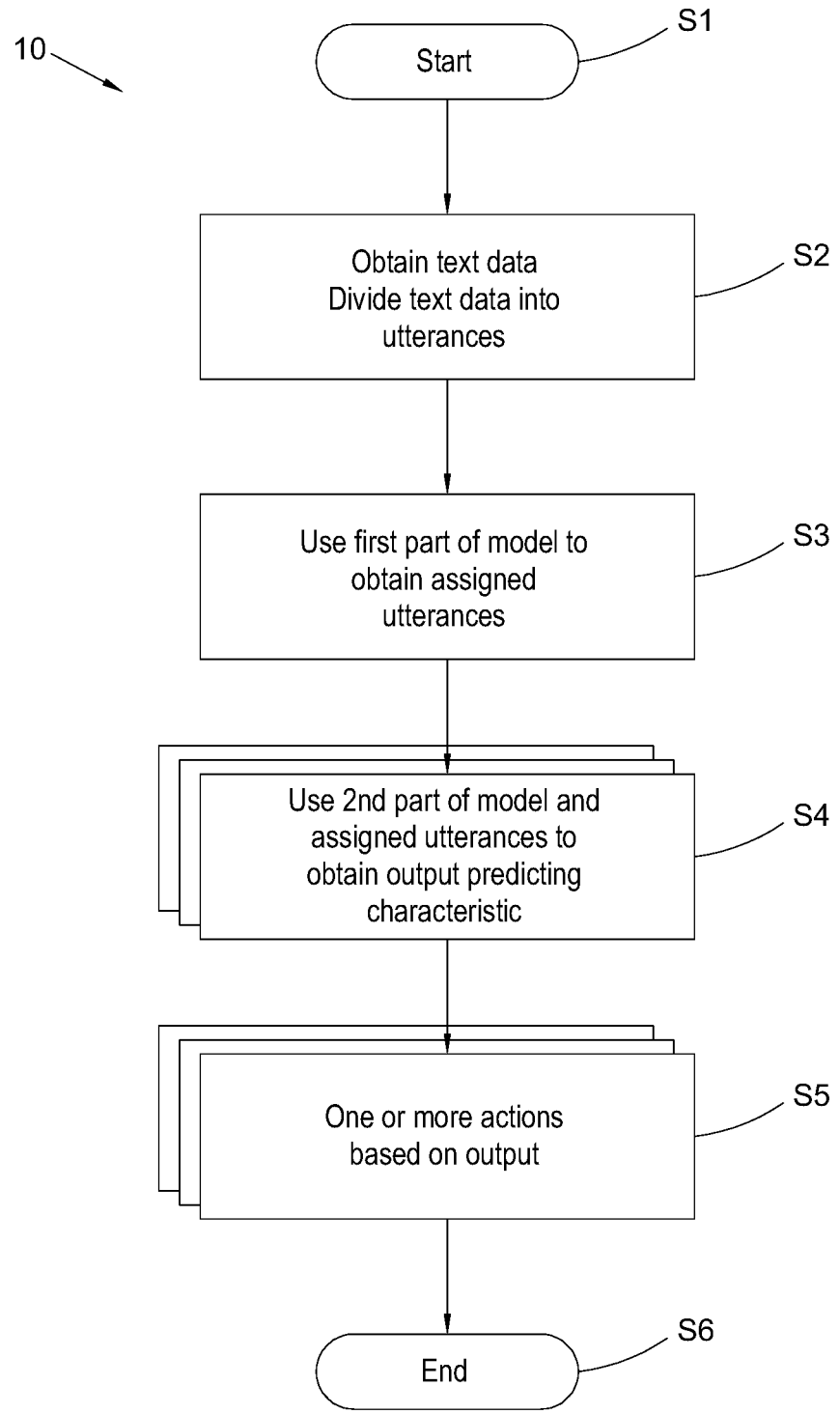
FIG. 3 illustrates a method which may be carried out by the exemplary system of FIG. 1.
Figure 4:
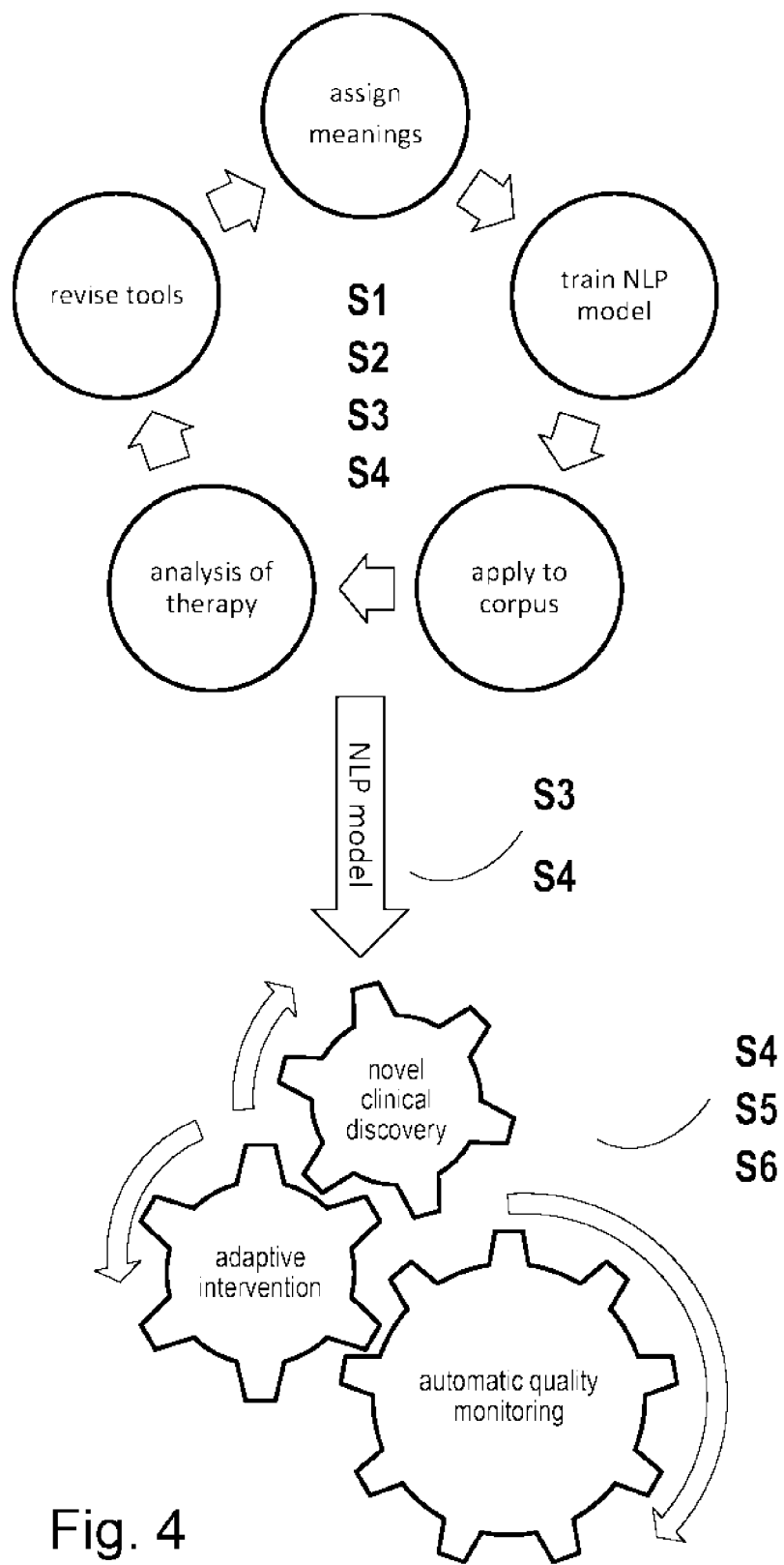

FIG. 4 illustrates the interrelation of therapy insights model development and downstream applications of the system of FIG. 1. S1-S6 represent the stages of the method of FIG. 3. The stages of the method of FIG. 3 may be involved in more than one of model development and downstream applications of the system.

Figure 5:
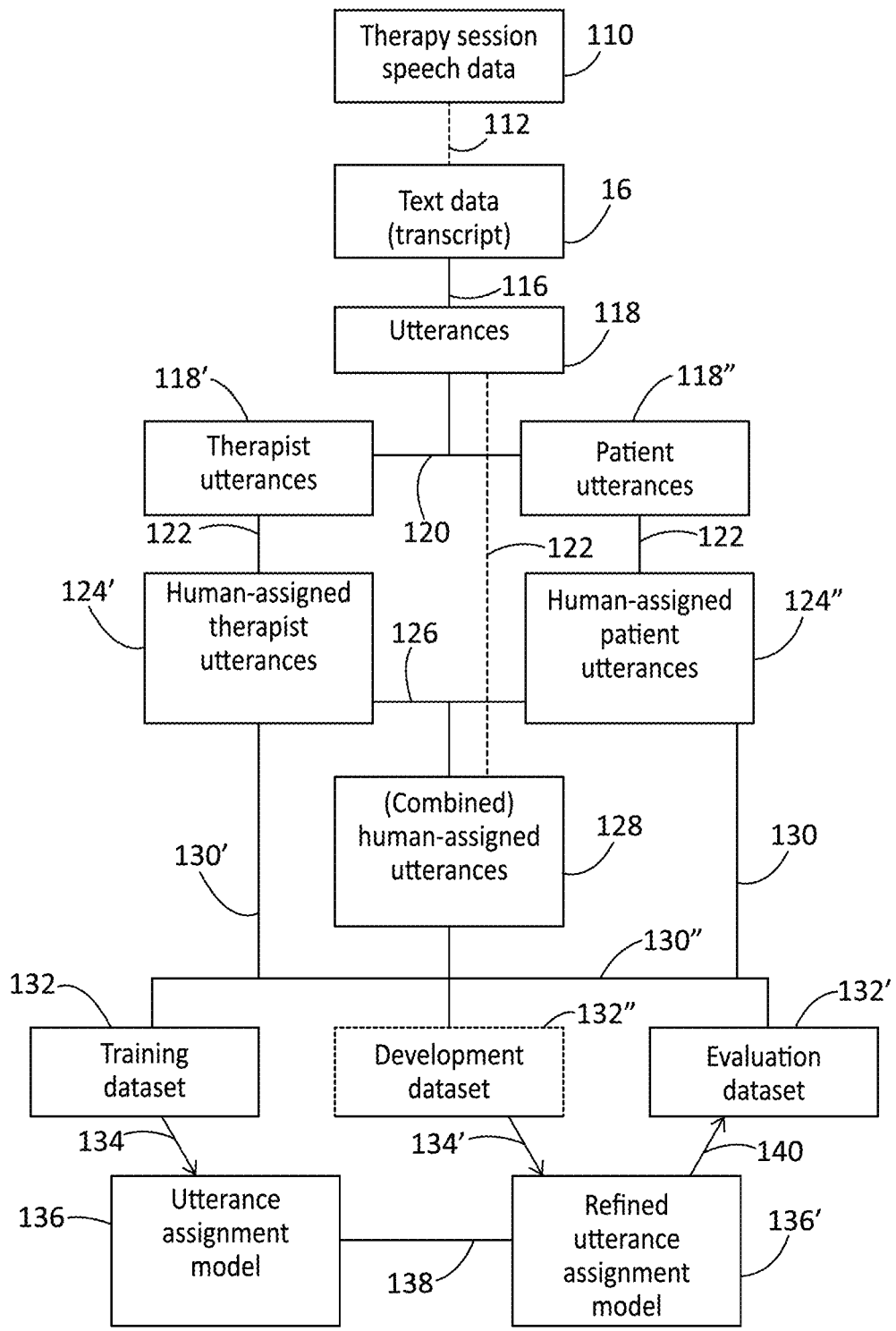

FIG. 5 illustrates a development method of an utterance assignment model (the first part of a therapy insight model) which may form part of the exemplary system of FIG. 1 or a method of the invention.

Figure 6:
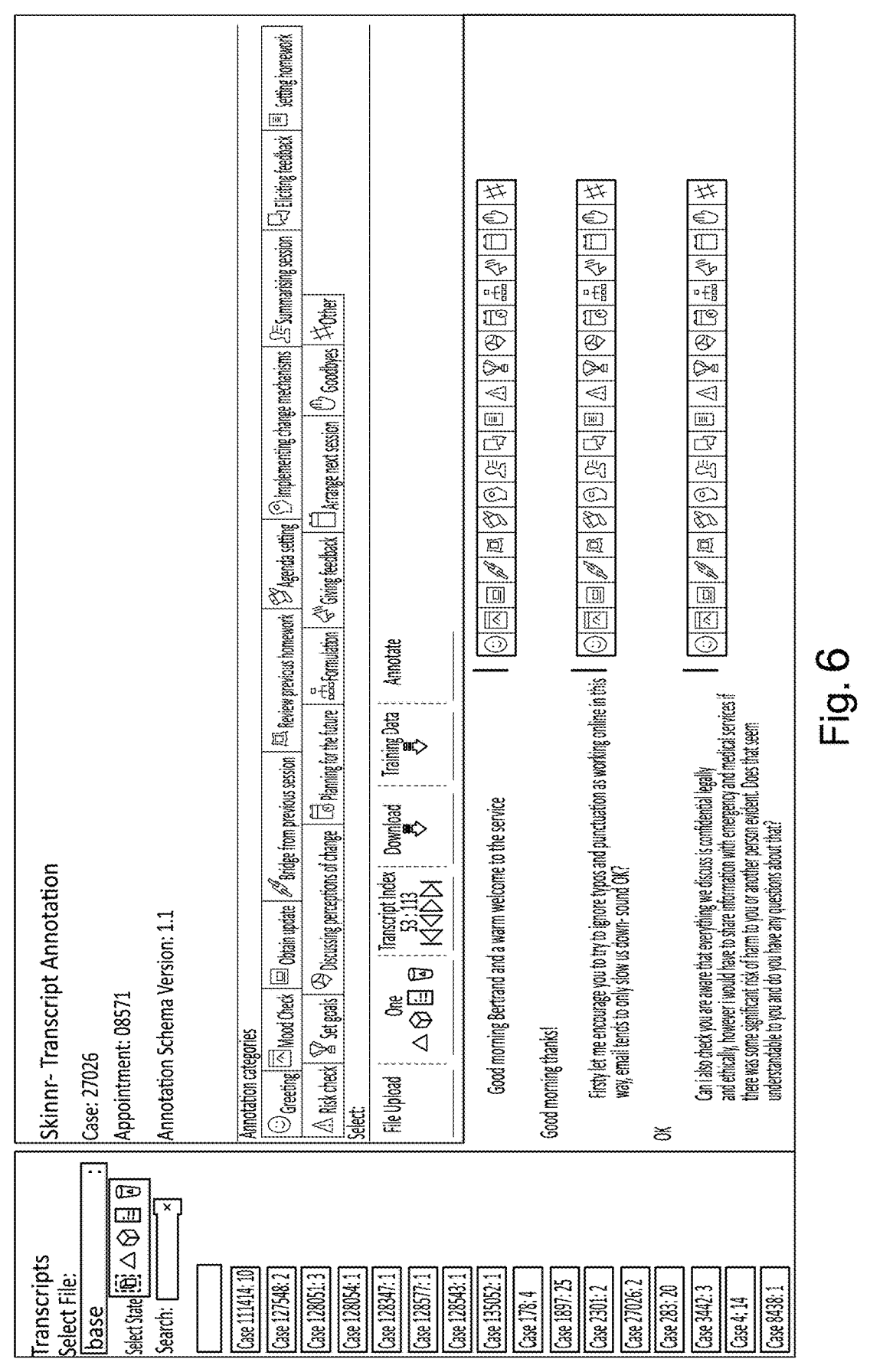

FIG. 6 illustrates an interface of the Skinnr tool which may be used for the gathering of manually-annotated utterances in the method of FIG. 5 or the system of FIG. 1.

Figure 7:
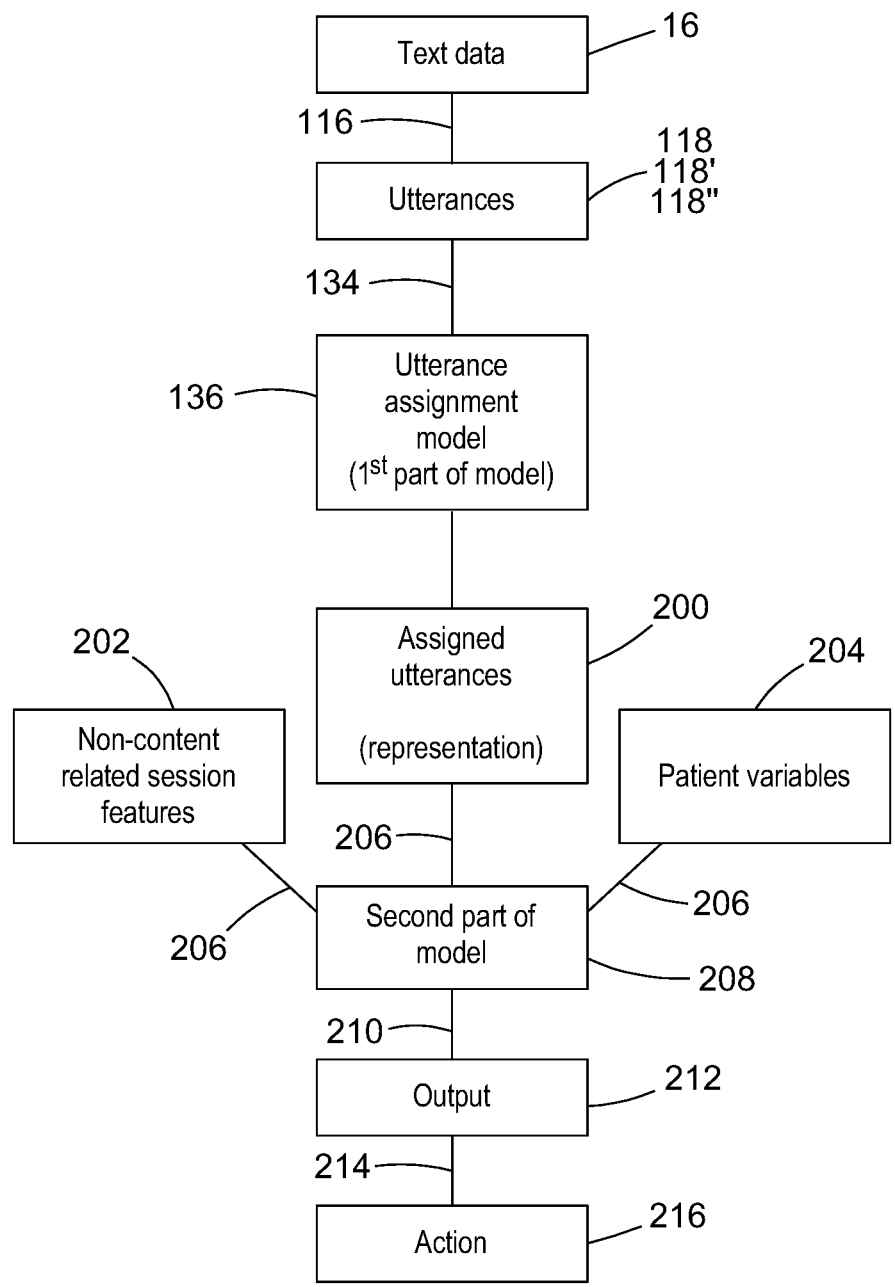

FIG. 7 illustrates the prediction phase of the method of FIG. 3.

Figure 8:
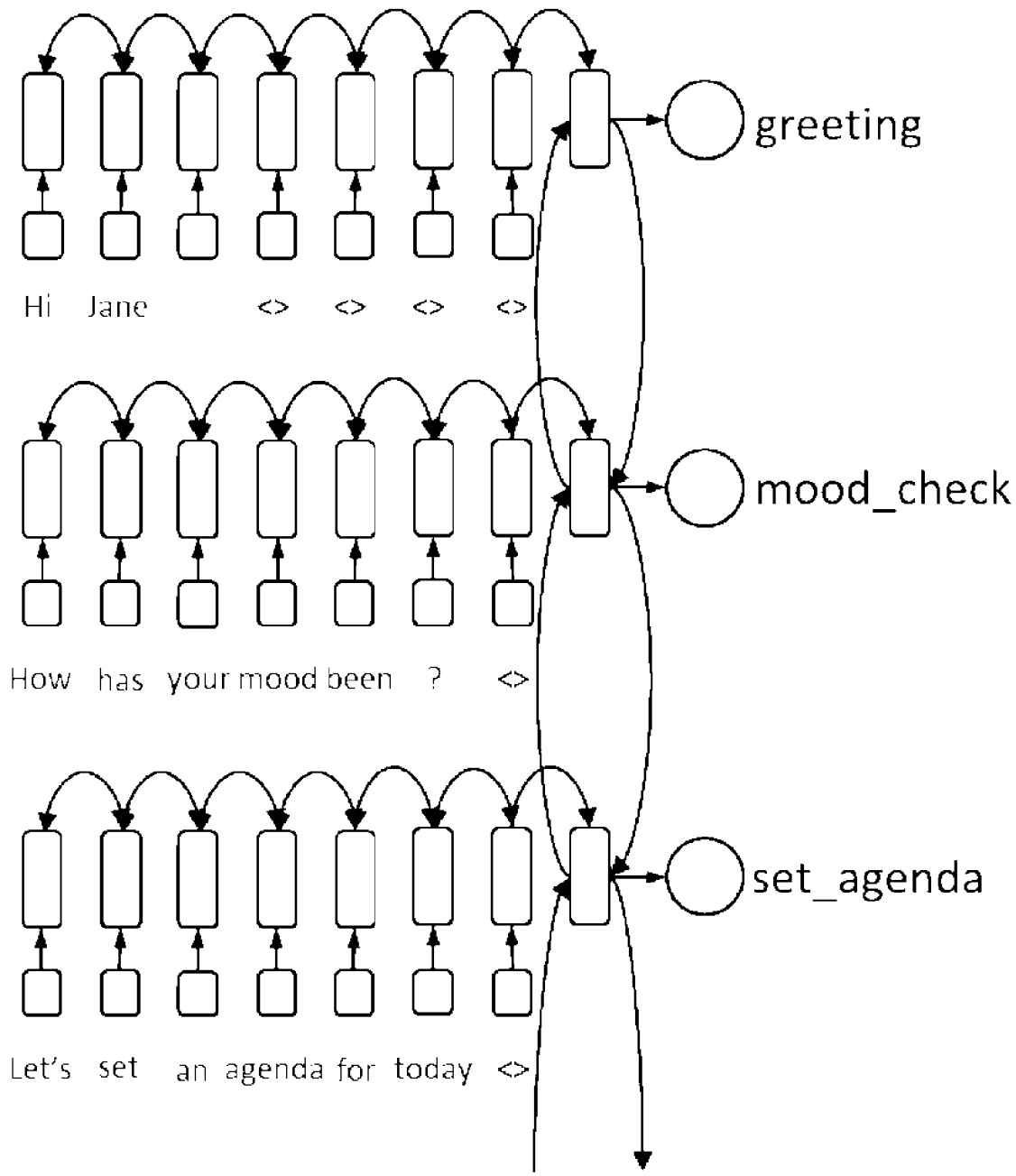

FIG. 8 is a high-level illustration of an utterance assignment (classification) model (first part of a therapy insights model (TIM)) architecture, when tagging is used to assign meaning to utterances.

Figure 9:
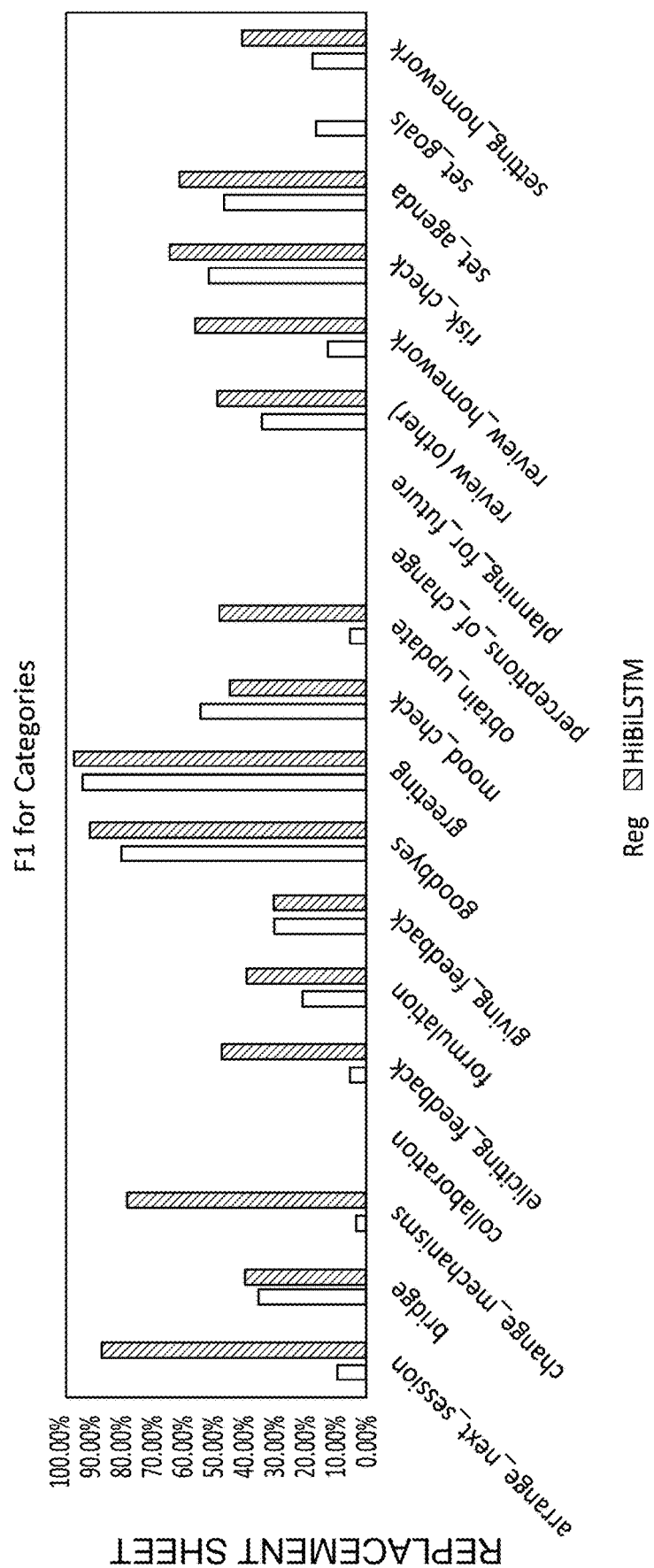

FIG. 9 shows early utterance assignment model performance in comparison with regex classification. The utterance assignment model was trained using 80 transcripts and evaluated on 20 others, F1 is used as a measure of utterance assignment (classification) model performance in comparison with manual annotation of utterances with tags. The machine learned model (HiBiLSTM; Hierarchical Bidirectional LSTM) outperformed regexes (Reg).

Figure 10:
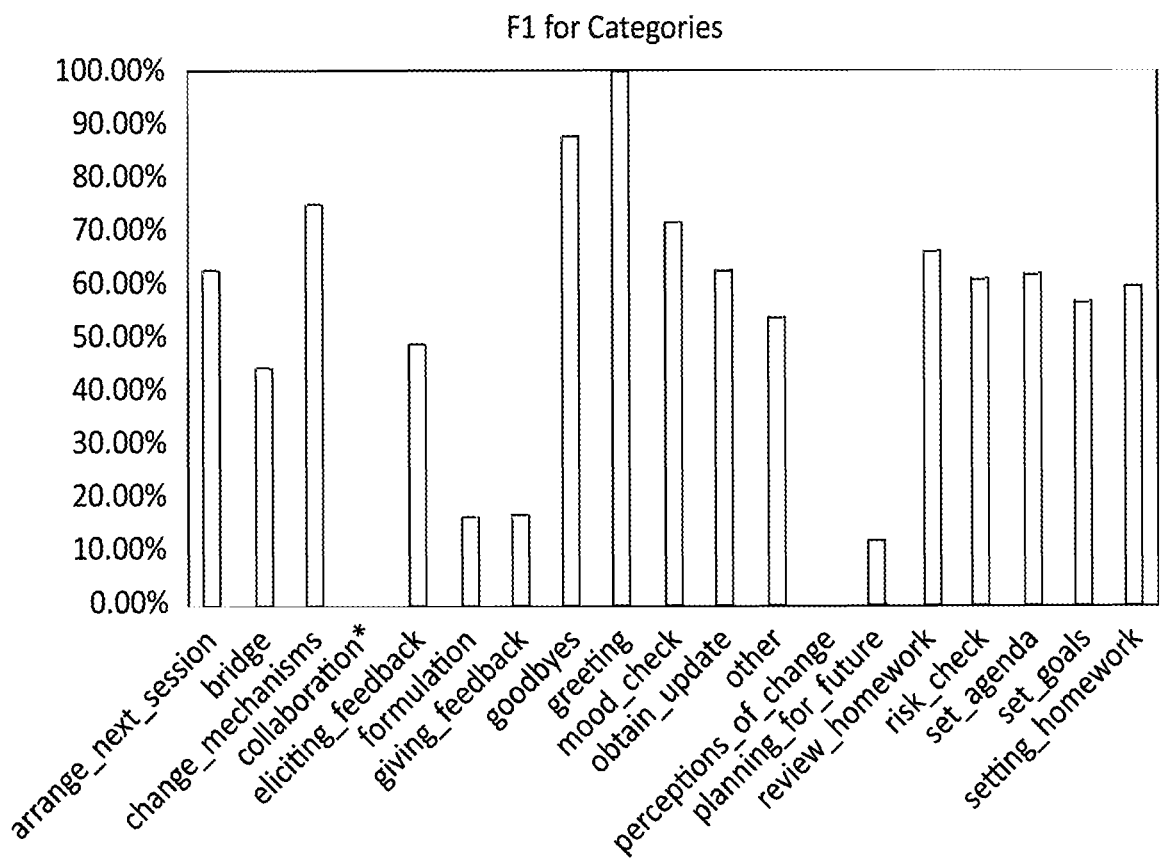

FIG. 10 shows early performance measures of an utterance assignment (classification) model (HiBiLSTM; first part of the therapy insights model). F1 is used as a measure of utterance assignment model performance in comparison with human annotation.

Figure 11A:
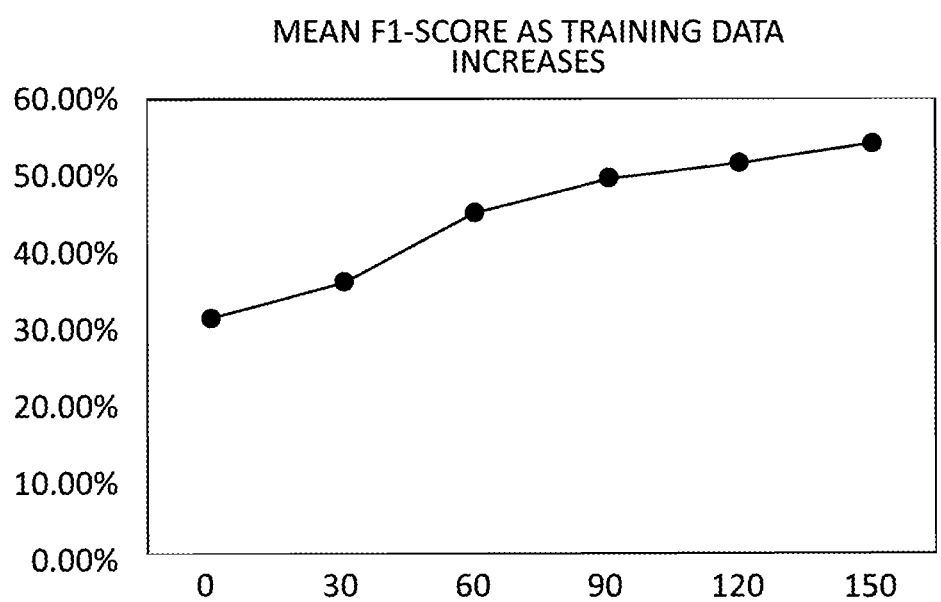

FIG. 11*a* shows the overall F1 measure for the utterance assignment (classification) model (HiBiLSTM; first part of the therapy insights model (TIM)) as a function of training dataset size. The X-axis shows hours of therapy used to train the model.

Figure 11B:
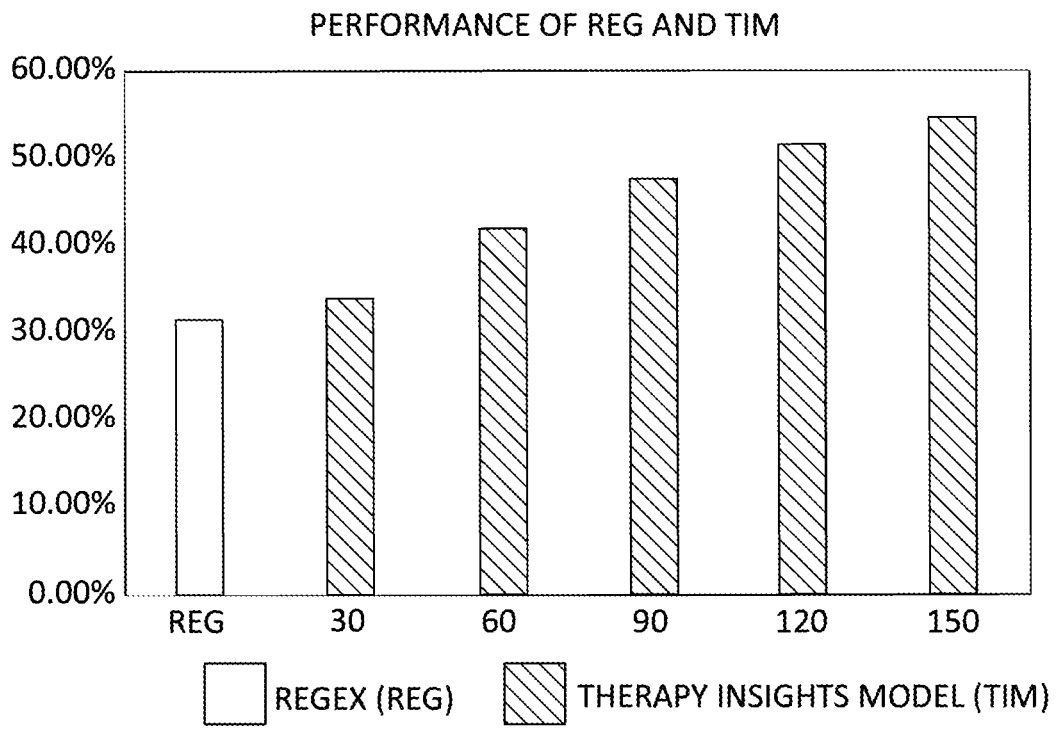

FIG. 11*b* shows overall F1 measure for the utterance assignment (classification) model (HiBiLSTM; first part of the therapy insights model (TIM)) as a function of training dataset size and compared with Regex annotation. The X-axis shows the performance of the Regex-based system (REG), or hours of therapy used to train the utterance classification model in this example.

Figure 12:
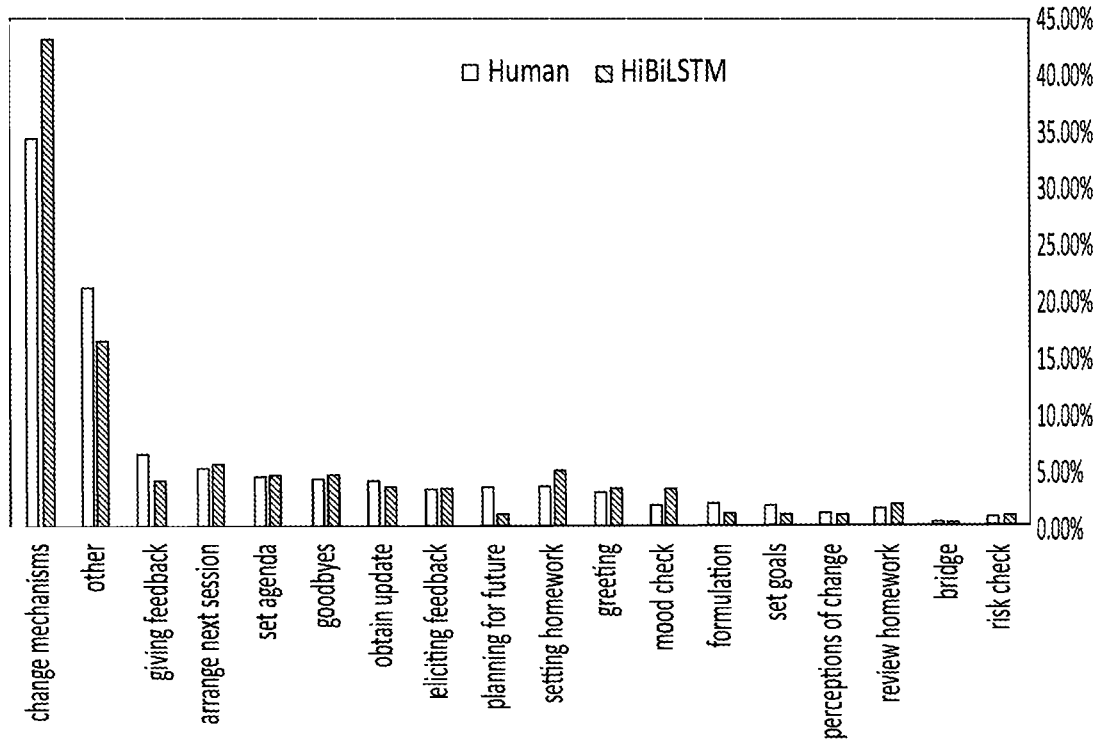

FIG. 12 shows a distribution of therapist utterance types as identified by the utterance assignment (classification) model (first part of the HiBiLSTM therapy insights model) or by human annotation.

FIG. 13 shows a correlation between number of therapist utterances of a particular assigned category as classified by the first part of the HiBiLSTM therapy insights model and clinical outcome in patients. In each chart, the number of utterances is expressed as the mean number of utterances of that category per therapy session (x-axis), whilst the clinical outcome is expressed as the percentage of patients who show clinical improvement ('% improvement') for therapy sessions of a given utterance amount. The dashed horizontal line represents the average clinical improvement rate of 65% (the percentage of all cases that improve during treatment). FIG. 13*a*: clinical improvement correlated with amount of 'agenda setting' utterances per session. FIG. 13*b*: clinical improvement correlated with amount of 'change mechanism' utterances per session. FIG. 13*c*: clinical improvement correlated with amount of 'eliciting feedback' utterances per session. FIG. 13*d*: clinical improvement correlated with amount of 'risk check' utterances per session.

FIG. 14 Example of therapy session transcript. Extract of an IECBT session showing utterances of a therapist (sentence case, right) and patient (sentence case, left). Utterance tag (all capitals) shows the semantic representation assigned by the therapy insights model.

Figure 15:
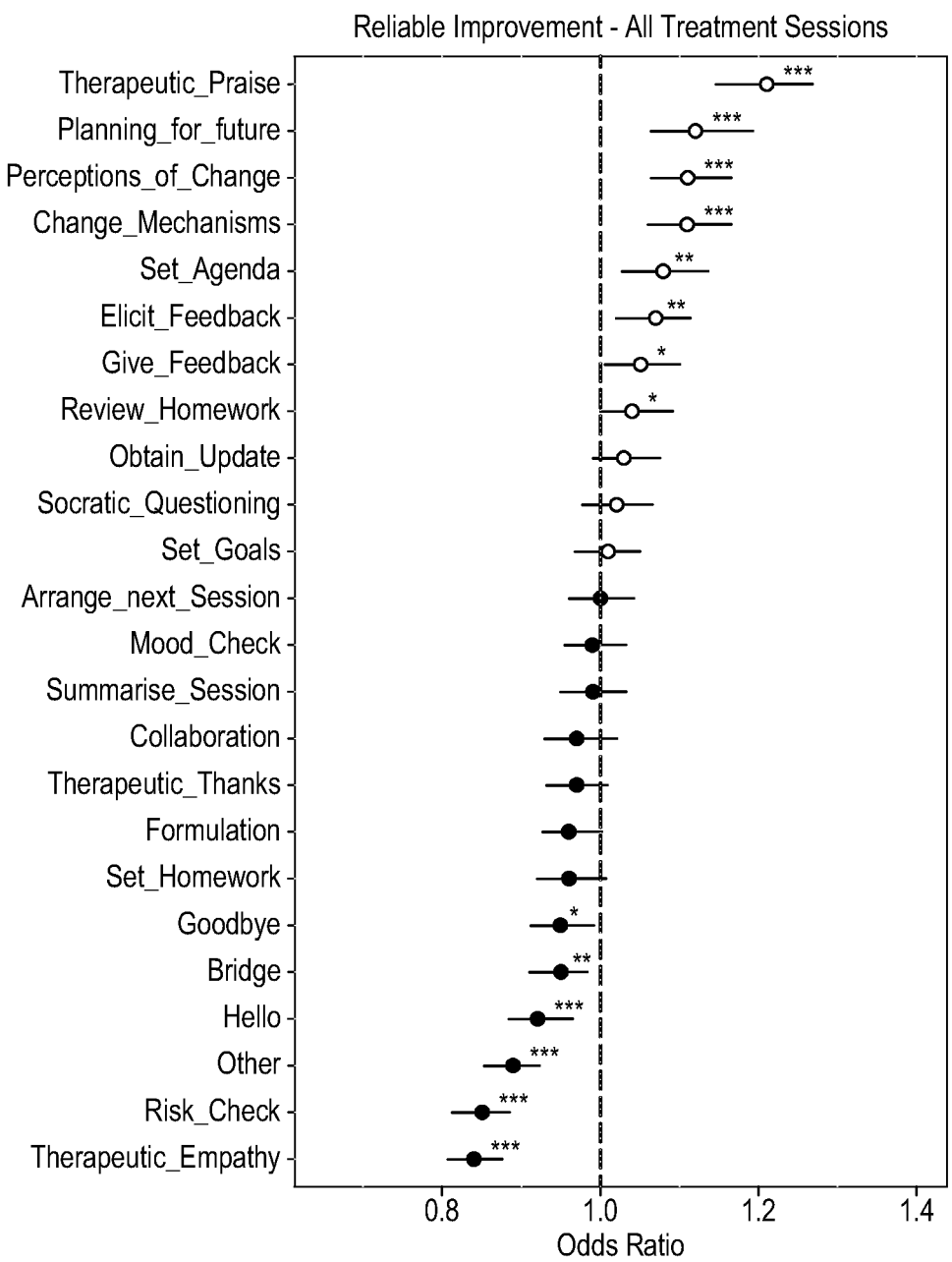

FIG. 15 Predictors of reliable improvement—all sessions. Forest plot of logistic regression model investigating relationship between mean number of words per feature (utterance) across all treatment sessions and reliable improvement. Standardized odds ratios and 95% confidence intervals are shown. Features with a standardized odds ratio of >1.0 are positively correlated with reliable improvement. Adjusted for total number of sessions, symptom severity, patient gender, age, medication status, presence of long-term condition, and session duration. *$p<0.001$, $p<0.01$, *$p<0.05$.

Figure 16:
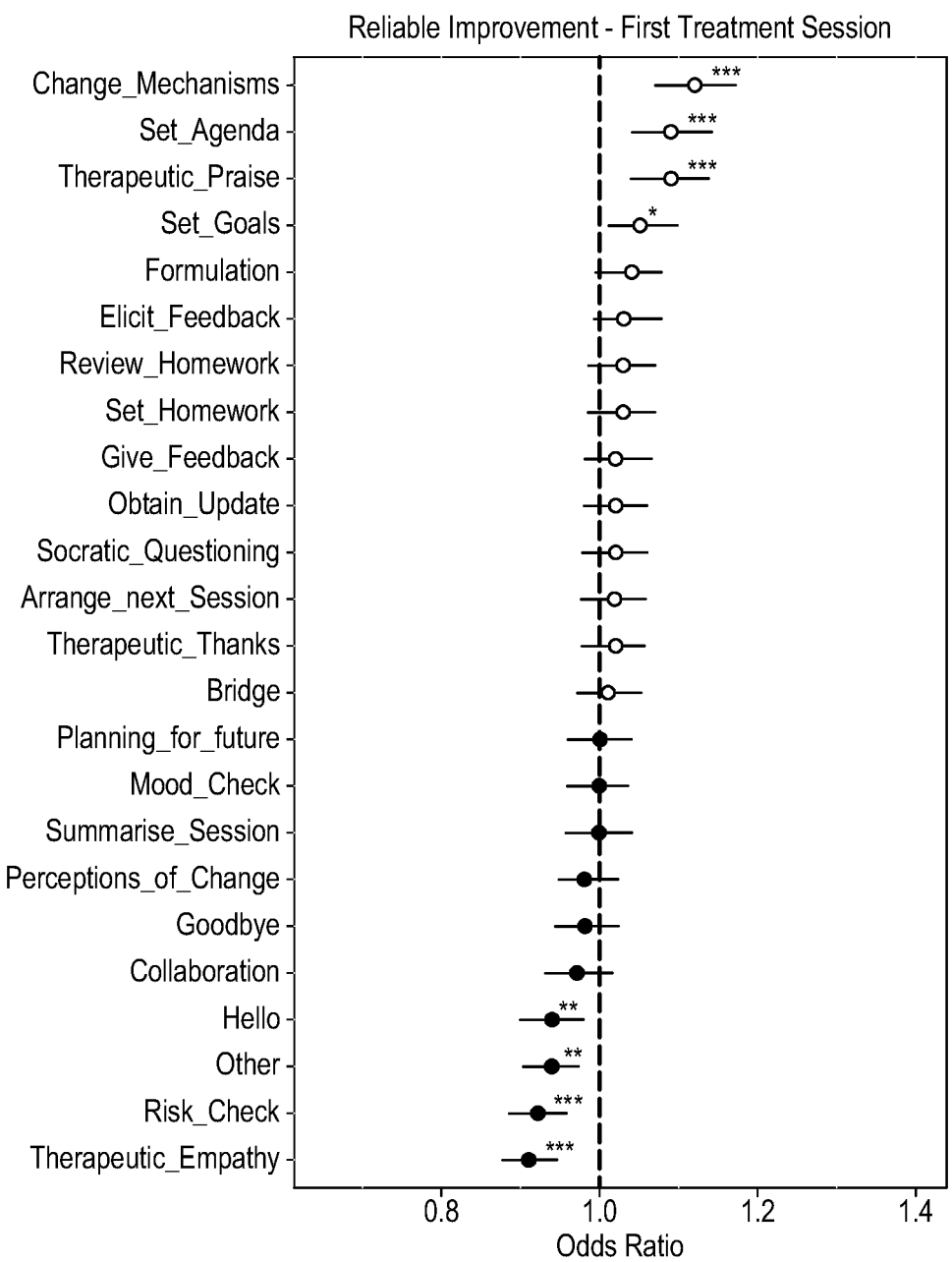

FIG. 16 Predictors of reliable improvement—first session. Forest plot of logistic regression model investigating relationship between mean number of words per feature in the first treatment session and reliable improvement. Standardized odds ratios and 95% confidence intervals are shown. Features with a standardized odds ratio of >1.0 are positively correlated with reliable improvement. Adjusted for symptom severity, patient gender, age, medication status, presence of long-term condition, and session duration. *$p<0.001$, $p<0.01$, *$p<0.05$ FIG. 17 Predictors of IAPT-engagement—first session. Forest plot of logistic regression model investigating relationship between mean number of words per feature in the first treatment session and patient engagement. Standardized odds ratios and 95% confidence intervals are shown. Features with a standardized odds ratio of >1.0 are positively correlated with reliable improvement. Adjusted for symptom severity, patient gender, age, medication status, presence of long-term condition, and session duration. *$p<0.001$, $p<0.01$, *$p<0.05$ FIG. 18 Correlation between therapist competence measures and recovery rate. Chart showing Pearson correlation between human CTSR competency score for a therapist and measured recovery rate for that therapist (dotted trend line); and between automatic therapy competency score and measured recovery rate for that therapist (solid trend line). Therapists were filtered by the number of cases seen: the bottom x-axis (case threshold) indicates the therapists who have seen more than each threshold of cases, whilst the top x-axis shows the number of therapists who are selected by the filtering at the corresponding case threshold.

Figure 19:
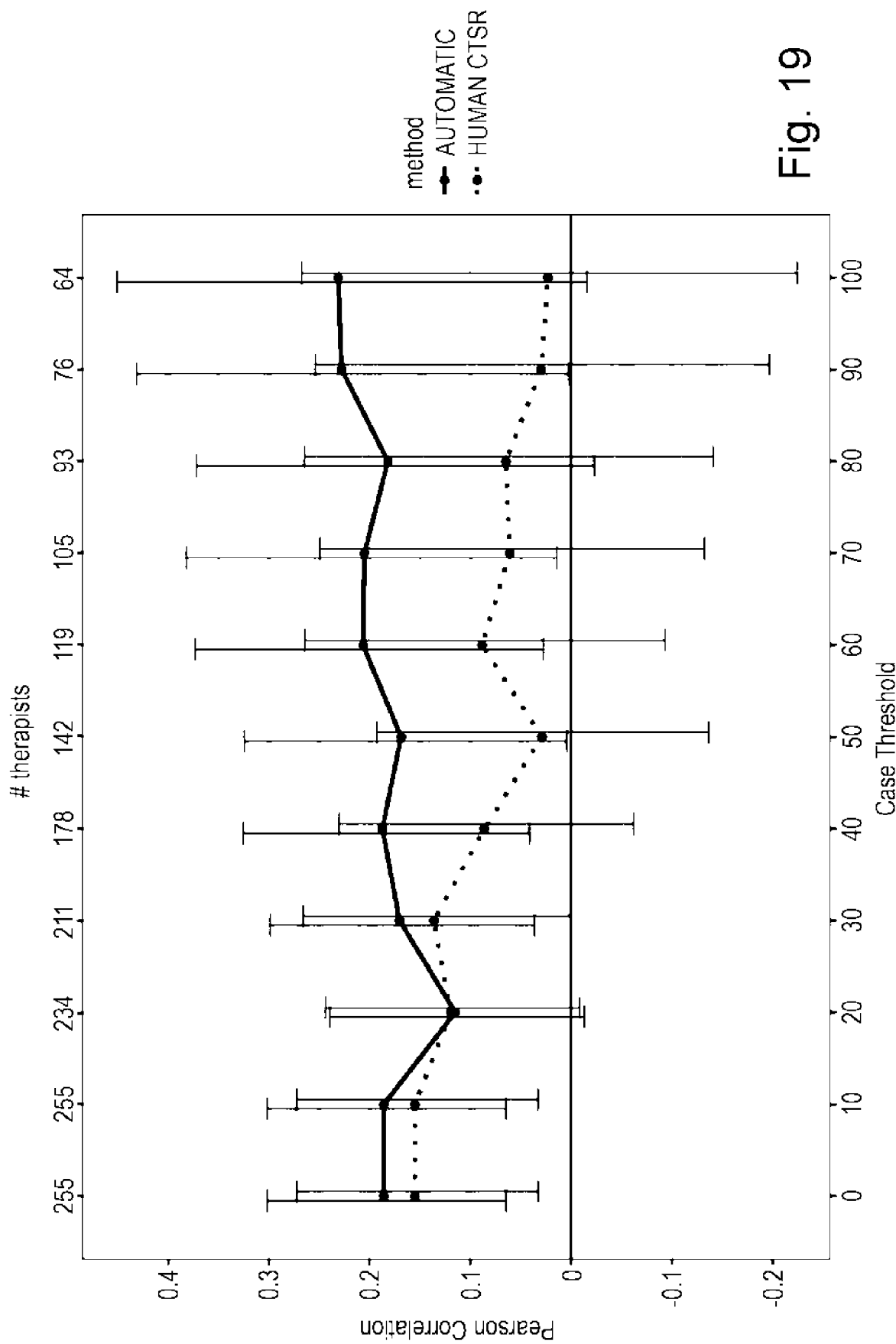

FIG. 19 Correlation between therapist competence measures and engagement. Chart showing Pearson correlation between human CTSR competency score for a therapist and measured engagement rate for that therapist (dotted trend line); and between automatic therapy competency score and measured engagement rate for that therapist (solid trend line). Therapists were filtered by the number of cases seen: the bottom x-axis (case threshold) indicates the therapists who have seen more than each threshold of cases, whilst the top x-axis shows the number of therapists who are selected by the filtering at the corresponding case threshold.

Compared to treatment of physical conditions, the quality of care of mental health disorders remains poor and the rate of improvement in treatment is slow (A. M. Kilbourne et al., Measuring and improving the quality of mental health care: a global perspective. *World Psychiatry.* 2018 February; 17(1):30-38). Outcomes for many mental disorders have stagnated since the original treatments were developed and in some cases the efficacy of psychotherapy appears to be reducing over time. One of the reasons for the gap in quality of care is the lack of systematic methods for measuring quality in the delivery of psychotherapy. As with any evidence based intervention, in order for treatment to be effective it needs to be delivered as intended (also known as treatment integrity). Improving the effectiveness of psychotherapy is therefore dependent upon accurate measurement of how treatment is delivered. However, while it is relatively simple to monitor the integrity and delivery of most medical treatments (e.g. the dosage of a prescribed drug), monitoring the delivery or 'dosage' of psychotherapy is a significantly greater challenge. Most psychotherapeutic treatments comprise a series of private discussions between the patient and clinician. Monitoring the delivery of this type of treatment to the same extent as physical medicine has previously required infrastructure and resources beyond the scope of most healthcare providers.

NICE (National Institute for Heath and Care Excellence) and the APA (American Psychological Association) currently recommend Cognitive Behavioural Therapy (CBT) as a treatment for most common mental health problems, such as depression and anxiety-related disorders. CBT refers to a class of psychotherapeutic interventions informed by the principle that mental disorders are maintained by cognitive and behavioural phenomena, and that modifying these maintaining factors helps produce enduring improvements in patient's presenting symptomology. One third of patients referred to the Improving Access to Psychological Therapies (IAPT) programme in the National Health Service in England in 2016/2017 received CBT, and CBT is among the most common treatment types offered to patients in the US. Despite its widespread use, IAPT currently includes no objective measure of treatment integrity for CBT, while only 3.5% of psychotherapy randomized controlled trials (RCTs) are reported to use adequate treatment integrity procedures.

CBT is the most researched form of psychotherapy and is described as an "evidence based" treatment, however the vast majority of "evidence" refers to measures of treatment outcomes; with relatively few studies investigating the mechanisms of treatment. Quantifiable measures of treatment delivered are needed not only to develop an understanding of the relationship between the 'dosage' of specific aspects of CBT and outcomes, but also, for example, for the development of new psychological treatments needed for the large number of people who do not respond to existing interventions.

The CTSR (Cognitive Therapy Scale Revised (https://www.getselfhelp.co.uk/docs/CTSR.pdf)) tool is the current standard instrument for measuring the competency of CBT practitioners, and is used in both the UK and USA, for example. It is a manual tool whereby a supervisor assesses the competency of a therapist by marking 12 quality items on a 0-6 scale according to how well the therapist displayed those quality items during a particular treatment session. Prior to the development of the CTSR, a previous version, the CTS, was used. Due to the way the CTSR assessment is carried out, and the consequent supervisor time necessitated by this, the assessment is usually only applied to a limited number of therapy sessions. Therefore therapist competency is not assessed for the vast majority of therapy sessions delivered. Furthermore, the quality of the measurement of therapist competency is itself dependent on the ability of the supervisor to use the CTSR scale (or other manual quality assessment measure) effectively. Therefore different supervisors may make divergent assessments of a particular therapy session/therapist competency using the existing manual assessment methods (i.e. inter-rater reliability may be low).

The traditional method of measuring the relationship between treatment delivered and outcomes is to use observational coding methods, typically involving the manual transcription of therapeutic conversations or post-session therapist self-assessment. These are resource intensive exercises which typically means that most studies focus on the effect of a small number of therapeutic factors in a relatively a small sample of patients. To investigate the effect of specific therapeutic factors (or components), previous studies have typically added or removed a component of therapy and measured the effect of this manipulation on outcomes. As with all RCTs, the results of these experimental interventions are difficult to transfer to 'real world' psychotherapy and require sample sizes that are larger than typically used. Improved methods of quantifying treatment delivered must therefore be able to simultaneously measure multiple factors of a therapy session, be applied in a natural clinical context, and be gathered from a sufficiently large enough sample to draw meaningful conclusions.

The present invention permits use of a large-scale data set. For example, a dataset containing session transcripts from over 14,000 cases of internet-enabled CBT (IECBT) (90,000 hours of therapy) is used. In IECBT, a patient communicates with a qualified CBT therapist using a real-time text based message system. IECBT has been shown to be clinically effective for the treatment of depression and is currently deployed within IAPT. Using a deep learning approach, a (first part of a) model was developed to automatically categorise (assign a semantic representation to) therapist utterances according to the role that they play in therapy. In order to train the model, human annotations were gathered from 290 hours of therapy. The trained model was then applied to a large-scale data set using the output of the (first part of the) model (the assigned utterances) to calculate a quantifiable measure of treatment delivered (aggregated assigned utterances forming a representation of a therapy session). Using a logistic regression analysis, the relationship between the quantity (or 'dosage') of each aspect of therapy delivered (the representation) and clinical outcomes was determined. The results reveal that increased quantities of both common factors and CBT-specific change mechanisms are positively associated with reliable improvement in patient symptoms. The present approach provides methods and systems for systematic improvement and quality control of mental health treatment.

Computer-Based System (Computer-Implemented System, Device or Apparatus)

Referring to FIG. 1, a computer-based system 1 for providing therapy includes a plurality of devices $2_1 \ldots 2_N$ connectable to a server 3 via a network system 4.

The system 1 preferably enables therapists and patients to use devices 2 to interact using text-based messages and/or spoken conversation (speech data) during sessions of therapy.

Each device 2 may be a mobile device, such as a laptop, tablet, smartphone, wearable device, etc. Each device 2 may be a (nominally) non-mobile device, such as desktop computer, etc. Each device 2 may be of any suitable type, such as a ubiquitous computing device, etc.

Figure 2A:
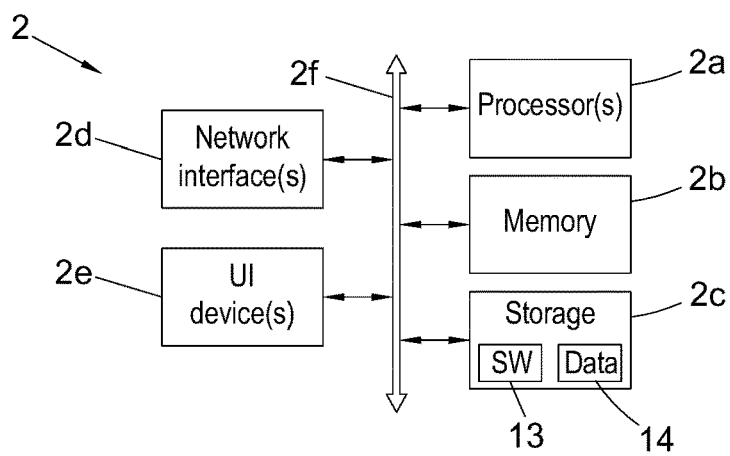
FIG. 2a illustrates a device which may form part of the exemplary system of FIG. 1.

Referring to FIG. 2a, a (typical) device 2 includes one or more processors 2a, memory 2b, storage 2c, one or more network interfaces 2d, and one or more user interface (UI) devices 2e. The one or more processors 2a communicate with other elements of the device 2 via one or more buses 2f, either directly or via one or more interfaces (not shown). The memory 2b includes volatile memory such as dynamic random-access memory. Among other things, the volatile memory is used by the one or more processors 2a for temporary data storage, e.g. when controlling the operation of other elements of the device 2 or when moving data between elements of the device 2. The memory 2b includes non-volatile memory such as flash memory. Among other things, the non-volatile memory may store a basic input/output system (BIOS). The storage 2c includes e.g. solid-state storage and/or one or more hard disk drives. The storage 2c stores computer-readable instructions (SW) 13. The computer-readable instructions 13 include system software and application software. The application software may include a web browser software application (hereinafter referred to simply as a web browser) among other things. The storage 2c also stores data 14 for use by the device 2. The one or more network interfaces 2d communicate with one or more types of network, for example an Ethernet network, a wireless local area network, a mobile/cellular data network, etc. The one or more user interface devices 2e may include a display and other output devices such as loudspeakers. The one or more user interface devices 2e may include a keyboard, pointing device (e.g. mouse) and/or a touchscreen, and other input device such as microphones, sensors, etc. Hence the device 2 is able to provide a user interface for e.g. a patient or therapist.

Figure 2B:
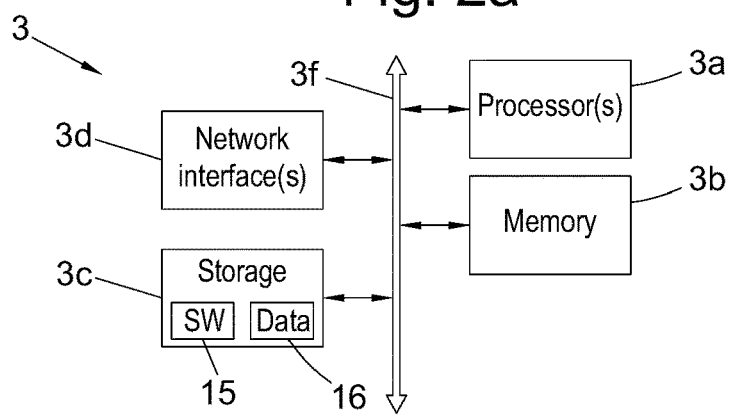
FIG. 2b illustrates a server which may form part of the exemplary system of FIG. 1.

Referring to FIG. 2b, a (typical) server 3 may include one or more processors 3a, memory 3b, storage 3c, one or more network interfaces 3d, and one or more buses 3f. The elements of the server 3 are similar to the corresponding elements of the device 2. The storage 3c stores computer-readable instructions (SW) 15 (including system software and application software) and data 16 associated with the server 3. The application software may include a web server among other things. Alternatively/additionally, the server 3 may correspond to a virtual machine, a part of a cloud computing system, a computer cluster, etc.

Referring again to FIG. 1, the network system 4 may include a plurality of networks, including one or more local area networks (e.g. Ethernet networks, Wi-Fi networks), one or more mobile/cellular data networks (e.g. $2^{nd}$, $3^{rd}$, $4^{th}$ generation networks) and the Internet. Each device 2 is connectable to the server 3 via at least a part of the network system 4. Hence each device 2 is able to send and receive data (e.g. data constituting speech) to and from the server 3.

The computer-based or computer-implemented system (device or apparatus) may comprise one or more computer readable memory comprising one or more computer executable instructions, at least one computer processor operatively connected to the one or more computer readable memory, the at least one computer processor being configured to execute the one or more computer executable instructions to effectuate operations that comprise one or more methods of the invention as set out below.

Further, the invention may comprise a computer process for controlling a device (e.g. a system, an apparatus, a computer device, a mobile device, and/or a smartphone device) that includes at least a user interface, at least one wireless communication unit, one or more computer readable memory including one or more computer-executable instructions, and at least one processor component operatively coupled to the one or more computer readable memory, the computer process including operations comprising one or more methods of the invention as set out below.

Method

Referring to FIG. 3, the system 1 may perform a method 10 comprising several steps S1-S6.

Training (Model Development) and Prediction Phases

Some steps of the method, particularly the third and fourth steps S3, S4, may be performed either as part of a training phase or as part of a prediction phase.

The third and fourth steps S3, S4, each involve parts of a deep learning model. Such a model typically has model inputs, model parameters and model outputs.

Training data (hereinafter referred to as a training dataset) is used during the training phase. In some examples, the training dataset includes multiple instances of e.g. human-assigned data. During the training phase, the instances of data are provided as model inputs, and the model parameters are adjusted (i.e. the model is constructed) such that the model outputs optimally predict (assign) the corresponding semantic representations (e.g. labels, tags). All of the data in the training dataset is used collectively to construct the model.

During the prediction phase, an instance of unassigned (e.g. unlabelled, untagged, unclassified) data is inputted to the first part of the constructed model which outputs a corresponding prediction of the semantic representations (e.g. labels, tags, categories, classifications). These (assigned utterances) are then formed (aggregated) into a representation of the therapy session, which is then inputted to the second part of the model.

First Step of the Method

Referring in particular to exemplary FIG. 3, at a first optional step S1, the method 10 starts. The first step S1 may e.g. involve a user (a patient or a therapist) of a device 2 causing the device 2 to establish a communications session with the server 3.

The device 2 and/or the server 3 may enable the patient or therapist to register, to identify and authenticate themselves, etc.

Typically, the device 2 and the server 3 communicate with one another during a communications session and run particular application software (including a web browser, a web server, further application software at the server 3, etc.).

In this way, the device 2 and the server 3 may provide a user interface (e.g. a patient interface) enabling the patient to interact with the system 1.

In a similar way, a device 2 and the server 3 may provide a user interface (e.g. a therapist interface, a patient interface, a supervisor interface, a payer interface) enabling a therapist, a patient, a supervisor or a payer to interact with the system 1. In this way, a device 2 and the server 3 may also provide outputs (output predictions) and automated actions to the users at the end of the method.

Second Step of the Method

Referring in particular to FIGS. 3, 5 and 7, at a second step S2, text data 16 is received. The text data 16 relates to one or more therapy sessions. The text data 16 may be referred to as therapy session transcript(s). The one or more therapy session may be of any length. The text data is provided by the patient and/or by the therapist. The text data relates to the patient and/or the therapist. The text may include free(form) text, i.e. any text may be provided by the patient or the therapist. The text may be in English or in any other language. The therapy session may be any type of therapy session, for example a psychotherapy session, a talking therapy session, or a coaching session.

The text data 16 may be obtained (received) in any suitable way. For example, the text may be inputted as (typed) text by the patient and/or the therapist using the patient interface or the therapist interface of a system, device or apparatus. Optionally, other methods of text data input may be used such as any standard ASR (Automatic Speech Recognition) system to convert 112 the sounds of speech (therapy session speech data 110) into words (text data 16). The text data 16 need not be provided directly by the patient or the therapist.

The text data 16 is divided 116 into utterances 118. The utterances represent short passages/phrases/sentences of speech (conversation, communication). The text data may be divided into utterances at source i.e. when a therapist and a patient exchange text-based messages each individual message in the exchange is considered one utterance. If ASR is used to convert speech into words (text data) the ASR system may nominate portions of speech (e.g. divided by pauses) as individual utterances. Alternatively if a contiguous transcript of a therapy session is provided, this may be subsequently divided into individual utterances.

The utterances 118 from a therapy session may be divided 120 into therapist utterances 118' and patient utterances 118". Each utterance may be automatically identified at source as deriving from either the patient or the therapist by tagging with the particular user interface from which it originated (patient interface or therapist interface). Alternatively, each utterance may subsequently be identified as deriving from either the patient or the therapist. Either the patient utterances 118", the therapist utterances 118' (or a combination of both patient utterances and therapist utterances) may be analysed.

Alternatively, where a contiguous transcript (text data) of a therapy session is provided it may not be possible to identify the source of each utterance as deriving from either the patient or the therapist, in which case the invention may be performed on/with the totality of the text data.

Information relating to the relationship between individual utterances (the order of the utterances during the therapy session) may be retained along with the utterance and used in the methods and systems of the invention; this provides a richer source of information for use in assigning meaning to the utterances. Alternatively, the utterances used may be a pool of utterances, for example all utterances from within one therapy session, or from a plurality of therapy sessions delivered by a particular therapist, or from a plurality of therapy sessions relating to a particular patient, that have been stripped of their relationship information.

During a therapy session, the therapist and patient interact. The therapist poses questions or makes statements (together considered therapist utterances 118'), to which the patient then responds with patient utterances 118". Examples of therapist utterances are included in Table 2 below.

The method may also involve obtaining further data relating to the patient (this further data is referred to as patient data). The patient data may include data relating to patient variables, for example personal data such as age, gender, etc., medical data such as medication use, drugs/alcohol misuse, etc., and so forth. The patient data may be provided by the patient using the patient interface or may be obtained in any other suitable way.

Third Step of the Method

At a third step S3, semantic representations are assigned to the utterances to obtain assigned utterances.

This involves using deep learning processes which may be referred to as a (deep learning) utterance assignment model 136, or the first part or first portion of a (deep learning) therapy insights model.

Semantic representations (meanings) may be assigned to the utterances by the model 136 in a number of ways including:

Identification of intent of an utterance
Identification of intent of an utterance and identification of slots
Embedding in a semantic space
Classifying (tagging) utterances Therefore assigned utterances are those to which a meaning has been assigned by any suitable method.

For example, a first part of a deep learning model may assign a semantic representation that encodes meaning to each of the plurality of utterances in context.

One such semantic representation is a distributed semantic representation which often consists of a fixed-size dense vector that can be used as input to other systems that can provide semantics on a more specific level (such as classification, sentiment analysis, and/or intent representation).

The method may use these distributed semantic representations as input to a classification system which assigns one or more tags to an utterance. These tags convey the role that the utterance plays in therapy. However, more broadly these distributed semantic representations can also be used as input to a system to determine the sentiment of the utterance (e.g. positive, neutral, negative). Furthermore, the distributed semantic representations can be used as input to a system that translates the utterance into an intent representation. An intent representation encapsulates an action or goal that the speaker wishes to achieve and can be associated with optional or required parameters.

The development of the utterance assignment model may be understood by reference to FIGS. 5 to 8. Referring in particular to FIG. 5 which illustrates an exemplary development (learning, training) phase of a utterance assignment model, following the division 116 of the text data 16 into utterances 118, which optionally may further be divided 120 into therapist utterances 118' and/or patient utterances 118", the utterances are manually-assigned (with a semantic representation) 122 to produce human-assigned utterances. The human assigned utterances may comprise human-assigned therapist utterances 124', or human-assigned patient utterances 124", or combined human-assigned utterances 128. Combined human-assigned utterances 128 may be produced by manually-assigning 122 the (original, undivided) utterances 118, or by combining 126 the human-assigned therapist utterances 124' and the human-assigned patient utterances 124".

For example, human-assigned utterances may be produced by manually allocating each utterance to one of a plurality of suitably designed tags (categories). Examples of suitable tags and their design rationale may be found in Examples 1, 5 and 6 below. The suitability of the tags will be determined by the particular characteristics of the input data, and may be determined empirically. One example of a system that may suitably be used for manual annotation is presented in FIG. 6.

Following manual assignment to semantic representations 122, the human-assigned utterances 124',124",128 are divided 130',130" to one of a training dataset 132, an evaluation dataset 132' or optionally a development dataset 132". The training dataset 132 may be used to train 134 a deep learning utterance assignment model (this may also be referred to as the first part of the therapy insights model (TIM)). Following training 134 of the utterance assignment model 136 using the training dataset 132, the utterance assignment model 136 may optionally be further refined 138 by performing fine-tuning of training hyper parameters 134' using the development dataset 132". The performance of the utterance assignment model 136 or the refined utterance assignment model 136' may be evaluated using the evaluation dataset 132', which the utterance assignment model had not previously encountered.

If after training and/or evaluation the particular utterance semantic representations (e.g. categories, tags) designed do not appear to provide appropriate granularity of information relating to the therapy session transcripts (e.g. too many utterances are allocated to one or more semantic representations), the semantic representations used may be refined by the inclusion of one or more level of sub-representation. The model may thus be retrained using these one or more levels of sub-representations, in order to provide more detailed information relating to the transcripts/utterances.

Optionally, the utterance assignment model 136,136' may use active learning to identify transcripts that it finds difficult to assign meanings to (i.e. where the model finds it difficult to assign a plurality of utterances to one or more semantic representations with a high degree of certainty). These transcripts may be automatically recommended by the model for manual assignment. Such manually-assigned transcripts may be used to refine 138 the semantic representation assignment performance of the model 136,136'. Alternatively, the new manually-assigned transcripts may be added to the training dataset 132, and the training 134 of the utterance assignment model 136 may be re-run.

In one non-limiting example of the development of an utterance assignment model, following the division 116 of the text data 16 into utterances 118, which optionally may further be divided 120 into therapist utterances 118' and/or patient utterances 118", the utterances are assigned by human/manual annotation with tags ('tagged') 122 to produce human-annotated utterances. The human-annotated utterances may comprise human-annotated therapist utterances 124', or human-annotated patient utterances 124", or combined human-annotated utterances 128. Combined human-annotated utterances 128 may be produced by manually-annotating ('tagging') 122 the (original, undivided) utterances 118, or by combining 126 the human-annotated therapist utterances 124' and the human-annotated patient utterances 124".

In this example, the human-annotated (tagged) utterances are produced by manually allocating each utterance to one of a plurality of suitably designed tags (categories). Examples of suitable tags for both therapist and patient utterances and their design rationale may be found in Examples 1, 5 and 6. The suitability of the tags will be determined by the particular characteristics of the input data, and may be determined empirically. One example of a system that may suitably be used for manual annotation is presented in FIG. 6.

Assigning a semantic representation to the utterances involves using the first part or portion of a deep learning model. The first part of the deep learning model may include a single layer or multiple stacked layers. The layers may be of various types, such as convolutional neural network layers (see Y. LeCun, L. Bottou, Y. Bengio and P. Haffner, "Gradient-based learning applied to document recognition," Proceedings of the IEEE, vol. 86, no. 11, p. 2278, 1998), recursive or recurrent neural network layers, long short-term memory layers (see S. Hochreiter and J. Schmidhuber, "Long short-term memory," Neural computation, vol. 9, no. 8, p. 1735, 1997), fully connected neural network layers, drop-out layers, and various nonlinearities such as sigmoid, tanh, ReLU, etc.

A deep neural network (DNN) refers to an artificial neural network endowed with complex structure. A convolutional neural network (CNN) is a type of DNN developed for object recognition in images. Recent research suggests that CNNs can also be applied to text, where they can spot linguistic indicators. CNNs ignore most text structure and are only sensitive to very local dependencies. A recurrent neural network (RNN) is a type of DNN that is sensitive to text structure. RNNs are particularly effective at encoding the semantics of short- and medium-length text snippets (up to a sentence). RNNs do not currently work very well on whole documents, although recent developments (e.g. RNNs with attention) attempt to address this issue. Hierarchical applications of RNNs are another way of addressing this shortcoming. One possible type of hierarchical RNN application is where one RNN focuses on the words in an utterance, while another one uses whole utterance representations as inputs.

The deep learning model may be a bidirectional long short-term memory (BiLSTM) neural network; this type of network may be beneficial when the relationship between individual words within an utterance is important for its classification. More specifically, the model may be a hierarchical bidirectional long short-term memory (HiBiLSTM) neural network. When assigning a meaning to (classifying) a particular utterance, the HiBiLSTM model has access to the information from all utterances in the transcript in the correct positions. This allows information from the utterance itself and from surrounding utterances to be used by the machine learning model. By incorporating hierarchical relationship data it is possible to assign meaning to (classify) an utterance by taking into account the content of the utterance and also the context of other neighbouring utterances (e.g. a 'mood_check' utterance tends to occur after a 'greetings' utterance. The use of a model capable of synthesizing a combination of multiple types of data leads to better assignment (e.g. classification and prediction by the model. FIG. 8 illustrates an exemplary HiBiLSTM model architecture.

Where suitable, another possibility is to use an utterance assignment model that does not use deep neural networks, employing instead simpler machine learning methods such as SVM (Support Vector Machines), logistic regression, decision trees, or other more complex techniques, such as random forests, or Bayesian graphical models.

Once the utterance assignment model 136,136' has been trained 134,134' with the manually (human)-assigned (e.g. tagged) data (the training dataset 132 and optionally the development dataset 132"), it may be used to assign semantic representations to the utterances present in additional (previously unseen) therapy session text data.

Assignment of semantic representations to utterances by the trained model may be more consistent than that achieved manually by human assignors (annotators). This is because there may be noise among human assignors (i.e. two humans will not agree 100% of the time on the task). The model is also capable of assigning utterances at a much faster rate than that achievable by human assignors. For example, when assigning semantic representations to utterances by tagging, experienced human annotators may be able to classify around 11,000 utterances (equivalent to ~290 hours of therapy session text data) in 200-500 person-hours, whereas the utterance assignment model (an utterance classification model in this case) can classify approximately 4 million utterances (equivalent to 100,000 hours of therapy) in about 45 minutes.

The absolute number of utterances assigned as belonging to a particular semantic representation for a particular therapy session is an example of a content-related (therapy) session feature. Other examples of content-related session features may be the proportion of utterances from a therapy session transcript assigned to a particular semantic representation, or the frequency of utterances assigned with a particular semantic representation in a given unit time, where the unit time is less than the length of the whole therapy session. Other examples of session features may be found in Example 4 below. The combined one or more content-related session features relating to a therapy session may be referred to as a representation of the therapy session.

The representation (one or more session features, tagged utterances) of a therapy session may be outputted by the first part of the model in real-time (live) whilst a therapy session is ongoing, or ex post facto after the session has ended.

Fourth Step of the Method

Referring again to FIG. 3, at a fourth step S4, a second part of the model (second part of the HiBiLSTM therapy insights model) is used to make a prediction about the patient, the therapist and/or the therapy process. At least one classification/regression process is used to obtain (provide) an output predicting a characteristic of the patient, the therapist and/or the therapy process (an output prediction). The output (prediction) may also be referred to as a hypothesis. The output may represent a correlation with at least one characteristic of the patient (e.g. likelihood of recovery), the therapist (e.g. quality of therapy delivered) and/or of a related therapy process (e.g. quality), as generated by at least one classification/regression process of the method.

A classification process is a machine learning process that associates categorical labels with input data. A regression process is a machine learning process that associates numerical labels/values with input data.

The one or more classification/regression processes may be referred to as the second part of the deep learning model (second part of the HiBiLSTM therapy insights model). The one or more classification/regression processes may also be referred to as the classification/regression portion of the deep learning model. Analysis will be understood to mean the performance of classification and/or regression.

Using the deep learning model (HiBiLSTM therapy insights model), certain therapy session features (including content-related and/or non-content-related) and optionally patient variables may be correlated with a characteristic of the patient, the therapist and/or the therapy process, for example a clinical measure of the patient. Examples of characteristics may include clinical measures such as a patient's likelihood of recovery, likelihood of improvement, or engagement. The one or more content-related session features may be considered a representation of the therapy session. For example, the assigned utterances (utterances with associated meanings or semantic representations) outputted from the first part of the deep learning model (the utterance assignment portion of the model) may be used as the input to the second part of the deep learning model which outputs e.g. a prediction of clinical improvement based on the (totality of the) assigned utterances (representation) inputted. Other inputs to the second part of the deep learning model may include non-content related session features and/or patient variables.

Clinical improvement as used herein is defined as a patient achieving a statistically significant decrease in symptom severity, as measured on the PHQ-9 and GAD-7 scales. This is the definition used by NHS England in IAPT. Recovery as used herein is defined as the severity of symptoms of a particular patient decreasing to be below the clinical threshold on a clinically suitable scale, such as PHQ-9 or GAD-7.

The deep learning model may use a logistic regression model of therapy outcome to correlate certain therapy session features, and optionally patient variables, with patient recovery.

The deep learning model may use a logistic regression model of therapy outcome to correlate certain therapy session features, and optionally patient variables, with patient engagement.

The deep learning model may use a linear regression model of therapy outcome to correlate certain therapy session features, and optionally patient variables, with patient symptoms or recovery.

A group of therapy session transcripts may be pooled for analysis, for example those deriving from a particular patient, a particular patient group, a particular therapist or a particular therapist group may be pooled. Analysing data for a particular group may provide group-specific correlations.

All transcripts for a single case (patient) may be pooled, and the value obtained of one or more session feature (averaged across all pooled transcripts for that case). The values for the one or more session feature (i.e. the representation of the therapy session) may be entered into a logistic regression with treatment outcome (e.g. whether the patient (case) recovered) as a binary outcome.

One example of a (content-related) session feature is the number of utterances that have been assigned to a particular semantic representation. For example, in the case of tagged utterances, those tagged with a particular category, e.g. the category/tag 'eliciting feedback'.

By using a large dataset, the second part of the deep learning model (the second part of the HiBiLSTM therapy insights model) may establish statistically significant correlation(s) between the representation of the therapy session (comprising one or more session features e.g. the number of utterances assigned to a particular meaning) and a characteristic of the patient, the therapist and/or of a related therapy process, e.g. treatment outcome. By selecting a dataset that relates to a particular group of therapy sessions (e.g. relating to a particular patient cohort), correlations specific to that group may be established.

Once these correlation(s) have been established by the second part of the deep learning model (second part of the HiBiLSTM therapy insights model) the second part of the model may be used to make predictions based on the representation (one or more session features) of other (previously unseen) therapy sessions.

The prediction of a characteristic for a therapy session (output prediction) may be outputted (provided) by the second part or portion of the deep learning model (second part of the HiBiLSTM therapy insights model) in real-time (live) whilst a therapy session is ongoing, or alternatively ex post facto after the session has ended.

Thus the first and second parts of the model may be used together to analyse the therapy session, model predicted therapy session features (e.g. numbers of utterances assigned with a particular meaning, e.g. tagged as belonging to one or more category) and predict therapy session outcome (e.g. likelihood of patient recovery). The model as a whole may be used in real-time (live) whilst a therapy session is ongoing, or ex post facto after the session has ended Fifth Step of the Method Referring in particular to FIG. 3 and FIG. 7, at a fifth step S5, one or more actions are taken based on the one or more outputs of the fourth step S4.

As a simple example, an action may involve presenting information relating to one or more outputs (output predictions) (e.g. a prediction of a characteristic of the patient, the therapist and/or the therapy process). The presentation of the information relating to one or more outputs may be made to one or more of e.g. a therapist, a therapy supervisor (e.g. an experienced therapist), a therapist's employer, a healthcare service or a health insurance company. The information may be presented via a therapist interface, or to one or more other suitable interface(s).

The interface(s) may provide a display including one or more session features (a representation of a therapy session) and/or a prediction of therapy outcome based on the session features/representation. The display may also include confidence scores for the predictions. The display may include text and/or graphical representations of the predictions and confidence scores.

Automated Therapist Support

The deep learning model (HiBiLSTM, therapy insights model) may provide automated feedback to a therapist on the quality of the therapy session (e.g. likelihood of improvement of the patient), such that one or more actions may be taken by the therapist e.g. alterations to the current therapy session and/or future therapy sessions. The feedback may be provided to the therapist after completion of the therapy session in order that future therapy sessions may be improved, or alternatively/additionally whilst the therapy session is ongoing (real time or live feedback) so that the therapist may elect to change their current behaviour in order to increase the likelihood of the current therapy session having an improved outcome. In this way the quality of the therapy delivered may be improved and the current patient/future patients are more likely to show good clinical outcome (likelihood of recovery is increased). The method or system may automatically direct the therapist to take actions that are known or expected to result in improvement of the therapy provided.

All session features analysed (the therapy representation) may be presented to the therapist, or alternatively only those session features that indicate below-average performance of the therapist (i.e. where a prediction of low likelihood of good patient outcome is made by the model) may be presented to the therapist. By way of non-limiting example, the utterances forming the transcript of a particular therapy session are assigned to a particular semantic representation using an utterance assignment model, and the number of utterances of each meaning is determined to form session features. One or more session features known to correlate with patient outcome is selected. For example, when assigning meaning by tagging utterances, those utterance categories described in Example 4 below as showing either a positive or a negative correlation with likelihood of patient recovery are selected. Each session feature is compared with a suitable predetermined threshold or criterion.

The threshold or criterion is determined in any suitable way so as to provide a meaningful separation of different likelihoods of patient outcome. The threshold/criterion may be adjusted to balance the risks of false positives and false negatives. For different levels of control, more or fewer thresholds/criteria may be defined as desired. Data from a cohort of patients of known outcome (e.g. recovery) may be used to set the threshold(s)/criteria; the threshold(s)/criteria may then be applied to a matched cohort of new patients.

For example, where the selected session feature relates to an utterance semantic representation category known or suspected to correlate positively with likelihood of patient recovery, the predetermined threshold or criterion is set at a desired minimum level (a predetermined minimum threshold), for example the minimum amount or proportion of utterances of that category known to relate to average likelihood of improvement. In the example given in FIG. 13b, the mean number of 'change mechanisms' tagged utterances per session that correlates with average % improvement is 16-25, therefore a criterion may be predetermined that the desired minimum number of utterances of that category per therapy session is 16.

Where the selected utterance category relates to an utterance category known or suspected to correlate negatively with likelihood of patient recovery, the predetermined threshold or criterion is set at a desired maximum level (a predetermined maximum threshold), for example the maximum amount or proportion of utterances of that category known to relate to average likelihood of improvement.

Each session feature is compared with the predetermined threshold or criterion. Automated feedback is provided to the therapist on one or more session features. Where the predetermined threshold or criterion is a predetermined minimum threshold (i.e. where a session feature is a measure of an utterance category that correlates positively with improved clinical outcome), if the session feature is below (does not meet) that level, the therapist is alerted. Where the predetermined threshold or criterion is a predetermined maximum threshold (i.e. where a session feature is a measure of an utterance category that correlates negatively with improved clinical outcome), if the session feature is equal to or above (meets) that level, the therapist is alerted. Alternatively/additionally, automated feedback on the therapist's performance in relation to each or all of the session features may be provided to the therapist irrespective of whether the session feature is below or above a given predetermined threshold or criterion. Suitably, a therapist is provided with automated feedback on all session features available.

The automated feedback provided to the therapist may take the form of an alert. The automated feedback provided to the therapist may suitably take the form of a visual alert, for example a written (text) alert e.g. an automatically-generated email, a pop-up, a text-box or another form of message generated by the therapy system; alternatively/additionally, the visual alert may be for example a graphical alert e.g. a graphical pop-up, a bar chart, pie chart or line chart that e.g. compares the therapist's performance with the predetermined threshold or criterion. Other suitable alerts may be determined by reference to the particular interface used by the therapist. The alert provided to the therapist may automatically direct the therapist to take one or more actions e.g. suitably to recommend to either increase or decrease (in absolute number or frequency) the utterances belonging to one or more semantic representations, or one or more styles of communication. Alternatively the therapist may be automatically alerted that their performance appears to be of high quality as measured by the one or more metric or criterion, and they should maintain their current therapy delivery. In that way, the therapist is automatically alerted as to the quality of their performance.

For example, where the deep learning model determines in real-time that the likelihood of patient recovery is below average for a particular therapy session because the therapist is not delivering frequent enough utterances of the 'change mechanisms' type in a given unit time (for example 1, 2, 3, 4, 5, 6, 7, 8, 9, 10, 11, 12, 13, 14 or 15 minutes), the system will alert the therapist to the problem (the low likelihood of recovery and/or low frequency of utterances of that category) and automatically recommend that the therapist increases the frequency of utterances of that category. If the therapist responds by increasing the frequency of utterances of the 'change mechanisms' type delivered, the system will indicate that the frequency has increased and/or that the likelihood of recovery of the patient has increased. Therefore the therapist receives real-time feedback on the quality of therapy delivered and is prompted by the system as to how to improve the quality of the therapy.

Furthermore, the feedback provided to the therapist on the quality of the therapy delivered may take into account the characteristics of a particular therapy session. For example, by using the current therapy (e.g. CBT) clinical knowledge, session plans can be prepared automatically ahead of each session according to the patient's presenting condition and the chosen treatment model. The session may be monitored while in progress using the system or method, and the therapist may be alerted if the session appears to diverge from the recommended plan. The therapist may also get hints to help with e.g. time keeping, for example if less than 10 minutes of the session remain, but they have not yet started discussing homework for the next session. Therefore expected changes in utterance frequency during the course of a session may be taken into account.

Suitable recommendations that may be made to a therapist may include specific advice on session content, such as advice to not spend too much time on greetings and bridging, and an emphasis on setting a session agenda.

Automated Quality Assurance

An additional/alternative action that may be taken by the system at step S5 of the method is to perform automated quality assurance (QA) of therapy sessions. A supervisor may be alerted to below-average delivery of therapy by a therapist (e.g. a prediction of below average likelihood of recovery, based on the session features or representation of a therapy session). This alert may take the form of e.g. a quality score for a particular therapy session, based on the presence or absence of (or a certain amount or frequency of) expected utterance types. Supervisors may be alerted only where a session appears to diverge significantly from expected performance (i.e. where the therapy session meets a predetermined criterion). If the supervisor is thus alerted they may take one or more further action such as more closely monitoring the therapist, advising/supporting the therapist in making improvements, or re-allocating the patient to a different (more suitable) therapist where the therapist performance is particularly poor quality. The particular one or more action may be automatically recommended to the supervisor based on the representation of the therapy session meeting a certain predetermined criterion. For example, if the system detects that a therapist is otherwise performing well but is failing to use (enough of) a particular utterance category, the system may alert the supervisor that the likelihood of clinical improvement is below average (i.e. the quality of the therapy provided is low) and that the supervisor should recommend to the therapist that more/more frequent utterances of that type should be delivered. Thereby the system provides automated QA and therapy supervision support.

Alternatively/additionally, the method and system can be used to detect the amount of therapy being delivered in a particular therapy session. For example, if the session booked is 60 minutes long, but the therapist starts the session late or finishes it early, the patient may not receive the full time allocation of therapy, and therefore the 'dose' of therapy delivered may be less than that recommended. A therapist who consistently under-delivers therapy time could be awarded a lower quality score by the system.

The utterance assignment model is used to provide automated feedback on therapist performance to an entity other than the therapist, for example the therapist's supervisor, the therapist's employer, a therapy service, a healthcare provider or a health insurance company, in order that one or more appropriate actions or interventions may be taken by that entity. This can be considered a type of automated quality assurance. The automated quality assurance may be provided regarding one or more therapy sessions delivered by a particular therapist.

The automated quality assurance is provided either after a particular therapy session has been completed, or alternatively/additionally whilst the therapy session is still taking place (real-time or live automated quality assurance). The automated quality assurance may be provided for all therapy sessions delivered by a particular therapist to a particular patient, in order that changes in the quality of therapy delivered to that patient over time can easily be identified, and one or more appropriate actions or interventions can be taken. Alternatively, the automated quality assurance may be provided for a subset of therapy sessions delivered by a therapist to a particular patient. This subset of therapy sessions may for example be chosen by the supervisor (e.g. the first and every alternate session), or may be randomly selected as part of the automated quality assurance. Alternatively, the automated quality assurance may be provided for a subset of all therapy sessions (e.g. a random sample of therapy sessions) provided by a particular therapist to all of their patients. Alternatively, all therapy session delivered by a particular therapist may be monitored by automated QA (analysis of a therapist's overall performance).

The automated QA may take into account the characteristics of a particular therapy session. For example, by using the current therapy (e.g. CBT) clinical knowledge, session plans can be prepared automatically ahead of each session according to the patient's presenting condition and the chosen treatment model. The session may be analysed using the system or method, and an alert may be generated if the session appears to diverge from the recommended plan.

The actions or interventions that may be taken by the entity (the therapist's supervisor, employer, therapy service, healthcare provider or health insurance company) in response to the automated quality assurance may include providing advice, support or education to the therapist in order that the therapist may improve the quality of the therapy provided, e.g. the identification of areas of potential improvement to be worked on during 1-1 supervision. For example a therapist may consistently be failing to check for risk, or only give out homework in a small fraction of sessions, or only give out generic and less helpful homework, such as psycho-education. Alternatively the action or intervention may include reallocating the patient to another therapist of greater experience or increased quality of therapy delivery. In these ways, the quality of care delivered to the patient is increased and therefore the likelihood of the patient improving or recovering is also increased.

By automating the QA, it is possible to provide QA on a greater number of therapy sessions at much reduced cost, thereby introducing the possibility of conducting QA on all therapy sessions. This is beneficial to patients (who are more likely to recover), therapists (who develop their professional expertise) and supervisors (who may therefore focus their expertise where it is most needed.)

Automated Auditing

An additional/alternative action that may be taken by the system at step S5 of the method is to initiate automated auditing of a therapy service. This involves the automatic collection of a plurality of outputs (output predictions) of the method and associated data relating to one or more therapy sessions/one or more therapists, in order that a therapy auditing process may be undertaken by e.g. a therapy service, a health insurance company, an employer, other payer of multiple instances of therapy, a health institution or a state or government body. The plurality of outputs (output predictions) may be anonymised with respect to the patients and/or the therapists. The automated audit may be used to compare e.g. therapy outcomes between different therapists or at different timepoints Automated Output Report An additional/alternative action that may be taken by the system at step S5 of the method is to initiate automated reporting of the output prediction of the method. The output report may be provided to the therapist, a supervisor of the therapist, a service to which the therapist belongs and/or the payer for the therapy for example an employer, health service or health insurer. The output of the method is a prediction of a characteristic of the therapist, the therapy, and/or the one or more patient, therefore following automated report of the output relating to one or more therapy session the therapist, the supervisor of the therapist, the service to which the therapist belongs and/or the payer for the therapy may take further actions appropriate to that prediction.

Automated Medical Diagnosis

An additional/alternative action that may be taken by the system at step S5 of the method is to provide automated medical diagnosis. The medical diagnosis relates to the one or more patient taking part in the therapy session. The medical diagnosis may be provided to the therapist, a supervisor of the therapist, a service to which the therapist belongs and/or the payer for the therapy for example an employer, health service or health insurer. The medical diagnosis comprises providing a prediction of the presence of a mental health disorder in the one or more patient, wholly or in part based on analysis of the patient utterances. Additional further actions may be taken by the system subsequent to provision of the medical diagnosis, such as recommendation of a particular therapy protocol to the therapist. In that way, the therapy delivered to the patient, and therefore the likely outcome for the patient, may be improved.

Automated Data Collection

An additional/alternative action that may be taken by the system at step S5 of the method is to perform automated data collection. This involves the automatic collection of data from any stage of the method including the session transcript (text data), the utterances, the assigned utterances, the optional additional inputs (non-content related session features and/or patient variables) and/or the representation. The data may be collected and stored by the system using any suitable method. The data collected can be used at a later stage to conduct research, further therapy product development, or kept for regulatory, quality assurance or auditing purposes.

EXAMPLES

Example 1

The one-to-one component of IECBT therapy sessions (i.e. patient-therapist interactions) was provided as text transcripts (text data). Within each transcript, individual parts of the text were automatically nominated as utterances, and were identified as originating from either the therapist or the patient, based on the individual text-based messages sent from either the therapist interface or the patient interface during the therapy session. Therefore the transcript of the therapy sessions was divided into therapist utterances and patient utterances, also retained information regarding the relative positions of the utterances in the therapy session.

The next stage of the process was to design suitable semantic representations. In this example the semantic representations used were tags, a set of tags was designed to classify therapist and user/patient utterances. These tag-sets had to satisfy multiple requirements; they needed to:

Be unambiguous, such that multiple human annotators would agree in most cases how to classify a certain utterance;

Be simple, such that a reasonably sophisticated computer system would be able to automatically assign tags to utterances with a useful level of accuracy;

Be as complete as possible (within the bounds of the simplicity constraint), so as to maximise the amount of insights uncovered;

Include sufficient domain knowledge, such that useful insights can be derived from the tags associated with the utterances in a therapy session.

Following consultation between domain experts in clinical psychology and natural language processing, and multiple iterations of manual tagging exercises, the set of tags presented in Table 1 were arrived at. Other numbers and sets of tags may be determined to be suitable in other circumstances.

TABLE 1

Tag set/utterance types

| | Tags used for the content of therapist utterances (Therapist Utterance Categories) |
|---|---|
| 1. | Greeting |
| 2. | Mood check |
| 3. | Obtain update |
| 4. | Bridge from previous session |
| 5. | Review previous homework |
| 6. | Agenda setting |
| 7. | Implementing change mechanisms |
| 8. | Summarising session |
| 9. | Eliciting feedback |
| 10. | Setting homework |
| 11. | Risk check |
| 12. | Set goals |
| 13. | Discuss perceptions of change |
| 14. | Planning for the future |
| 15. | Formulation |
| 16. | Giving feedback |
| 17. | Arrange next session |
| 18. | Goodbyes |
| 19. | Other |
| | Tags used for the style of therapist communication (Therapist Communication Style) |
| 20. | Therapeutic alliance |
| 21. | Collaboration |
| 22. | Socratic questioning |
| | Tags used for the content of user/patient utterances (User/Patient Utterance Categories) |
| 23. | Compliance |
| 24. | Non-compliance |
| 25. | Follow/neutral |
| 26. | Offer Information |
| 27. | Other |

Some of the categories are further exemplified in Table 2 below:

TABLE 2

Therapist utterance examples

| Therapist Utterance Category | Description | Example |
|---|---|---|
| 1. Greeting | An initial greeting to welcome the patient to the session. | "Good morning . . . " |
| 5. Review previous homework | Reviewing and discussing patient's previous homework assignment. | "Did you manage to use that mood chart I sent you last week?" |

TABLE 2-continued

Therapist utterance examples

| Therapist Utterance Category | Description | Example |
|---|---|---|
| 6. Agenda setting | Deciding and prioritizing the topic(s) to discuss during the therapy session. | "What issues shall we focus on today?" |
| 13. Discuss perceptions of change | Discuss what the patient feels they have learnt from therapy. | "What do you feel has helped you most during our time together?" |
| 15. Formulation | Framing patient's issues within the context of a CBT formulation. | "How do you think avoidance fits into the diagram we started in session 2?" |
| 17. Arrange next session | Arranging time and date of next appointment. | "Would you like to book another appointment for 10.00 am next Thursday?" |

Once the tag sets were defined, the next stage was the production of a dataset comprising therapy session transcripts with all utterances manually tagged. In the first instance, as a feasibility test, a small number of therapy sessions were annotated in order to test the approach.

For comparison with previously available methods, regular expressions (regexes) were handcrafted to identify the 19 categories/tags used for the content of therapist utterances, and 3 categories/tags used for the style of therapist communication. Regexes are a simple approach for tagging natural language text, and have previously been used to categorize the utterances in the standard 60 minute therapy sessions available to date. Regexes are rules for identifying runs of text that satisfy specified structural constraints. Regexes are considered to be very precise (i.e. they do not make many false positive mistakes), but they suffer from low recall (i.e. they miss things, that is make false negative mistakes).

As an example, the 'Socratic Questioning' style of communication could be represented by a regex:

((what|why|how) do you think)|(how (did|does) that make you)

Of the data from 97,263 sessions previously analysed, 69,342 utterances were found to match the above Socratic questioning regex.

A set of RegExes was produced for the classes of therapist utterance of interest, and used to estimate the feasibility of the proposed approach of correlating insights about the contents of therapy sessions and clinical outcomes. RegExes provided sufficient insight to identify some correlations, which provided the motivation to build more elaborate deep learning models for text tagging.

The utterance classification model developed uses recurrent neural networks (RNNs), with a two-level hierarchical structure: at the lower level, bi-directional RNNs are used to produce a representation of each utterance, while a higher level RNN is used to model each utterance in the context of the therapy session. The representation generated by the high level RNN was used as input to a multi-class multi-label classifier that emits likelihoods of each utterance belonging to each of the utterance classes present in the tag set.

Initial training of the deep learning utterance classification RNN model used 80 therapy session transcripts, while 20 were kept back for evaluating the accuracy of the model. The allocation of each utterance to a category by the model (to produce tagged utterances) was assessed using the F1 metric, which combines precision (positive predictive value) and recall (sensitivity) in a single number. Following initial training, as expected the deep learning model had significantly better recall than the RegEx system and the classification model already outperformed the regex approach (FIG. 9).

Example 2

For a subsequent expanded test using transcripts of 170 therapy sessions, only the therapist utterances (totalling 6698 individual utterances) were included.

The transcript data from 150 of the 170 hours of therapy sessions were used to train a deep learning utterance classification model, while the remaining 20 hour session transcripts were kept back for evaluating the accuracy of the model. The evaluation results are presented in FIG. 10, and indicate that the approach is feasible. The performance for each category was again measured using the F1 metric. As can be seen, even from a small amount of training data, many categories achieve F1 values of over 60%.

To confirm the results of the feasibility test, the overall F1 (macro-averaged) was also measured as a function of the number of session transcripts used as training data. As can be seen from FIGS. 11a and 11b, the accuracy of the utterance tagger continues to improve as more training data becomes available. Furthermore, the performance of the utterance classification model can again be seen to improve on the Regex approach (FIG. 11b). The improvement of the utterance classification model as a function of amount of training data suggests that, as expected, continual improvement of the model may be achieved by tagging the utterances from more therapy sessions.

Example 3

The resulting automatic utterance categorisation model was then used to tag a large number of therapy session transcripts (around 20,000). The relative frequency of each different therapist utterance type allocated by the model or a human annotator was plotted, as shown in FIG. 12. As can be seen, utterances in the 'change mechanisms' category, which constitute the active ingredient in cognitive behavioural therapy, made up the largest part of therapist utterances during the therapy sessions analysed using the model.

Example 4

As a further test, it was considered whether any features of the therapy sessions (session features, Table 3) and/or patient variables (Table 4) could be correlated with treatment outcome (% likelihood of patient recovery) for the data analysed for patients with known outcomes, and thereby be useful in prediction of recovery for future patients/users. Session features were categorised as 'non-content related' or 'content related' features (Table 3), where content-related features relate to tagged utterances, and the numbering of content related features matches that given for utterance categories in Table 1.

TABLE 3

Features of therapy sessions

| Non-content related features | Content related features E.g. Number, proportion or frequency of the following utterance categories: |
|---|---|
| Number of patient utterances | Greeting (1) |
| Number of therapist utterances | Mood check (2) |
| Number of patient words | Obtain update (3) |
| Number of therapist words | Bridge from previous session (4) |
| Number of patient characters | Review previous homework (5) |
| Number of therapist characters | Agenda setting (6) |
| Number of word types of patient | Implementing change mechanisms (7) |
| Number of word types of therapist | Summarizing session (8) |
| Number of turns taken in conversation | Eliciting feedback (9) |
| Time to first response for patient | Setting homework (10) |
| Time taken responding for patient (and therapist) | Risk check (11) |
| | Set goals (12) |
| Time of day of therapy session | Discuss perceptions of change (13) |
| Day of week of therapy | Planning for the future (14) |
| Duration of session | Formulation (15) |
| | Giving feedback (16) |
| | Arrange next session (17) |
| | Goodbyes (18) |
| | Therapeutic alliance (20) (e.g. "thanks for sharing") |
| | Collaboration (21) |
| | Socratic questioning (22) (e.g. "how does that make you") |

TABLE 4

Patient variables

| Patient variables | Input |
|---|---|
| Age of patient | Number of years |
| Gender of patient | M/F/Not known/Not disclosed |
| Starting PHQ score | 0-27 |
| Starting GAD score | 0-21 |
| Long-term health conditions | Y/N |
| Total number of therapy sessions completed by the patient | Number of sessions |

Using a logistic regression model of therapy outcome, certain content-related session features, non-content related session features and patient variables were found to positively correlate with patient recovery (Table 5). All transcripts for a single case (patient) were pooled and the average number of session features was obtained for that case. The values of each session feature were entered into a logistic regression with treatment outcome (whether the patient recovered) as a binary outcome. Regarding content-related session features (relating to tagged utterances), both the absolute number, and the percentage of all utterances that were of a certain category, were modelled. The former produced stronger correlations for the utterance categories analysed.

TABLE 5

Session features/patient variables that showed a positive relationship with clinical improvement (utterance category/style numbering matches that in Table 1)

| | Session features | | Patient variables |
|---|---|---|---|
| Content-related | Therapist utterance categories | (7) '(Implementing) change mechanisms'*** (13) 'Discussing perceptions of change'*** (3) 'Obtain update'** (6) 'Agenda setting'* (9) 'Eliciting feedback* (18) 'Goodbyes'* | Age of patient*** Total number of sessions*** Start GAD score*** |
| | Therapist communication style | (20) Therapeutic alliance*** (22) Socratic questioning*** | |
| Non-content-related | Number of sessions*** | | |

Significance:
***<0.001
**0.01
*<0.05
13,315 cases (engaged, at caseness, 2013-2018).

Therefore it can be seen that the presence of any one of 8 content-related session features (6 categories of therapist utterance, 2 therapist communication styles), one non-content related session feature, or 2 patient variables positively correlated with clinical improvement. The positive correlation between certain categories of therapist utterance and patient outcome is further quantified in FIG. 13a ('Agenda Setting'), FIG. 13b ('Change Mechanisms'), and FIG. 13c ('Eliciting Feedback') wherein in each case, increasing amounts of utterances of the given category correlate with a significant increase in the clinical improvement. In FIG. 13, the dashed horizontal line indicates the average improvement rate, i.e. the percentage of all cases that improve during treatment.

Positive correlations were also found between the therapist communication styles 'Therapeutic Alliance' and 'Socratic Questioning' and clinical improvement. It was also found that the total number of therapist utterances correlated positively with patient improvement.

Furthermore, using the same logistic regression model of therapy outcome, certain session features and patient variables were found to negatively correlate with clinical improvement (Table 6).

TABLE 6

Session features/patient variables that showed a negative relationship with improvement (utterance/style category numbering matches that in Table 1).

| | Session features | | Patient variables |
|---|---|---|---|
| Content-related | Therapist utterance categories | (11) Risk Check*** (4) Bridge* (21) Collaboration** | Long Term Conditions*** |
| Non-content related | | Number of therapist utterances*** Session duration*** | |

Significance:
***<0.001
**0.01
*<0.05
13,315 cases (engaged, at caseness, 2013-2018).

Figure 13A:
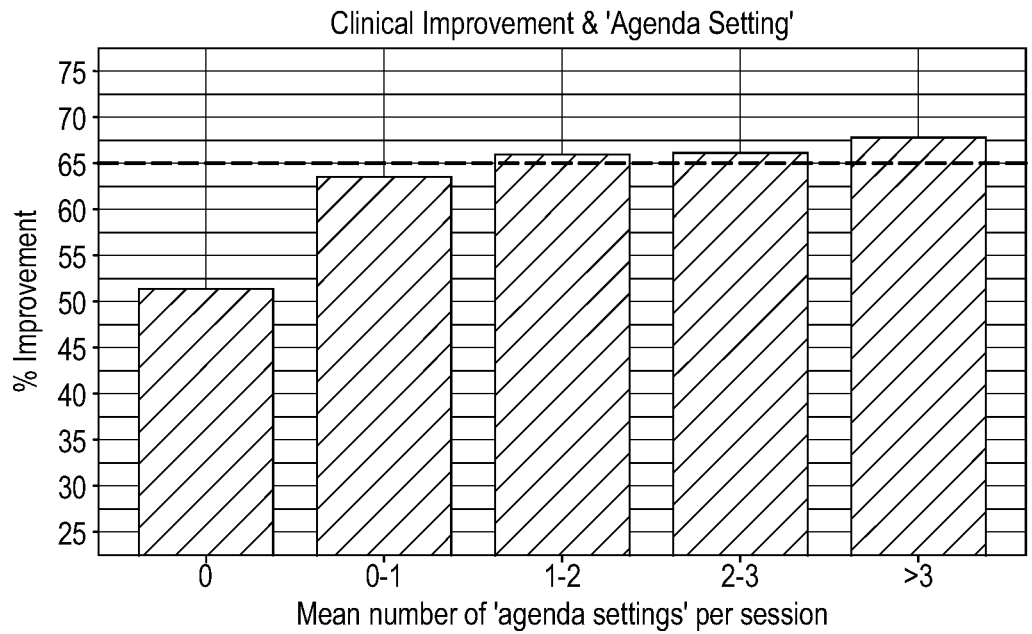
Figure 13B:
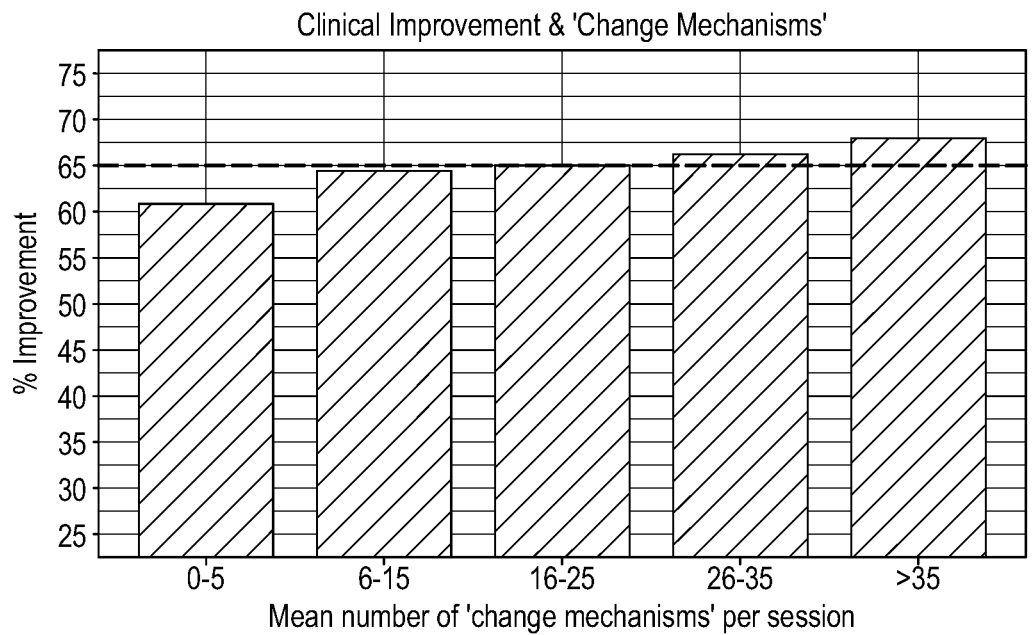
Figure 13C:
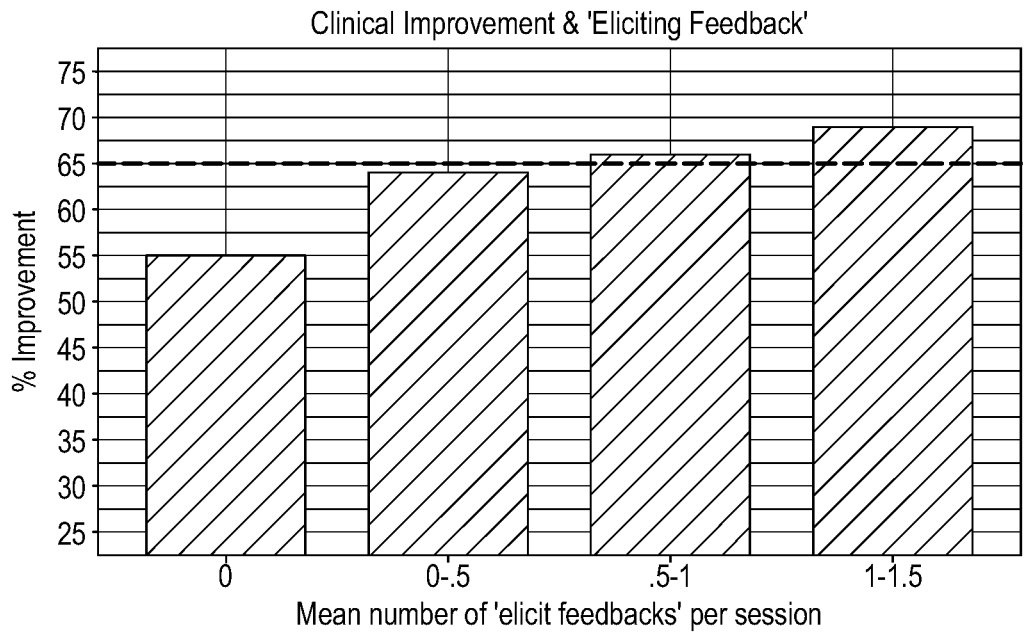
Figure 13D:
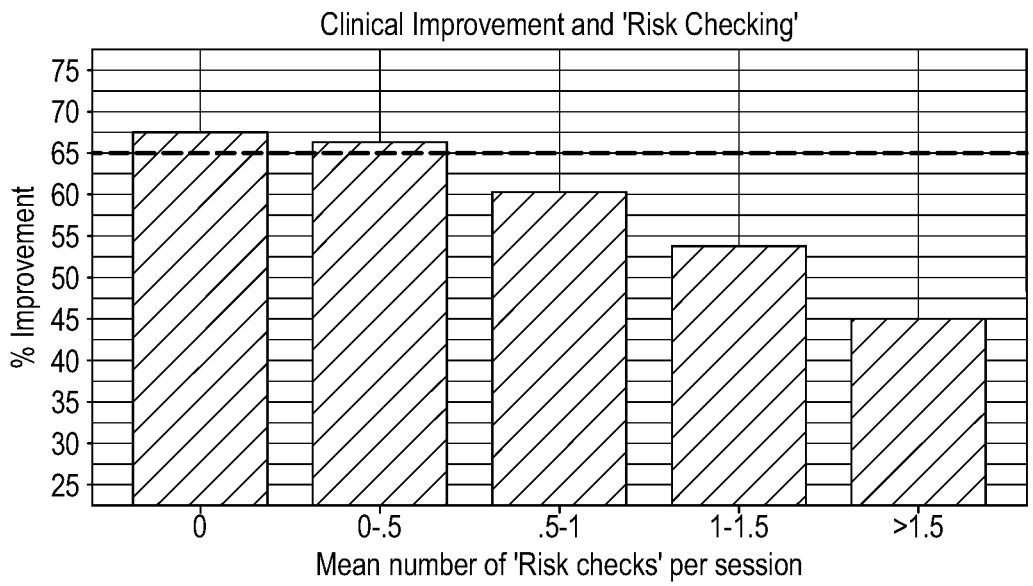

Therefore two content-related session features (both were therapist utterance categories) were identified that appear negatively correlated with clinical improvement (Table 6). As illustrated in FIG. 13d for the category 'Risk check', it can be seen that an increasing proportion of 'Risk check' utterances was associated with decreasing clinical improvement.

Example 5

Due to the large number of utterances that are categorised by the model as belonging to the category 7 'Implementing change mechanisms', and in order to gain even deeper insights into the therapy process, the tagging/categorisation schema has been refined by defining a hierarchy of sub-categories within that category. Two extra levels of sub-hierarchy are shown in Table 7. Category 7 has been divided into 5 first level sub-categories (7.1-7.5), each of which has then been further sub-divided.

TABLE 7

Further levels of 'Implementing change mechanisms' categorisation 7.1 Cognitive reattribution
7.1.1. Worry thought record
7.1.2. Suppression experiments
7.1.3. Challenging meta-worry
7.1.4. Questioning the evidence
7.1.5. Questioning the mechanism
7.1.6. Questioning uncontrollability
7.1.7. Enhancing cognitive dissonance
7.1.8. Controlled worry periods
7.1.9. Cognitive restructuring (diary/thought record)
7.1.10. Cognitive restructuring (guided imagery)
7.1.11. Re-evaluation of positive beliefs about worries
7.1.12. Learning to let go of worries
7.1.13. Guided discovery
7.1.14. Elicit, record and manage negative automatic thoughts
7.1.15. Elicit values/or core beliefs
7.1.16. Identify beliefs and misinterpretations
7.1.17. Behavioural experiments
7.1.18. Surveys
7.1.19. Updating trauma memory
7.1.20. Impact statement
7.1.21. Identification of meaning and stuck points
7.1.22. Reliving
7.1.23. Identifying hot spots and meanings
7.1.24. Using feedback
7.1.25. Rescripting early memories
7.1.26. Manipulation of self-focussed attention and safety behaviours
7.1.27. Attention training
7.1.28. Controlled worry periods
7.1.29. Learning to let go of worries
7.1.30. Suppression experiments
7.1.31. Cost benefit analysis
7.2. Behavioural reattribution
7.2.1. Exposure
7.2.2. Worry behaviours
7.2.3. Activity scheduling
7.2.4. Functional analysis
7.2.5. Action plans
7.2.6. Identifying safety behaviour
7.2.7. Explore avoidance
7.2.8. Revisiting site of trauma
7.2.9. Graded hierarchy
7.3. Conceptualisation
7.3.1. Recognising pleasant outcomes from uncertain situations
7.3.2. Cross sectional, longitudinal or disorder specific formulation
7.3.3. Establish links between physical symptoms and thoughts emotions and behaviours
7.4. Skill Teaching
7.4.1. Relaxation
7.4.2. Problem solving training
7.4.3. Breathing retraining TABLE 7-continued Further levels of 'Implementing change mechanisms' categorisation 7.4.4. Progressive muscular relaxation training
7.4.5. Synthesizing learning
7.4.6. Guided self-dialogue
7.4.7. Reclaiming your life
7.4.8. Ritual prevention
7.4.9. Mindfulness
7.5. Psychoeducation
7.5.1. Normalizing
7.5.2. Synthesizing and consolidating learning
7.5.3. Psychophysiology
7.5.4. Socialise to the CBT model
7.5.5. General information
7.5.6. Treatment rationalization
7.5.7. Synthesizing and consolidating learning The sub-categories are used to re-tag the therapy session transcripts and retrain the RNN model (HiBiLSTM therapy insights model), in order to provide more detailed information on the key aspects of good (high quality) therapy and improve the precision of the methods of the invention. By using the deep learning model (HiBiLSTM therapy insights model) to perform large-scale analysis of therapy sessions and sub-classify (assign) certain categories of utterance e.g. 'change mechanisms', it is possible to identify which particular change mechanisms are most effective. By performing the analysis on therapy data relating to a particular group of patients, it is possible to identify which particular change mechanisms work best for those patients, e.g. young female patients presenting with anxiety, or older males presenting with depression and a co-morbid long term physical condition. Based on this insight, more personalised treatment plans are automatically produced for each patient. For example, whichever of the possible change mechanisms should be used for each patient is recommended, by optimising for various clinical measures such as likelihood of recovery, likelihood of improvement, or engagement.

Example 6

A method was developed to quantify therapy using a deep-learning approach to automatically assign a semantic representation (meaning) to therapist utterances by categorization. Categories may also be termed features. Approximately 90,000 hours of internet-enabled CBT was collected. Using logistic regression, the relationship between the quantity of 24 features of a therapy session and clinical outcomes was examined. After controlling for patient variables, factors common to most psychotherapies as well as factors specific to CBT (e.g. the use of change mechanisms) were found to be associated with increased odds of reliable improvement in patient symptoms. This work provides the first demonstration that clinical outcomes in psychotherapy are predictable based on individual session utterances and represents a new systematic approach for quality controlled treatment of mental illness.

Materials and Methods

Experimental Design

All data were obtained from patients receiving IECBT for the treatment of a mental health disorder, between June 2012 and March 2018. IECBT was delivered using a commercial package, originally developed for and currently used in the English National Health Service, provided by Ieso Digital Health (http://uk.iesohealth.com), following internationally recognised standards for information security (ISO 27001; https://www.iesohealth.conn/en-gb/legal/iso-certificates).

NICE approved disorder specific CBT treatment protocols, based on Roth and Pilling's CBT competences framework, were delivered in a secure online therapy room via instant synchronous messaging, by a qualified CBT therapist accredited by the British Association for Behavioural & Cognitive Psychotherapies (BABCP) (a realistic example of a therapy conversation can be seen in FIG. 14). Patients self-referred or were referred by a primary healthcare worker directly to the service. All patients who referred to the service and were suitable (over 18 years old, registered with a GP and not at significant risk of suicide) were offered treatment. Each treatment session was scheduled for a duration of one hour.

The Improving Access to Psychological Therapies (IAPT) programme is a large-scale initiative aimed at increasing access to evidence-based psychological therapy for common mental health disorders within the English National Health Service, whilst controlling costs. IAPT adopts a stepped care approach where patients are offered different psychological therapies based on illness severity. Only patients receiving step 3 treatment (moderate to severe symptoms) were included. The information captured through IAPT's minimum dataset, including IECBT, is intended to support monitoring of implementation and effectiveness of national policy/legislation, policy development, performance analysis and benchmarking, national analysis and statistics, and national audit of IAPT services. At registration patients agree to the services' terms and conditions, including use of anonymized data for audit purposes and to support research, including academic publications or conference presentations.

Therapy Utterance Categories

A total of 24 therapy feature categories (see Table 8) were defined based on the structure and components of the standard CBT protocol, informed by the CBT competences framework and the Revised Cognitive Therapy Scale (CTS-R). All specific change methods (cognitive reattribution, behavioural reattribution, skill-teaching, conceptualization, and psychoeducation etc.) were included under a single category labelled 'Change Mechanisms'. A research psychologist annotated 290 hours of therapy (11,221 utterances) under the guidance of a qualified clinical therapist, and was blind as to the outcome of each case. Each therapist utterance was tagged with one (or more) of 19 categories; five additional categories (collaboration, Socratic questioning, and three pertaining to therapeutic alliance: therapeutic thanks, therapeutic reinforcement and therapeutic empathy) were tagged using regular expressions (regexes), thereby totaling 24 Therapy Feature Categories.

A list of all the therapy feature categories used in the annotation effort are shown in Table 8 with descriptions and examples of each category provided in Table 9. A realistic example of a therapy session is shown in FIG. 14.

TABLE 8

Feature (utterance) categories used in transcript annotation.
Therapy Feature Categories

| | |
|---|---|
| Hello | Planning for the Future |
| Mood Check | Elicit Feedback |
| Obtain Update | Summarise Session |
| Bridge | Give Feedback |
| Risk Check | Arrange next Session |
| Set Agenda | Goodbye |
| Review Homework | *Socratic Questioning |
| Set Goals | *Therapeutic Thanks |
| Formulation | *Therapeutic Empathy |
| Change Mechanisms | *Therapeutic Praise |
| Perceptions of Change | *Collaboration |
| Setting Homework | Other |

*Features tagged using regularexpressions.

TABLE 9

Feature categories used in transcript annotation. Description and examples of all feature categories used in utterance tagging.

| Category | Description | Example |
|---|---|---|
| Hello | An initial greeting welcoming the patient to the session. | "Good morning" |
| Mood Check | Assessing the patient's mood. | "How are you feeling?" |
| Obtain Update | Determining if there have been any changes/issues that have arisen since the last session. | "How have things been since we last spoke?" |
| Bridge | Briefly summarising the most important issues covered in the previous session. | "So, in the last session we talked about . . . " |
| Risk Check | Assessing if patient is at risk of suicide/self-harm. | "I see from your questionnaire that you are having some thoughts of self-harm - is that correct?" |
| Set Agenda | Deciding and prioritizing the topic(s) to discuss during the therapy session. | "What issues would you like us to focus in today's session?" |
| Review Homework | Reviewing and discussing patient's previous homework assignment. | "Did you manage to complete the thought diary I sent you last week?" |
| Set Goals | Setting patient's long-term goals for therapy. | "What would you like to set as your goals from therapy?" |
| Formulation | Framing patient's issues within the context of a CBT formulation. | "With regard to the diagram we started last week - how do you think your feelings influence your avoidance behavior?" |
| Give Feedback | Briefly summarising what the patient has said/feedback based on previous utterances. | "It sounds like you've been under a lot of stress at work and you feel this is having an effect on your relationship" |
| Change Mechanisms | Cognitive and behavioural strategies employed by the therapist designed to promote therapeutic change. | "What is the evidence that makes you think this belief is true?" |

TABLE 9-continued

Feature categories used in transcript annotation. Description and examples of all feature categories used in utterance tagging.

| Category | Description | Example |
|---|---|---|
| Perceptions of Change | Discuss what patients feel they have learnt from therapy. | "What do you feel has helped you most during our time together?" |
| Set Homework | Setting a homework task for the patient. | "I'd like you to keep a diary of anxious predictions for homework" |
| Planning for the Future | Asking the patient how they plan to deal with future issues following completion of therapy. | "What do you think you can continue to do to prevent a future setback?" |
| Elicit Feedback | The therapist asks the patient for feedback on session/additional questions. | "How have you found today's session?" |
| Summarise Session | A final summary of the day's session focusing on the most important aspects of the discussion. | "So, in today's session we talked about . . . " |
| Arrange next Session | Arranging time and date of next appointment. | "Would you like to book another appointment for 10.00am next Thursday?" |
| Goodbye | Saying goodbye at the end of the session. | "Bye for now, and have a good week" |
| *Socratic Questioning | Questions used to uncover the assumptions and evidence that underpin people's thoughts | "Why did that make you feel angry? |
| *Therapeutic Thanks | Therapist shows gratitude to patient | "Thanks for sharing" "Thank you for completing . . . " |
| *Therapeutic Empathy | Therapists empathises with patient | "I'm sorry to hear that" "That must have been awful" |
| *Therapeutic Praise | Therapist praises patient | "Well done" "That's great" |
| *Collaboration | Examples of collaborative processes between therapist and patient | "Why don't we decide on that together?" |
| Other | Miscellaneous utterances not covered by the above categories. | "Have you been to see the GP about your cough?" |

*Tagged using regular expressions (regexes).

Therapy Insights Model

A deep learning model was developed to automatically classify each utterance into one or more of the 24 categories. Firstly, word2vec (T. Mikolov, I. Sutskever, K. Chen, G. Corrado, J. Dean, Distributed Representations of Words and Phrases and their Compositionality. Adv. Neural Inf. Process. Syst. 26, 3111-3119 (2013) was used on a preprocessed version of the entire data set of over 90,000 hours of therapy session transcripts (approx. 200M words) to learn word embeddings that are suited to the domain of psychotherapy. The data was preprocessed by tokenizing according to whitespace and punctuation and then by lower-casing all tokens (punctuation symbols were kept as separate tokens). This resulted in a vocabulary of 89,260 words, each represented as a continuous dense vector of length 200.

Each utterance was modelled in a transcript as a sequence of word embeddings and fed into a bidirectional long short-term memory (BiLSTM). Max-pooling over the hidden states of the BiLSTM was used to encode each utterance as a fixed-length vector. In order to model each utterance in the context of the entire transcript, each of the fixed-length utterance representations in a transcript was fed into another BiLSTM and the hidden state at each time-step was used to feed into the final output layer. For both of the BiLSTM stages, a hidden dimension of 400 and dropout of 0.5 was used. The output layer mapped each fixed length utterance-in-context representation into a vector of length 23 (23 classes, with the 'Other' class modelled as all zeros) and used a sigmoid activation function on the output. Conceptually, each category was modelled as a binary classifier.

Using the annotated data, a deep learning model was trained using 8,859 utterances from 230 therapy sessions. The use of a neural network that uses a long short-term memory (LSTM) unit over the word embeddings in each utterance, and over the utterances in each transcript, enabled the model to use contextual cues in the overall transcript when classifying any particular utterance (e.g. setting an agenda is more likely to occur early in a session).

The training labels were obtained from manual annotation for 19 of the categories, and from high-precision regular expression (regex) for the remaining five categories.

After training the deep learning model on 230 transcripts, another 30 transcripts were used to tune hyperparameters (i.e. embedding length, hidden dimension size, dropout probability, and choice of pooling) and the remaining 30 transcripts were used to report the test results (see Table 10, Results).

Clinical Outcomes

Clinical outcomes were measured in terms of reliable improvement and IAPT-engagement, and were included as binary measures (i.e. 0 or 1). Following IAPT guidelines, a patient was classed as engaged if they attended two or more treatment sessions. Reliable improvement was calculated based on two severity measures: PHQ-9 and GAD-7, corresponding to depressive and anxiety symptoms respectively. Both measures were completed by the patient at initial assessment and before every therapy session. The PHQ-9 is a 9-item measure designed to facilitate screening and severity assessment of depression. According to IAPT, a patient scoring 10 or more in the PHQ-9 (range 0-27) is considered to be suffering from clinically significant depressive symptoms. A reduction of 6 points or more on the PHQ-9 scale between two time points is indicative of statistically reliable improvement in symptom severity. The GAD-7 is a 7-item screening and severity measure for generalised anxiety disorder. According to IAPT, a patient scoring 8 or more in the GAD-7 (range 0-21) is considered to be suffering from clinically significant anxiety symptoms. A reduction of 4 points or more on the GAD-7 scale between two time points is indicative of statistically reliable improvement in symptom severity. If a patient scored 10 or above for PHQ-9 and/or 8 or above for GAD-7 they were classed as meeting the clinical threshold at assessment.

Reliable improvement was used as an outcome metric as it measures whether or not a reduction in severity is statistically reliable, regardless of clinical threshold. Conversely, recovery is based on a patient going below the clinical threshold for both PHQ-9 and GAD-7, therefore patients whose initial scores are closer to that threshold have higher chances of recovery. In addition, recovery does not take into account whether the observed reduction in severity is greater than the measurement error of the scales. Other symptom severity measures were not examined as only PHQ-9 and GAD-7 are mandatorily collected within the IAPT framework.

For IAPT-engaged patients, the difference between scores at initial assessment and last treatment session for PHQ-9 and GAD-7 was used to determine patients' improvement status. IAPT-engaged patients who showed a significant reduction in at least one of the outcome measures from assessment to the last treatment session, whilst not showing a significant increase in the other outcome measure, were classed as improved. Consistent with IAPT guidelines, outcomes measures were based on scores when patients were discharged from treatment, irrespective of whether they were coded by their therapist as having completed or dropped out of treatment.

Statistical Analysis

The quantity of each therapy feature was calculated based on the number of words in each utterance for that feature. The number of words per feature was deemed to be a more reliable measure of the quantity of a feature than the number of utterances. The mean number of words for each therapy feature across all sessions (excluding the final session) were calculated for each case (patient). The final treatment session was not included in the analysis as outcome measures are taken prior to the commencement of each treatment session, thus the content of the final session has no effect on outcome scores. The initial sample comprised a total of 90,934 session transcripts taken from 17,572 patients (cases).

All analyses were performed in R. A logistic regression analysis was performed to investigate the relationship between session features and reliable improvement. Predictor variables were the mean number of words for each therapy feature across sessions and patient demographics. Patient demographic variables were: starting symptom severity (starting PHQ-9 and GAD-7 scores), patient gender, patient age, whether or not the patient suffered from a long-term physical condition, and whether or not the patient was taking psychotropic medication (e.g. anti-depressants or anxiolytics) at the start of treatment. The number of sessions completed for that case and the mean duration of sessions were also included in the model. To account for sessions where the patient or therapist entered the session earlier or later than expected, if any session included a period of more than one hour without messages being exchanged then this period was subtracted from the final duration. Cases with missing start or end GAD-7 or PHQ-9 scores were removed from the analysis. Cases with an average of fewer than 50 patient words were not considered to constitute active therapy and were excluded from the analysis. A total of 13,073 patients at a clinical threshold and engaged in treatment were included in the analysis.

To investigate the relationship between first session features and outcomes, predictor variables were the number of words for each therapy feature in the first session, patient demographics and duration of first session. First sessions with fewer than 50 patient words were excluded from the analysis, leaving a total of 13,019 patients at a clinical threshold and engaged in treatment. To investigate the relationship between first session features and IAPT-engagement, predictor variables were the number of each therapy feature in the first session, patient demographics and duration of first session. A total of 14,899 patients at clinical threshold were included.

For all regression analyses, continuous predictor variables were scaled and centred to the mean. Statistical significance was defined as P<0.05 two-tailed, uncorrected. Multicollinearity analyses were performed to investigate potential correlations between predictor variable for all regression analyses. Variance inflation factors were smaller than two for all predictor variables, confirming that regression models were not affected by the presence of multicollinearity.

Results

Therapy Insights Model

Table 10 shows the performance of the Therapy Insights Model (TIM) in each of the 24 feature categories, for 30 therapy sessions that were not used during the training process.

TABLE 10

Therapy insights model test results. The positive predictive value (PPV), sensitivity, and specificity of the model on 30 therapy sessions which have not been used in the training process.

| Category | # of Positives | PPV (Precision) | Sensitivity (Recall) | Specificity |
|---|---|---|---|---|
| Hello | 28 | 100.00% | 100.00% | 100.00% |
| Mood check | 24 | 75.00% | 62.50% | 99.57% |
| Obtain update | 35 | 61.76% | 60.00% | 98.87% |
| Bridge | 12 | 53.85% | 58.33% | 99.49% |
| Risk Check | 15 | 90.00% | 60.00% | 99.91% |
| Set Agenda | 53 | 78.43% | 75.47% | 99.03% |
| Review Homework | 37 | 61.11% | 29.73% | 99.39% |
| Set Goals | 12 | 70.00% | 58.33% | 99.75% |
| Formulation | 44 | 64.51% | 68.18% | 98.34% |
| Give Feedback | 74 | 57.14% | 27.03% | 98.65% |
| Change Mechanisms | 428 | 73.58% | 63.79% | 87.12% |
| Perceptions of Change | 20 | 75.00% | 15.00% | 99.91% |
| Set Homework | 52 | 74.29% | 50.00% | 99.21% |
| Planning for the Future | 24 | 58.82% | 41.67% | 99.40% |
| Elicit Feedback | 42 | 69.70% | 54.76% | 99.13% |
| Summarise Session | 0 | n/a | n/a | 100.00% |
| Arrange next Session | 45 | 94.47% | 80.00% | 99.83% |
| Goodbye | 41 | 88.64% | 95.12% | 99.56% |
| Socratic Questioning | 23 | 76.92% | 43.48% | 99.74% |
| Therapeutic Thanks | 7 | 100.00% | 62.50% | 100.00% |
| Therapeutic Empathy | 15 | 84.62% | 73.33% | 99.83% |
| Therapeutic Praise | 40 | 97.50% | 97.50% | 99.91% |
| Collaboration | 29 | 100.00% | 93.10% | 100.00% |
| Other | 394 | 52.28% | 70.31% | 79.02% |

*No examples of "Summarise Session" occur in the evaluation data.

The trained model was used to automatically annotate all the therapy sessions in the dataset (~90,000 hours of therapy). Data were grouped by case, and the number of words for each therapy feature, averaged over all sessions (excluding the final session), were calculated for each case. This value was used as a measure of the 'dosage' of that feature (see materials and methods). The occurrence of features (% of sessions) and mean number of words per feature as identified by the trained model are shown in Tables 11, 12 and 13.

Predictors of Reliable Improvement

As IECBT is commissioned by the NHS under the IAPT programme, IAPT conventions were used for defining outcomes. Patients (cases) who showed a significant reduction in at least one of the outcome measures (i.e. decrease of 6 points or more in the PHQ-9 and/or 4 points or more in the GAD-7) between initial assessment and the last treatment session, whilst not showing a significant increase in the other outcome measure, were classed as showing statistically reliable improvement. As per IAPT convention, the metric of improvement can only be calculated for patients with two or more scores. All patients had attended two or more sessions, with PHQ-9 or GAD-7 scores above the clinical threshold (see materials and methods).

A logistic regression was performed to identify which features predicted reliable improvement in patient symptoms. FIG. 15 shows the standardized odds ratios for each session feature included in the analysis (see Table 11 for details). The results revealed a significant relationship between a number of features and reliable improvement. 'Therapeutic Praise', 'Planning for the Future', 'Perceptions of Change', 'Set Agenda', 'Elicit Feedback', 'Review Homework' and 'Give Feedback' were all positively associated with reliable improvement. 'Change Mechanisms'—a CBT-specific feature of therapy—was also positively related with improvement. By contrast, increases in 'non-therapy' related content ('Other', 'Hello' and 'Goodbye') were negatively related with improvement, as were 'Therapeutic Empathy', 'Risk Check' and 'Bridge'.

The total number of treatment sessions completed was positively related with improvement (patients completing more sessions were more likely to improve); by contrast, longer session durations were associated with lower rates of improvement. Severity of anxiety symptoms (start GAD-7 score), not being prescribed medication, and patient age were also positively related with improvement, while increased severity of depression symptoms (start PHQ-9 score) and the presence of a long-term medical condition were negatively related.

TABLE 11

(below)-Predictors of reliable improvement-all sessions.

| Feature | Mean no. of words (SD) | % of sessions | Odds Ratio | 95% CI | z-value | P-value |
|---|---|---|---|---|---|---|
| Hello | 12(22.7) | 99.6% | 0.92 | 0.88-0.96 | −3.57 | <.001*** |
| Mood Check | 5.6(7) | 97.9% | 0.99 | 0.95-1.03 | −0.34 | .73 |
| Obtain Update | 16.4(14.5) | 59.0% | 1.03 | 0.99-1.08 | 1.56 | .12 |
| Bridge | 12.2(17.9) | 27.9% | 0.95 | 0.91-0.98 | −2.76 | .006** |
| Risk Check | 13.6(31.5) | 21.0% | 0.85 | 0.81-0.89 | −7.54 | <.001*** |
| Set Agenda | 47.2(43.5) | 71.3% | 1.08 | 1.02-1.14 | 3.02 | .002** |
| Review Homework | 18.5(19.2) | 44.5% | 1.04 | 1.00-1.09 | 2.00 | .04* |
| Set Goals | 15.9(30.8) | 19.4% | 1.00 | 0.96-1.05 | 0.40 | .69 |
| Formulation | 30.3(63.9) | 18.2% | 0.96 | 0.92-1.00 | −1.89 | .06 |
| Give Feedback | 33.6(40) | 52.1% | 1.05 | 1.00-1.10 | 2.20 | .02* |
| Change Mechanisms | 477.1(236) | 97.9% | 1.11 | 1.06-1.17 | 4.37 | <.001*** |
| Perceptions of Change | 1.6(4.8) | 5.8% | 1.11 | 1.06-1.16 | 4.59 | <.001*** |
| Set Homework | 63.2(48.9) | 69.1% | 0.96 | 0.92-1.00 | −1.68 | .09 |
| Planning for future | 1.1(6) | 2.4% | 1.12 | 1.06-1.19 | 4.01 | <.001*** |
| Elicit Feedback | 15.3(16.4) | 55.3% | 1.06 | 1.02-1.11 | 2.82 | .004 ** |
| Summarise Session | 0.25(2.6) | 0.4% | 0.99 | 0.95-1.03 | −0.52 | .60 |
| Arrange next Session | 30(21.3) | 82.5% | 1.00 | 0.96-1.04 | 0.05 | .96 |
| Goodbye | 15.4(10.4) | 90.7% | 0.95 | 0.91-0.99 | −2.34 | .02* |
| Socratic Questioning | 24.1(31.1) | 47.4% | 1.02 | 0.98-1.06 | 0.95 | .34 |
| Therapeutic Thanks | 5.4(13.3) | 13.3% | 0.97 | 0.93-1.01 | −1.48 | .14 |
| Therapeutic Empathy | 21(31.3) | 38.0% | 0.84 | 0.81-0.88 | −8.21 | <.001*** |
| Therapeutic Praise | 30.6(39.4) | 52.6% | 1.21 | 1.15-1.27 | 7.18 | <.001*** |
| Collaboration | 41(45.9) | 61.9% | 0.97 | 0.93-1.02 | −1.09 | .27 |
| Other | 121.1(81) | 96.0% | 0.88 | 0.85-0.92 | −5.82 | <. 001 *** |

| Variable | Mean/ Prevalence (SD) | Odds Ratio | 95% CI | z-value | P-value |
|---|---|---|---|---|---|
| Total No. Sessions | 6.2(2.9) | 1.22 | 1.17-1.27 | 9.01 | <.001 |
| Session Duration (mins) | 62.4(7.5) | 0.95 | 0.91-0.99 | −2.34 | .02* |
| Start Phq9 | 14.7(5.4) | 0.95 | 0.91-0.99 | −2.41 | .03* |
| Start Gad7 | 8.3(5.7) | 1.29 | 1.23-1.34 | 11.8 | <.001*** |
| Patient Age | 34.8(12.0) | 1.16 | 1.12-1.22 | 7.47 | <.001*** |
| Patient Gender | | | | | |
| Female | 72.9% | | | | |
| Male | 26.7% | 0.96 | 0.88-1.05 | −0.89 | .50 |
| Unknown/Not Stated | 0.4% | 0.92 | 0.49-1.78 | −0.24 | .74 |
| Long Term Condition | | | | | |
| No | 46.4% | | | | |
| Yes | 27.8% | 0.72 | 0.66-0.80 | −6.55jp | <.001*** |
| Unknown/Not Stated | 25.8% | 0.78 | 0.71-0.86 | −5.08 | <.001*** |
| Psychotropic Medication | | | | | |
| Prescribed Not Taking | 8.6% | | | | |
| Not Prescribed | 45.7% | 1.23 | 1.06-1.41 | 2.84 | .004** |

TABLE 11-continued

| (below)-Predictors of reliable improvement-all sessions. | | | | | |
|---|---|---|---|---|---|
| Prescribed Taking | 42.3% | 0.98 | 0.84-1.13 | −0.27 | .78 |
| Unknown/Not Stated | 3.4% | 0.85 | 0.67-1.08 | −1.28 | .20 |

Output of logistic regression investigating relationship between reliable improvement and mean number of words per feature across treatment.
Standardized odds ratios indicate the effect of an increase of one standard deviation of a feature on the odds of improvement.
% of sessions indicates the percentage of the total number of sessions that contained utterances categorized as that feature.
Gender "Female", Long Term Conditions "No" and Psychotropic Medication "Prescribed Not Taking" were reference classes for the categorical variables.
*p < .001, p < .01, *p < .05.

First Treatment Session Predictors of Reliable Improvement

Due to the structured nature of CBT, the first and last sessions in an episode of care are likely to contain a different element mix compared to mid-episode sessions. For example, setting goals for therapy is an important part of CBT (23) and is more likely to occur in early in treatment. Similarly, early development of a therapeutic alliance is thought to be associated with good outcomes (24). To address this, we performed a logistic regression investigating the relationship between the quantity of each feature occurring in the first treatment session and reliable improvement for all patients above the clinical threshold and engaged with treatment.

FIG. 16 shows the standardized odds ratios for each session feature included in the analysis (see Table 12 for details). Again, we found that the quantity of 'Set Agenda', 'Therapeutic Praise' and 'Change Mechanisms' were positively associated with improvement. As predicted, goal setting in the first session was also positively related with improvement. Again, 'Non-therapy' related content ('Other') showed a negative relationship as did 'Therapeutic Empathy' and 'Risk Check'. Demographic variables of start GAD-7 score, not being prescribed medication, and patient age were all positively associated with improvement, while start PHQ-9 score and the presence of a long-term medical condition showed a negative relationship.

TABLE 12

| (below)-First session predictors of reliable improvement. | | | | | | |
|---|---|---|---|---|---|---|
| Feature | Mean no. of words (SD) | % of sessions | Odds Ratio | 95% CI | z-value | P-value |
| Hello | 14.5(34.6) | 99.7% | 0.94 | 0.90-0.98 | −2.95 | .003** |
| Mood Check | 5.4(10.4) | 1.21% | 1.00 | 0.96-1.04 | −0.21 | .83 |
| Obtain Update | 12.2(19.6) | 1.73% | 1.02 | 0.98-1.06 | 0.92 | .35 |
| Bridge | 9.6(24.7) | 0.61% | 1.01 | 0.97-1.05 | 0.53 | .59 |
| Risk Check | 22.4(53.8) | 1.81% | 0.92 | 0.89-0.96 | −4.15 | <.001*** |
| Set Agenda | 61.8(68.7) | 3.48% | 1.09 | 1.04-1.14 | 3.66 | <.001 |
| Review Homework | 15.4(27.5) | 1.44% | 1.03 | 0.99-1.07 | 1.27 | .20 |
| Set Goals | 28.3(57.8) | 2.22% | 1.05 | 1.01-1.10 | 2.47 | .01* |
| Formulation | 55.1(128) | 4.08% | 1.04 | 1.00-1.08 | 1.72 | .08 |
| Give Feedback | 34.1(58) | 1.86% | 1.02 | 0.98-1.06 | 0.97 | .33 |
| Change Mechanisms | 435.7(280) | 33.49% | 1.12 | 1.07-1.17 | 4.92 | <.001*** |
| Perceptions of Change | 1.1(7.3) | 0.09% | 0.98 | 0.95-1.02 | −0.79 | .42 |
| Set Homework | 77.5(74.3) | 4.05% | 1.03 | 0.99-1.07 | 1.24 | .21 |
| Planning for future | 0.43(6.6) | 0.03% | 0.99 | 0.96-1.04 | −0.09 | .92 |
| Elicit Feedback | 17.8(25.3) | 2.07% | 1.03 | 0.99-1.08 | 1.65 | .09 |
| Summarise Session | 0.26(4.8) | 0.01% | 1.00 | 0.96-1.04 | −0.22 | .82 |
| Arrange next Session | 33.9(32.7) | 4.01% | 1.02 | 0.98-1.06 | 0.77 | .44 |
| Goodbye | 16.4(15.7) | 2.84% | 0.98 | 0.94-1.02 | −0.93 | 0.35 |
| Socratic Questioning | 20.2(39.8) | 1.38% | 1.02 | 0.98-1.06 | 0.85 | .39 |
| Therapeutic Thanks | 8.8(24.8) | 0.49% | 1.02 | 0.98-1.06 | 0.75 | 0.45 |
| Therapeutic Empathy | 25.3(51.3) | 1.62% | 0.91 | 0.88-0.95 | −4.44 | <.001*** |
| Therapeutic Praise | 24(47.8) | 1.44% | 1.09 | 1.04-1.14 | 3.65 | <.001*** |
| Collaboration | 46(74) | 2.35% | 0.97 | 0.93-1.02 | −1.23 | .21 |
| Other | 138.7(114.7) | 21.75% | 0.94 | 0.90-0.97 | −3.26 | .001** |
| Variable | Mean/ Prevalence (SD) | | Odds Ratio | 95% CI | z-value | P-value |
| Session Duration (mins) | 63.5(9.3) | | 1.01 | 0.97-1.05 | 0.54 | .58 |
| Start Phq9 | 14.7(5.4) | | 0.90 | 0.86-0.94 | −4.82 | <.001*** |
| Start Gad7 | 8.3(5.7) | | 1.29 | 1.24-1.34 | 11.9 | <.001*** |
| Patient Age | 34.8(12.0) | | 1.17 | 1.12-1.21 | 7.58 | <.001*** |
| Patient Gender | | | | | | |
| Female | 72.9% | | | | | |
| Male | 26.7% | | 0.94 | 0.87-1.03 | −1.31 | .19 |
| Unknown/Not Stated | 0.4% | | 0.87 | 0.47-1.66 | −0.42 | .67 |
| Long Term Condition | 46.3% | | | | | |
| No | | | | | | |
| Yes | 27.7% | | 0.74 | 0.68-0.82 | −6.24 | <.001*** |

TABLE 12-continued

| (below)-First session predictors of reliable improvement. | | | | | |
|---|---|---|---|---|---|
| Unknown/Not Stated Psychotropic Medication | 26.0% | 0.77 | 0.70-0.85 | −5.42 | <.001*** |
| Prescribed Not Taking | 8.6% | | | | |
| Not Prescribed | 45.7% | 1.23 | 1.06-1.41 | 2.86 | .005** |
| Prescribed Taking | 42.3% | 1.00 | 0.88-1.14 | −.008 | .99 |
| Unknown/Not Stated | 3.4% | 0.87 | 0.69-1.11 | −1.31 | .26 |

Output of logistic regression investigating relationship between reliable improvement and number of words per feature in the first treatment session.
Standardized odds ratios indicate the effect of an increase of one standard deviation of a feature on the odds of improvement.
% of sessions indicates the percentage of the total number of sessions that contained utterances categorised as that feature.
Gender "Female", Long Term Conditions "No" and Psychotropic Medication "Prescribed Not Taking" were reference classes for the categorical variables.
*p < .001, p < .01, *p < .05

First Treatment Session Predictors of IAPT-Engagement

Finally, we investigated what session features are associated with IAPT-engagement (engagement being defined by IAPT as a patient attending a minimum of two treatment sessions). We performed a logistic regression analysis exploring the relationship between the features of a first treatment session and IAPT-engagement for all patients above the clinical threshold.

Figure 17:
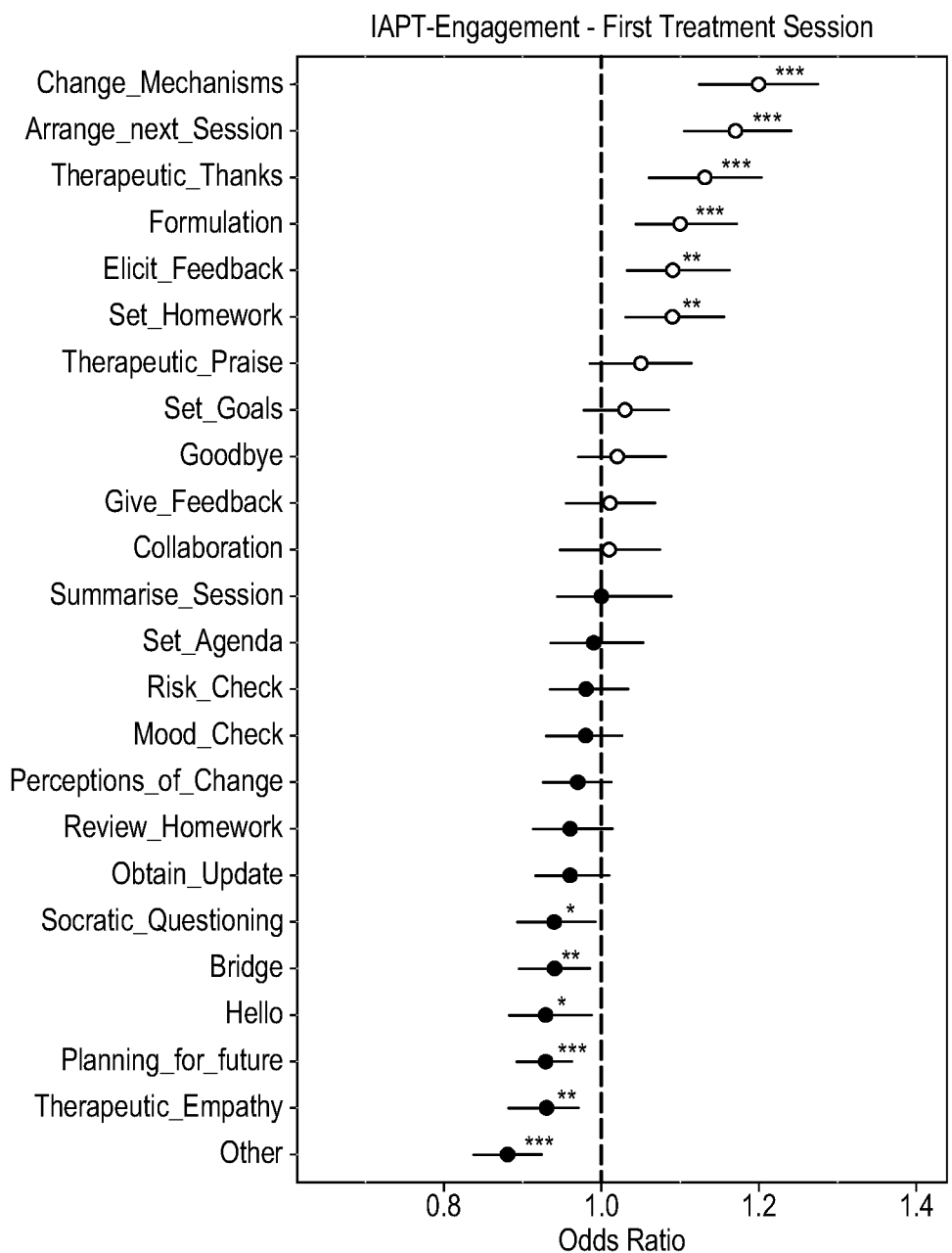

FIG. 17 shows the standardized odds ratios for each session feature included in the analysis (see Table 13 for details). We found that 'Change Mechanisms', 'Elicit Feedback', 'Set Homework', 'Arrange next Session', 'Therapeutic Thanks' and 'Formulation' were positively related with IAPT-engagement. By contrast, the amount of 'non-therapy' related content ('Other' and 'Hello') showed a negative relationship, along with 'Therapeutic Empathy', 'Socratic Questioning', 'Bridge', and 'Planning for the Future'. Patient age showed a positive relationship with IAPT-engagement, while starting PHQ-9 score, and being prescribed but not taking medication showed a negative relationship.

TABLE 13

| (below)-First session predictors of IAPT-engagement. | | | | | | |
|---|---|---|---|---|---|---|
| Feature | Mean no. of words (SD) | % of sessions | Odds Ratio | 95% CI | z-value | P-value |
| Hello | 14.4(34.7) | 99.7% | 0.93 | 0.88-0.99 | −2.45 | .01* |
| Mood Check | 5.6(10.5) | 48.0% | 0.98 | 0.93-1.03 | −0.96 | .33 |
| Obtain Update | 12.3(19.6) | 46.0% | 0.96 | 0.92-1.01 | −1.54 | .11 |
| Bridge | 9.7(24.8) | 22.6% | 0.94 | 0.90-0.98 | −2.63 | .008** |
| Risk Check | 22.8(54.7) | 30.4% | 0.98 | 0.94-1.03 | −0.69 | .48 |
| Set Agenda | 61.3(68.7) | 74.8% | 0.99 | 0.94-1.05 | −0.27 | .79 |
| Review Homework | 15.2(27.3) | 39.5% | 0.96 | 0.91-1.01 | −1.47 | .14 |
| Set Goals | 28.3(57.9) | 35.9% | 1.03 | 0.98-1.09 | 1.07 | .28 |
| Formulation | 53.2(126) | 31.0% | 1.10 | 1.04-1.17 | 3.33 | <.001*** |
| Give Feedback | 17.4(57.2) | 49.2% | 1.00 | 0.95-1.07 | 0.31 | .75 |
| Change Mechanisms | 426.5(279.5) | 97.5% | 1.20 | 1.12-1.27 | 5.56 | <.001*** |
| Perceptions of Change | 1.13(7.4) | 3.5% | 0.97 | 0.93-1.01 | −1.42 | .14 |
| Set Homework | 75.8(74.4) | 79.4% | 1.09 | 1.03-1.16 | 2.97 | <.002** |
| Planning for future | 0.56(8.5) | 0.9% | 0.93 | 0.89-0.96 | −3.77 | <.001*** |
| Elicit Feedback | 17.4(25) | 61.6% | 1.09 | 1.03-1.16 | 2.97 | .002** |
| Summarise Session | 0.24(4.67) | 0.4% | 1.00 | 0.94-1.09 | 0.01 | .98 |
| Arrange next Session | 33.1(32.6) | 85.5% | 1.17 | 1.10-1.24 | 5.30 | <.001*** |
| Goodbye | 16.2(15.6) | 91.1% | 1.02 | 0.97-1.08 | 0.83 | .40 |
| Socratic Questioning | 20(39.5) | 40.8% | 0.94 | 0.89-0.99 | −2.28 | .02* |
| Therapeutic Thanks | 8.5(24.3) | 20.1% | 1.13 | 1.06-1.20 | 3.73 | <.001*** |
| Therapeutic Empathy | 25.5(51.1) | 43.5% | 0.93 | 0.88-0.97 | −3.20 | .001** |
| Therapeutic Praise | 23.3(47) | 42.4% | 1.05 | 0.98-1.11 | 1.47 | .15 |
| Collaboration | 45.2(72.8) | 60.6% | 1.01 | 0.94-1.07 | 0.26 | .79 |
| Other | 141.1(117.4) | 96.9% | 0.88 | 0.84-0.92 | −5.12 | <.001*** |

| Variable | Mean/Prevalence (SD) | Odds Ratio | 95% CI | z-value | P-value |
|---|---|---|---|---|---|
| Session Duration (mins) | 63.1(9.9) | 1.26 | 1.20-1.33 | 8.89 | <001*** |
| Start Phq9 | 14.9(5.5) | 0.87 | 0.82-0.92 | −4.81 | <.001* |
| Start Gad7 | 8.8(5.9) | 1.00 | 0.95-1.06 | −0.01 | .99 |
| Patient Age | 34.8(12.0) | 1.07 | 1.02-1.13 | 2.64 | .008** |

TABLE 13-continued (below)-First session predictors of IAPT-engagement.

Patient Gender

| | | | | | |
|---|---|---|---|---|---|
| Female | 73.0% | | | | |
| Male | 26.7% | 1.02 | 0.91-1.01 | 0.28 | .78 |
| Unknown/Not Stated | 0.3% | 0.95 | 0.45-2.34 | −0.11 | .91 |

Long Term Condition

| | | | | | |
|---|---|---|---|---|---|
| No | 46.0% | | | | |
| Yes | 27.7% | 1.02 | 0.90-1.15 | 0.24 | .81 |
| Unknown/Not Stated | 26.3% | 0.90 | 0.80-1.02 | −1.68 | .09 |

Psychotropic Medication

| | | | | | |
|---|---|---|---|---|---|
| Prescribed Not Taking | 8.8% | | | | |
| Not Prescribed | 45.3% | 1.21 | 1.02-1.44 | 2.19 | .03* |
| Prescribed Taking | 42.4% | 1.20 | 1.01-1.47 | 2.06 | .04* |
| Unknown/Not Stated | 3.5% | 1.10 | 1.01-1.43 | 0.64 | .52 |

Output of logistic regression investigating relationship between patient engagement and number of words per feature in the first treatment session.
Standardized odds ratios indicate the effect of an increase of one standard deviation of a feature on the odds of engagement.
% of sessions indicates the percentage of the total number of first treatment sessions that contained utterances categorised as that feature.
Gender "Female", Long Term Conditions "No" and Psychotropic Medication "Prescribed Not Taking" were reference classes for the categorical variables.
*p < .001, p < .01, *p < .05.

The logistic regression model used revealed a positive relationship between the quantity of 'change mechanism'-related content and both reliable improvement and IAPT-engagement. Change mechanisms are cognitive and behavioural techniques used in CBT to address and evaluate key cognitions and to change dysfunctional thoughts and behaviours. The results indicate that increased use of these techniques in a treatment session is associated with greater odds of reliable improvement. This finding supports the key principles underlying CBT (i.e. that modifying cognitive and behavioural factors produces improvements in patient symptoms). Here, the category of 'Change Mechanisms' included any example of a cognitive or behavioural reattribution technique, as well as examples of skill-teaching, conceptualisation and psychoeducation. The model and methods disclosed herein can be further adapted to determine the relationship between the different types of change mechanisms and clinical outcomes.

Homework is used in CBT to help patients practice skills learned in therapy and generalise these skills to the real world. The results indicate that an increased amount of session content related to reviewing homework was positively associated with symptom improvement. There was no evidence indicating that setting homework was related to improvement, although it was found to be positively related with IAPT-engagement when occurring in the first treatment session. It is unclear whether reviewing homework plays a causal role in symptom improvement and/or whether increased occurrence of homework reviewing is reflective of a patient who has completed homework. However, taken together these findings suggest that setting homework in a first treatment session may help encourage patients to return for a second session.

The results show that the amount of content related to setting an agenda (both in the first treatment session and across sessions) is positively related with reliable improvement. Agenda setting involves the therapist and patient deciding on the topics to be discussed during the session. It is proposed that setting an agenda helps to focus the session and maximizes the use of time available, which in turn leads to better outcomes. The positive relationship between feedback and improvement supports the principle that the process of giving and eliciting feedback helps both the therapist and the patient develop a greater understanding of key issues and may also strengthen the therapeutic alliance. No evidence was found for a relationship between session summaries and outcomes, however the model identified only a small number of occurrences of session summary utterances (occurring in <0.5% of all sessions), suggesting therapists may have provided regular summaries/feedback throughout the session rather than summarising at the end of the session. As the session summary is one of the last features of a session, it is possible that its absence may be due to difficulties in time keeping.

Session content related to planning for the future after therapy and discussing perceptions of change was also positively related to improvement. A discussion of perceptions of change is only likely to occur after some degree of change has taken place, similarly, planning for a future after therapy is most likely to occur when patients are close to completing treatment and have moved (or are close) to improvement. As such, the increased occurrence of both features is likely to be reflective of treatment that is progressing well. Consistent with this, neither feature was significantly predictive of outcomes when using data from the first treatment session alone.

CBT is a goal-directed approach, with therapists and patients collaboratively setting goals at the start of treatment. The results suggest that this process is important in achieving positive clinical outcomes, evidenced by the positive relationship between goal setting in the first treatment session and reliable improvement. It was also found that content related to formulation (i.e. the beliefs and behavioural strategies that characterize a disorder) in the first treatment session was positively related with IAPT-engagement (there was also a borderline significant relationship with improvement), suggesting that introducing patients to the concept of formulation and/or placing their experiences within a cognitive behavioural framework helps patients to benefit from treatment.

It was found that non-therapy related content ('Hello' (Greeting), 'Goodbye' and 'Other') was negatively related with outcomes. 'Other' refers to content that did not fall under any of the other 23 categories and includes utterances related to technical/practical matters (e.g. "Sorry, I didn't mean to hit enter then") or non-therapeutic advice/conversations (e.g. "I think you should go and see your GP about your cough"). Greeting and saying goodbye to a patient are part of the structure of any session, but these results indicate that an excessive amount of time spent on these aspects of a session, along with 'bridge' (the therapist providing a bridge between the previous and current session), may reduce the quantity of 'active' intervention in a session. Importantly, these findings suggest that rather than the quantity of all conversation/contact with a therapist, it is the therapeutic nature of conversation and/or the 'dosage' of therapy delivered in a session that is predictive of an improvement in patient symptoms.

There was a strong negative relationship between risk checking and reliable improvement. Increased risk checking in a session is likely to be reflective of patients with more complex problems who report more thoughts of self-harm. Moreover, the quantity of risk checks occurring in a session will increase if a patient confirms that they feel at risk. If patients do report feeling at risk this is also likely to cause a deviation in the structure of the session and a subsequent reduction in the 'dosage' of CBT delivered.

No evidence was found that 'Mood Check' or 'Obtain Update' were related to outcomes, while the use of Socratic questioning and the presence of collaboration also showed no relationship with improvement. It should be noted that as 'Collaboration', 'Socratic Questioning', and aspects of therapeutic alliance do not occur as distinct utterances, it was chosen to use regular expressions rather than human annotation to identify these features.

One of the central issues in research into psychotherapy is whether different approaches work through specific factors or factors that are common to most psychotherapies. These findings indicate that both specific and common factors are measurably related to symptom improvement in CBT. It is notable that a positive association was found between improvement and/or IAPT-engagement for each of the six techniques that have been identified as distinguishing CBT from psychodynamic therapy: (i) use of homework and outside-of-session activities ('Review Homework', 'Set Homework'); (ii) direction of session activity ('Set Agenda'); (iii) teaching of skills used by patients to cope with symptoms ('Change Mechanisms'); (iv) emphasis on patients' future experiences ('Set Goals', 'Planning for the Future'); (v) providing patients with information about their disorder or symptoms ('Change Mechanisms'); and (vi) an intrapersonal/cognitive focus ('Change Mechanisms', 'Formulation').

Therapeutic alliance is thought to play an important role in all psychotherapeutic treatments although its relationship with outcomes appears moderate. The results presented herein reveal that different types of alliance are differentially related to outcomes: 'Therapeutic Praise' was positively related with improvement while 'Therapeutic Empathy' showed a negative relationship. Rather than playing a causal role in reducing the odds of improvement, increased use of empathy by a therapist may be indicative of a patient reporting a greater number of problems and may be reflective of greater symptom severity or complexity. Similarly, increased praise from a therapist (e.g. "well done", "that's great") may be reflective of a patient who is responding well to treatment. A positive association was found between 'Therapeutic Praise' in the first treatment session and improvement however, therefore early praise may play a causal role in helping a patient respond to treatment. The quantity of 'Therapeutic Thanks' in the first treatment session (e.g. "thanks for sharing") was also positively associated with IAPT-engagement, perhaps indicating that a therapist showing appreciation of a patient's contribution helps to develop the alliance and motivates the patient to return for a second treatment session. The methods and models described herein may be adapted to determine the causal relationship between the different aspects of therapeutic alliance and outcome.

The relationship between patient variables and outcome was also investigated. Patient age, absence of a long-term physical medical condition, not taking psychotropic medication, and severity of anxiety symptoms were all positively associated with reliable improvement. By contrast, severity of depressive symptoms, the presence of a long-term physical medical condition, and being prescribed psychotropic medication were negatively related to improvement. These results accord with those of a previous study investigating treatment outcomes in a sample of approximately three-thousand patients receiving IECBT (A. Catarino et al., Demographic and clinical predictors of response to internet-enabled Cognitive Behavioural Therapy for depression and anxiety. *BJPsych Open.* 4, 411-418 (2018)). As in the previous analysis, no evidence was found of a relationship between patient gender and outcomes. It was also found that a greater number of treatment sessions completed was positively related to improvement, suggesting that the overall 'dose' of CBT delivered is important. By contrast, longer treatment sessions (durations) across the course of treatment were associated with reduced odds of improvement. This may be reflective of therapists being less likely to end a session if a patient is failing to demonstrate an understanding of CBT-related skills/strategies.

The techniques described herein enable the measurement of the presence of a therapy feature (e.g. an utterance with a particular meaning made by a therapist) in a therapy session. Whether that feature is applied in a therapeutically appropriate/effective manner is not directly measured. By additionally assigning semantic representations to patient utterances and optionally quantifying them within a session, the relationship between patient and therapist content is directly determinable. For example by controlling for the number of problems expressed by the patient in a session it is possible to determine if sufficient therapist utterances assigned with a particular semantic representation are delivered when. Automatic categorisation of patient utterances would also enable the development of procedures for the detection of patients at risk.

Evidence is also presented to support the differential distribution of therapeutic interventions in the first session compared to subsequent ones. These results support the value of this approach and suggest that more detailed analysis of therapy features, perhaps using a more fine-grained scheme with more utterance categories, is likely to provide a valuable variant of the system/method. Similar analysis can be performed for the different treatment models encompassed by CBT, and for different patient cohorts, with the possibility of developing of new and improved treatments as well as personalized treatment protocols. The approach described herein also enables for the first time the identification of existing therapeutic strategies that do not affect outcomes, or those only minimally associated with positive outcomes. Removing or minimising these strategies is expected to make treatments more efficient and effective; thereby improving outcomes for patients, using therapist time more efficiently, and making efficiency savings for healthcare payors such as employers, health insurers or health services. The identification of these minimally effective therapeutic strategies also permits research attention to be directed toward alternative mechanisms and the development of novel, more highly beneficial, treatments.

The work described herein provides the strongest evidence to date that CBT-specific change mechanisms are effective in reducing symptoms of depression and anxiety. This approach represents an important development of a data-driven understanding of mental health treatment and an improvement in the efficacy of psychotherapy.

Example 7

The effectiveness of the context-aware Therapy Insights Model (TIM) at categorising utterances was compared with known models.

A trained clinical scientist annotated 290 hours of therapy (11,221 utterances). TIM and the known models were trained on the same 230 hours of therapy.

Tuned on 30 hours:
Dropout
Batch-size
Word-level hidden dimensions
Utterance-level hidden dimensions
LSTM v GRU TIM and the known methods were tested on the same 30 hours of therapy, Micro- and Macro-averaged F1 Scores were used as measure of classification, and are presented in Tables 14 and 15.

Known models tested:
1. MLP
   a. a multi-layer perceptron with bag-of-words features
   b. simple unigram lexical features for each utterance
   c. no context
2. Starspace (Wu, L., et al., 2017, StarSpace: Embed All The Things! arXiv:1709.03856)
   a. Facebook's neural entity classifier
   b. outperforms fastText (Facebook)
   c. three approaches: embedding unigrams, bigrams, trigrams
3. BiLSTM-max is a bidirectional LSTM on each utterance with max-pooling (Conneau, A., et al., 2017, Supervised learning of universal sentence representations from natural language inference data. arXiv preprint arXiv:1705.02364.)

TABLE 14

Comparative Categorisation Results for TIM and known models on 30 hours Test Data.

| | | Model | | | | |
|---|---|---|---|---|---|---|
| | | Starspace | | | BiLSTM- | Therapy Insights Model (TIM) |
| | MLP | unigram | bigrams | trigrams | max | HiBiLSTM | BiHiBiLSTM |
| Micro-Avg F1 | 52.61% | 58.85% | 61.08% | 59.97% | 60.77% | 69.56% | 70.93% |
| Macro-Avg F1 | 44.19% | 52.69% | 54.25% | 53.26% | 58.03% | 63.00% | 65.40% |

TABLE 15

Breakdown of comparative categorisation of Test Data for TIM and known models by utterance category (Macro-average-F1)

| | | | Model | | | | |
|---|---|---|---|---|---|---|---|
| | | | Starspace | | | BiLSTM- | Therapy Insights Model (TIM) |
| No. | Category | MLP | unigram | bigrams | trigrams | max | HiBiLSTM | BiHiBiLSTM |
| 48 | arrange_next_session | 68.24% | 77.08% | 84.44% | 79.12% | 86.02% | 87.23% | 91.49% |
| 7 | bridge | 44.44% | 43.48% | 43.48% | 70.59% | 85.71% | 60.00% | 76.92% |
| 333 | change_mechanisms | 59.00% | 62.85% | 66.31% | 65.19% | 64.24% | 74.96% | 74.10% |
| 38 | eliciting_feedback | 49.18% | 61.11% | 60.61% | 58.07% | 61.11% | 67.69% | 77.61% |
| 67 | formulation | 37.50% | 47.71% | 42.86% | 37.90% | 55.86% | 80.65% | 72.44% |
| 38 | giving_feedback | 22.86% | 26.32% | 31.71% | 34.41% | 27.18% | 25.64% | 27.12% |
| 43 | goodbyes | 84.34% | 78.57% | 84.34% | 84.71% | 80.44% | 86.36% | 92.86% |
| 33 | greeting | 80.70% | 89.55% | 92.06% | 90.00% | 96.97% | 100.00% | 98.51% |
| 25 | mood_check | 76.19% | 74.07% | 75.47% | 73.91% | 76.00% | 76.19% | 78.26% |
| 59 | obtain_update | 38.30% | 54.72% | 48.49% | 46.60% | 44.66% | 51.69% | 62.14% |
| 265 | other | 52.25% | 62.23% | 61.19% | 59.26% | 57.58% | 63.70% | 65.54% |
| 7 | perceptions_of_change | 0.00% | 14.82% | 0.00% | 0.00% | 11.77% | 22.22% | 25.00% |
| 5 | planning_for_future | 0.00% | 0.00% | 11.77% | 0.00% | 0.00% | 0.00% | 0.00% |
| 27 | review_homework | 20.00% | 48.49% | 43.08% | 36.67% | 56.52% | 56.60% | 55.81% |
| 31 | risk_check | 45.46% | 66.67% | 73.68% | 67.86% | 73.33% | 90.32% | 82.54% |
| 44 | set_agenda | 54.29% | 57.14% | 61.33% | 62.65% | 61.73% | 72.29% | 68.09% |
| 48 | set_goals | 33.33% | 45.00% | 48.78% | 47.37% | 58.54% | 61.36% | 69.47% |
| 46 | setting_homework | 29.41% | 38.71% | 46.91% | 44.44% | 46.94% | 57.14% | 59.34% |

Example 8

Inter-annotator agreement measure for human annotators and Therapy Insights Model.

A trained clinical scientist (annotator) annotated 20 therapy transcripts, following which a therapist re-annotated the same 20 therapy transcripts already categorised by the original annotator for agreement purposes. Categorisation of the transcripts by the annotator and the therapist was compared, and the annotator and therapist categorisations were also compared with those generated by the Therapy Insights Model (TIM).

The agreement measures are shown in Table 16.

TABLE 16

Inter-annotator agreement measures

| | Cohen's Kappa | | |
| --- | --- | --- | --- |
| Category | Annotator vs Therapist | Annotator vs TIM | Therapist vs TIM |
| arrange_next_session | 0.93 | 0.86 | 0.84 |
| bridge | 0.44 | 0.56 | 0.4 |
| change_mechanisms | 0.47 | 0.52 | 0.39 |
| eliciting_feedback | 0.47 | 0.6 | 0.38 |
| formulation | 0.45 | 0.63 | 0.52 |
| giving_feedback | 0.25 | 0.34 | 0.15 |
| goodbyes | 0.8 | 0.91 | 0.86 |
| greeting | 0.94 | 1 | 0.94 |
| mood_check | 0.43 | 0.68 | 0.47 |
| obtain_update | 0.42 | 0.6 | 0.28 |
| other | 0.57 | 0.44 | 0.36 |
| perceptions_of_change | −0.01 | 0.25 | 0 |
| planning_for_future | 0.6 | 0.48 | 0.44 |
| review_homework | 0.55 | 0.39 | 0.28 |
| risk_check | 0.92 | 0.72 | 0.6 |
| set_agenda | 0.72 | 0.76 | 0.74 |
| set_goals | 0.66 | 0.63 | 0.86 |
| setting_homework | 0.56 | 0.58 | 0.42 |
| Average | 0.565 | 0.608 | 0.496 |

Results

The measure of TIM's agreement with the original annotator is higher than that for the therapist, therefore as would be expected TIM has learned some of the idiosyncrasies of the original annotator.

The agreement scores for original annotator vs therapist (second human annotator) and original annotator vs TIM are very similar, suggesting that Tim agrees with its trainer as much as another human does.

The agreement measures for certain categories were lower than others, the below categories may be considered confusion classes as they are often confused for each other:

'change_mechanisms' and 'formulation',
'mood_check' and 'obtain_update'

Example 9

Automated Quality Assurance of Therapists

The CTSR (Cognitive Therapy Scale Revised (https://www.getselfhelp.co.uk/docs/CTSR.pdf)) tool is the current standard instrument for measuring the competency of CBT practitioners. It is a manual tool whereby a supervisor assesses the competency of a therapist by marking 12 quality items on a 0-6 scale according to how well the therapist displayed those quality items during a particular therapy session (i.e. it provides a measure of the quality of a therapy session).

An automated tool/method for measuring the competency of CBT practitioners (i.e. automated quality assurance of therapists) was developed.

In this study, supervisors performed manual CTSR assessments on 3 session transcripts for each of 255 therapists (3×255 CTSRs). The average of the total score of the CTSRs for each therapist was used as a manual measure of competence of that therapist (human CTSR competency score).

Automated QA—Recovery Rate

For each of the same 255 therapists, the machine learned automatic annotation tool (the (deep learning) utterance assignment model, or the first part or first portion of the (deep learning) HiBiLSTM Therapy Insights Model (TIM)) was applied individually to all session transcripts for all cases (individual patients) available (thereby determining the amount (absolute number) of 'set_agenda', 'setting_homework' etc. categorisations (features) in each transcript). A quality measure for each therapy session was then determined using a linear regression model (the second part of the deep learning model (the second part of the HiBiLSTM therapy insights model)), that correlated symptoms at the case (patient) level with combined session features. The model had been trained using transcript and symptom data derived from approximately 14,000 engaged patients (those who attended at least their first and second therapy sessions). Patient symptoms for the training data were measured by summing the GAD-7 and PHQ-9 questionnaire scores as self-reported by the patients (symptom score). The quality measure for each session transcript generated by the linear regression model was therefore a prediction of the symptom score. The quality measures of all therapy sessions provided by a particular one of the 255 therapists were averaged across all their cases (patients) to determine an automatic therapy competency score (recovery) for that therapist.

Figure 18:
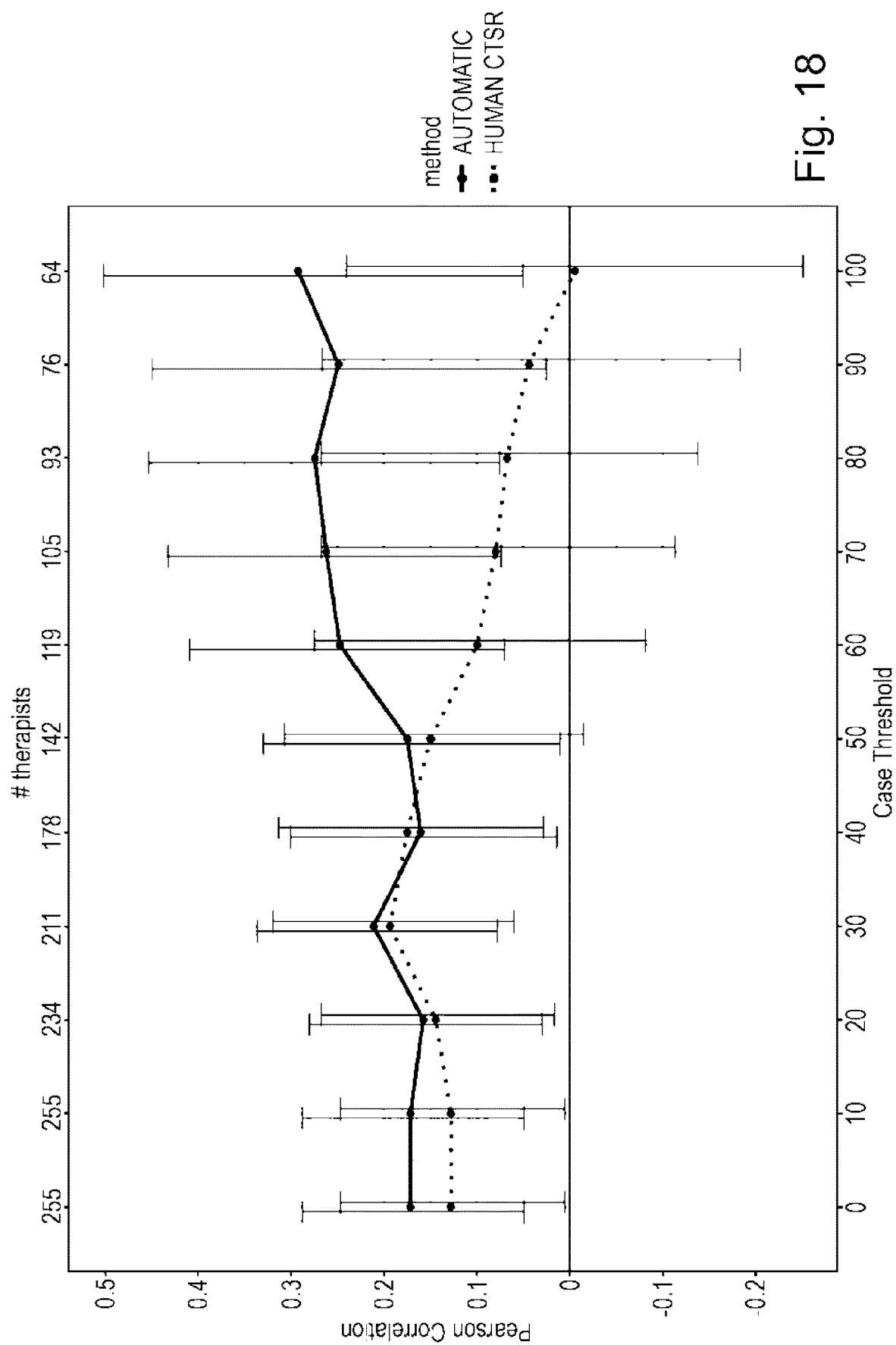

For each therapist, it was further determined how well their competency scores (human CTSR or automatic therapy competency score(recovery)) correlated with the effectiveness of the therapy delivered (where effectiveness of therapy delivered was expressed as a therapist recovery rate i.e. the number of patients for that therapist who recovered at the end of the therapy process, divided by the number of patients for that therapist who engaged in treatment (attended their first and second treatment sessions)). This is illustrated in FIG. 18. In that figure the dotted trend line shows the human CTSR competency score vs. recovery rate correlation, whereas the solid trend line shows the automatic therapy competency score vs. recovery rate correlation. Therapists were filtered by the number of cases seen: on the bottom x-axis (case threshold), 0 indicates all therapists who have seen more than 0 cases, whilst 100 indicates all therapists who have seen more than 100 cases. The top x-axis shows the number of therapists who are selected by the filtering at the corresponding case threshold (e.g. all 255 therapists have seen more than 0 cases, while 64 therapists have seen over 100 cases). Stratifying the data by case load allows the accuracy of the therapist competence assessment methods to be measured as case load varies.

The automated approach (whereby the automatic therapy competency score (recovery) was generated) showed significant correlation with recovery rate (as the error bars for those data points do not intersect 0) for therapists with all numbers of case-loads (x-axis). The automated approach to therapist competency (automatic therapy competency score (recovery)) was more highly correlated with therapist recovery rate than the human CTSR scores. Therefore the automated approach to quality assurance of therapists was more reliable than the current standard instrument (human/manual CTSR). Further, the automated approach took into account all sessions that a therapist conducted, not just a small sample as is the case with the manually rated (human)

CTSR. For therapists who conduct a large number of therapy sessions/have a large number of cases, the manual (human) CTSR is a very poor reflection of effectiveness as measured by recovery rate (as case threshold increases on the X-axis, the error bars for the human CTSR vs recovery rate correlation data points intersect 0 by an increasing amount.) This means that evaluating a low number of sessions (as is necessarily the case for manually conducted CTSR) is unrepresentative of the therapist's practice over a larger number of cases.

Automated QA—Engagement Rate

The automated tool/method for measuring the competency of CBT practitioners was further validated, by using it to predict patient engagement (defined as the likelihood a patient will return for a second therapy session).

The same supervisor-performed manual CTSR assessments on 3 session transcripts for each therapist (3×255 CTSRs) were used for comparison. Again, the average of the total score of the CTSRs for each of the 255 therapists was used (human CTSR competency score).

Starting from features of therapy present in the transcripts derived only from first therapy sessions (i.e. the amount (absolute number) of 'set_agenda', 'setting_homework' etc. categorisations (features) in the first session transcripts as determined by the first part of the HiBiLSTM Therapy Insights Model (TIM)), a logistic regression model (the second part of the deep learning model (HiBiLSTM therapy insights model)), was built to inform an engagement item in the automated approach to therapist competency, in order to predict whether or not a patient will attend their second therapy session. The regression was trained using over 21,078 cases (i.e. over 21,078 first-session transcripts), of which approximately 14,000 transcripts related to engaged patients (cases) (engagement=1), and approximately 7,000 transcripts related to non-engaged patients (cases) (engagement=0). Once trained, the model was then used to predict the engagement item for every first session delivered by the 255 therapists under assessment. The engagement rate for a particular therapist was then determined, by aggregating the engagement item for every first session delivered by that therapist. The engagement rate was considered an automatic therapy competency score (engagement).

For each therapist, it was further determined how well these competency scores (human CTSR or automatic therapy competency score (engagement)) correlated (using Pearson correlation) with actual (measured) engagement rate (the frequency with which patients returned for a second session with that therapist). This is illustrated in FIG. 19. In that figure the dotted trend line shows the human CTSR competency score vs. measured engagement rate correlation, whereas the solid trend line shows the automatic therapy competency score (engagement) vs. measured engagement rate correlation. Again, therapists were filtered by the number of cases seen, similarly to the Recovery rate approach illustrated in FIG. 18.

The automated approach (generating the automatic therapy competency score (engagement)) was nearly significantly correlated with engagement rate for therapists at all case-load levels (x-axis), and was more highly correlated with measured engagement rate than standard (human) CTSR. Therefore the automated approach to quality assurance of therapists was more reliable than the current standard instrument (human/manual CTSR). Furthermore, the automated approach takes into account all first sessions that a therapist has conducted. This contrasts with manual CTSR, whereby only a small sample of sessions (that may or may not be first sessions) is assessed. Particularly for therapists who conducted a large number of therapy sessions/have a large number of cases, the manual CTSR was a very poor reflection of engagement and was surpassed by the automated approach.

Therefore, use of the automated tool/method to determine competency scores (either linked to recovery or engagement rate) led to more accurate QA of therapists than the currently adopted method (manual CTSR).

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

The term "comprising" encompasses "including" as well as "consisting" e.g. a composition "comprising" X may consist exclusively of X or may include something additional e.g. X+Y.

The terms "about" or "approximately" in relation to a numerical value x is optional and means, for example, x±10%.

The invention claimed is:

1. A computer-implemented method for taking one or more action relating to therapy, the method comprising:
receiving, by a computer, text data relating to a therapy session between a therapist and a patient;
dividing, by the computer, the text data into a plurality of utterances;
assigning, by the computer, a semantic representation to each of the plurality of utterances to produce a plurality of assigned utterances;
aggregating, by the computer, the plurality of assigned utterances to form a representation of the therapy session;
providing, by the computer, in real-time during the therapy session and based at least in part on utilizing a machine learning model, an output prediction comprising a measure of a quality of therapy delivered by the therapist, based on the representation of the therapy session and optionally one or more further input, of one or more characteristic of at least one of the patient, the therapist, and the therapy, wherein providing the output prediction comprising the measure of the quality of the therapy delivered by the therapist comprises:
determining, via the machine learning model and in real-time during the therapy session, that representation of the therapy session indicates that the therapy session is currently associated with a likelihood of patient recovery that is below average; and
automatically generating an alert, during the therapy session and in real-time via an interface to the therapist, indicating (i) at least one category of utterances as a cause for the likelihood of patient recovery being below average, and (ii) an adjustment of a frequency of utterances to be delivered to the patient for the at least one category of utterances to improve the likelihood of patient recovery, wherein the one or more action comprises providing at least one utterance in accordance with the frequency of utterances of the at least one category of utterances; and taking, by the computer, one or more action relating to the therapy determined to improve the quality of the therapy for a medical condition, wherein the one or more action is selected based on the output prediction meeting a predetermined at least one criterion.

2. The method according to claim 1, wherein assigning a semantic representation to each of the plurality of utterances is performed by at least a first part of a deep learning model, and providing an output prediction of one or more characteristic is performed by at least a second part of the deep learning model.

3. The method according to claim 1, wherein the plurality of utterances comprises combined patient and therapist utterances, only patient utterances, or only therapist utterances.

4. The method according to claim 1, wherein the optional further input, where present, comprises non-content related session features and/or patient variables.

5. The method according to claim 1, wherein:

receiving text data relating to a therapy session between a therapist and a patient comprises receiving text data relating to a plurality of therapy sessions;

aggregating the plurality of assigned utterances comprises forming a plurality of representations each relating to one of the plurality of therapy sessions; and providing an output prediction of one or more characteristic of at least one of the patient, the therapist and the therapy comprises providing a plurality of output predictions each relating to one of the plurality of therapy sessions.

6. The method according to claim 2, wherein the first part of the deep learning model comprises a bidirectional long short-term memory (BiLSTM) neural network or a hierarchical bidirectional long short-term memory (HiBiLSTM) neural network.

7. The method according to claim 1 wherein the one or more action comprises, in response to the output prediction or output predictions meeting the predetermined criterion, initiating an automated quality assurance process that comprises alerting a supervisor.

8. The method according to claim 1, wherein the therapy comprises psychotherapy.

9. The method according to claim 1, wherein the patient has the medical condition comprising a mental health disorder.

10. The method according to claim 9 wherein the mental health disorder is selected from depression or an anxiety disorder.

11. A computer program product comprising instructions which, when executed by at least one computer, cause the at least one computer to:

receive text data relating to a therapy session between a therapist and a patient;

divide the text data into a plurality of utterances;

assign a semantic representation to each of the plurality of utterances to produce a plurality of assigned utterances;

aggregate the plurality of assigned utterances to form a representation of the therapy session;

provide, in real-time during the therapy session and based at least in part on utilizing a machine learning model, an output prediction comprising a measure of a quality of therapy delivered by the therapist, based on the representation of the therapy session and optionally one or more further input, of one or more characteristic of at least one of the patient, the therapist and the therapy, wherein providing the output prediction comprising the measure of the quality of the therapy delivered by the therapist comprises:

determining, via the machine learning model and in real-time during the therapy session, that representation of the therapy session indicates that the therapy session is currently associated with a likelihood of patient recovery that is below average; and automatically generating an alert, during the therapy session and in real-time via an interface to the therapist, indicating (i) at least one category of utterances as a cause for the likelihood of patient recovery being below average, and (ii) an adjustment of a frequency of utterances to be delivered to the patient for the at least one category of utterances to improve the likelihood of patient recovery, wherein the one or more action comprises providing at least one utterance in accordance with the frequency of utterances of the at least one category of utterances; and take one or more action relating to the therapy determined to improve the quality of the therapy for a medical condition, wherein the one or more action is selected based on the output prediction meeting a predetermined at least one criterion.

12. A non-transitory computer-readable medium comprising instructions which, when executed by a computer, cause the computer to carry out the method of claim 1.

13. A data processing apparatus/device/system comprising means for carrying out the method according to claim 1.

14. A method of treatment of a mental health disorder in a patient, the method comprising:

receiving text data relating to a therapy session between a therapist and the patient;

dividing the text data into a plurality of utterances;

assigning a semantic representation to each of the plurality of utterances using at least a first part of a deep learning model, to produce a plurality of assigned utterances;

aggregating the plurality of assigned utterances to form a representation of the therapy session;

providing, in real-time during the therapy session and based at least in part on utilizing a machine learning model, an output prediction comprising a measure of a quality of therapy delivered by the therapist, based on the representation of the therapy session and optionally one or more further input and using at least a second part of a deep learning model, of one or more characteristic of at least one of the patient, the therapist and the therapy, wherein providing the output prediction comprising the measure of the quality of the therapy delivered by the therapist comprises:

determining, via the machine learning model and in real-time during the therapy session, that representation of the therapy session indicates that the therapy session is currently associated with a likelihood of patient recovery that is below average; and automatically generating an alert, during the therapy session and in real-time via an interface to the therapist, indicating (i) at least one category of utterances as a cause for the likelihood of patient recovery being below average, and (ii) an adjustment of a frequency of utterances to be delivered to the patient for the at least one category of utterances to improve the likelihood of patient recovery, wherein the one or more action comprises providing at least one utterance in accordance with the frequency of utterances of the at least one category of utterances; and taking one or more action relating to the therapy determined to improve the quality of the therapy for a medical condition, wherein the one or more action is selected based on the output prediction meeting a predetermined at least one criterion.

15. The method according to claim 1, wherein the predetermined at least one criterion comprises a maximum level for a first utterance category and a minimum level for a second utterance category, and wherein providing the output prediction comprises:

automatically generating an alert, during the therapy session and in real-time via an interface to the therapist, indicating that (i) the first utterance category has exceeded the maximum level, (ii) that the second utterance category has not exceeded the minimum level, or (iii) that the first utterance category has exceeded the maximum level and the second utterance category has not exceeded the minimum level.

16. The method according to claim 15, further comprising:

automatically setting the maximum level for the first utterance category based at least in part on a determination of positive correlation between the first utterance category and improved therapy outcomes.

17. The method according to claim 1, further comprising:

receiving, subsequent to the generation of the alert, additional text data relating to the therapy session;

dividing the additional text data into an additional plurality of utterances;

assigning an additional semantic representation to each of the additional plurality of utterances to produce an additional plurality of assigned utterances;

aggregating the additional plurality of assigned utterances to form an additional representation of the therapy session; and providing, in real-time during the therapy session and based at least in part on utilizing the machine learning model, an updated output prediction indicating that the likelihood of patient recovery has improved.

18. The method according to claim 1, further comprising:

identifying a treatment plan to be performed during the therapy session, wherein providing the output prediction comprises:

automatically determining, in real-time during the therapy session, that the representation of the therapy session indicates a deviation from the treatment plan; and automatically generating an alert, during the therapy session and in real-time via an interface to the therapist, indicating (i) that the therapy session has deviated from the treatment plan, and (ii) the one or more actions to improve the quality of the therapy for the medical condition based on the treatment plan.

19. The method according to claim 1, further comprising:

automatically determining the medical condition based at least in part on the plurality of assigned utterances; and automatically generating an alert indicating a treatment protocol based at least in part on the medical condition, wherein the treatment protocol comprises the one or more actions relating to the therapy determined to improve the quality of the therapy for the medical condition.

\* \* \* \* \*